United States Patent
Breslich et al.

(10) Patent No.: US 11,723,646 B2
(45) Date of Patent: Aug. 15, 2023

(54) SELF-DRILLING ALL-SUTURE ANCHOR

(71) Applicant: CONMED CORPORATION, Utica, NY (US)

(72) Inventors: Grady Breslich, Bradenton, FL (US); James Barber, Largo, FL (US); Adrian Bosworth, Bradenton, FL (US); Bennie W. Gladdish, Jr., Odessa, FL (US); Peter Miller, Largo, FL (US); John K. Sieh, Safety Harbor, FL (US)

(73) Assignee: CONMED CORPORATION, Utica, NY (US)

( * ) Notice: Subject to any disclaimer, the term of this patent is extended or adjusted under 35 U.S.C. 154(b) by 757 days.

(21) Appl. No.: 16/634,306

(22) PCT Filed: Jul. 24, 2018

(86) PCT No.: PCT/US2018/043446
§ 371 (c)(1),
(2) Date: Jan. 27, 2020

(87) PCT Pub. No.: WO2019/023205
PCT Pub. Date: Jan. 31, 2019

(65) Prior Publication Data
US 2020/0360008 A1    Nov. 19, 2020

Related U.S. Application Data

(60) Provisional application No. 62/631,034, filed on Feb. 15, 2018, provisional application No. 62/618,851, (Continued)

(51) Int. Cl.
*A61B 17/04* (2006.01)
*A61B 17/17* (2006.01)

(52) U.S. Cl.
CPC .......... *A61B 17/0401* (2013.01); *A61B 17/17* (2013.01); *A61B 2017/0409* (2013.01); (Continued)

(58) Field of Classification Search
CPC ................ A61B 17/17; A61B 17/0401; A61B 2017/044; A61B 2017/0458; (Continued)

(56) References Cited

U.S. PATENT DOCUMENTS

| 5,411,523 A | 5/1995 | Goble |
| 5,591,207 A | 1/1997 | Coleman |

(Continued)

FOREIGN PATENT DOCUMENTS

| JP | 2013-128772 A2 | 7/2013 |
| KR | 1020130096708 | 8/2013 |

(Continued)

OTHER PUBLICATIONS

International Search Report Form PCT/ISA/220, International Application No. PCT/US2018/042446, pp. 1-19, dated Nov. 6, 2018.

(Continued)

*Primary Examiner* — Dianne Dornbusch
(74) *Attorney, Agent, or Firm* — Bond, Schoeneck & King, PLLC

(57) ABSTRACT

A self-drilling suture inserter including a shaft extending along a longitudinal axis having a proximal end and a distal end, which is connected to a tubular portion. The inserter also includes an inserter tip, which is attached to and extends distally from the shaft. The inserter tip comprises a suture anchor retention slot extending therethrough. The inserter tip also comprises a distal end with a drilling point. The tubular portion can also include an outer tube having a first (Continued)

inner volume and a suture tube having a second inner volume. The suture tube extends within the first inner volume of the outer tube.

21 Claims, 72 Drawing Sheets

Related U.S. Application Data filed on Jan. 18, 2018, provisional application No. 62/572,369, filed on Oct. 13, 2017, provisional application No. 62/543,516, filed on Aug. 10, 2017, provisional application No. 62/536,208, filed on Jul. 24, 2017.

(52) U.S. Cl.
CPC ............... *A61B 2017/0414* (2013.01); *A61B 2017/0496* (2013.01)

(58) Field of Classification Search
CPC .... A61B 2017/0445; A61B 2017/0406; A61B 2017/0414; A61B 2017/0409; A61B 2017/0496; A61B 2017/0464
See application file for complete search history.

(56) References Cited

U.S. PATENT DOCUMENTS

| | | | |
|---|---|---|---|
| 5,851,219 A | 12/1998 | Goble et al. | |
| 5,904,704 A | 5/1999 | Goble et al. | |
| 6,156,039 A | 12/2000 | Thal | |
| 6,626,916 B1 | 9/2003 | Yeung et al. | |
| 7,025,770 B2 | 4/2006 | McGuire et al. | |
| 7,041,120 B2 | 5/2006 | Li et al. | |
| 7,749,250 B2 | 7/2010 | Stone et al. | |
| 8,202,318 B2 | 6/2012 | Willobee | |
| 8,273,106 B2 | 9/2012 | Stone et al. | |
| 8,591,545 B2 | 11/2013 | Lunn et al. | |
| 8,795,334 B2 | 8/2014 | Astorino et al. | |
| 9,044,224 B2 | 6/2015 | Lauria | |
| 9,084,597 B2 | 7/2015 | Arai et al. | |
| 9,173,652 B2 | 11/2015 | Lombardo et al. | |
| 9,320,512 B2 | 4/2016 | Dooney, Jr. | |
| 9,370,352 B2 | 6/2016 | Astorino et al. | |
| 9,421,010 B2 | 8/2016 | Dreyfuss | |
| 9,445,803 B2 | 9/2016 | Marchand et al. | |
| 9,585,654 B2 | 3/2017 | Dean et al. | |
| 9,610,074 B2 | 4/2017 | Martin | |
| 9,826,971 B2 | 11/2017 | Lombardo et al. | |
| 10,092,284 B2 | 10/2018 | Bouduban et al. | |
| 10,182,806 B2 | 1/2019 | Foerster | |
| 10,258,326 B2 | 4/2019 | Sung | |
| 10,383,619 B2 | 8/2019 | Thal | |
| 10,448,944 B2 | 10/2019 | Marchand et al. | |
| 10,568,616 B2 | 2/2020 | Monllor et al. | |
| 10,631,844 B2 | 4/2020 | Astorino et al. | |
| 10,687,798 B2 | 6/2020 | Lombardo et al. | |
| 10,722,343 B2 | 7/2020 | Pilgeram et al. | |
| 2010/0298872 A1 | 11/2010 | Berndt et al. | |
| 2011/0054524 A1 | 3/2011 | Beevers et al. | |
| 2011/0276137 A1 | 11/2011 | Seedhom et al. | |
| 2013/0018416 A1 | 1/2013 | Lombardo et al. | |
| 2013/0345751 A1 | 12/2013 | Beck | |
| 2014/0257383 A1* | 9/2014 | Lombardo | A61B 17/0401 606/232 |
| 2015/0032155 A1 | 1/2015 | Dreyfuss et al. | |
| 2015/0066079 A1 | 3/2015 | Schmieding | |
| 2016/0157844 A1 | 6/2016 | Guy | |
| 2016/0270777 A1 | 9/2016 | Miller et al. | |
| 2016/0296223 A1* | 10/2016 | Monllor | A61B 17/0401 |
| 2017/0055975 A1 | 3/2017 | Thal | |
| 2017/0071590 A1 | 3/2017 | Macleod | |
| 2017/0156727 A1 | 6/2017 | Wilson-Wirth et al. | |
| 2017/0181739 A1 | 6/2017 | Breslich | |
| 2017/0252031 A1 | 9/2017 | Harari et al. | |
| 2018/0049734 A1 | 2/2018 | Kam | |
| 2018/0235746 A1 | 8/2018 | Pilgeram et al. | |
| 2018/0296207 A1 | 10/2018 | Burkhart et al. | |

FOREIGN PATENT DOCUMENTS

| | | |
|---|---|---|
| WO | 01/54586 | 8/2001 |
| WO | 2013/120004 | 8/2013 |
| WO | 2016/154099 | 9/2016 |
| WO | 2017/117100 | 7/2017 |
| WO | 2017/139132 | 8/2017 |
| WO | 2018/035232 | 2/2018 |

OTHER PUBLICATIONS

KR Office Action, App. No. 10-2022-7000010, dated Jun. 2, 2022, pp. 1-11.

JP Office Action, App. No. 2021-150114, dated Sep. 6, 2022, pp. 1-9.

* cited by examiner

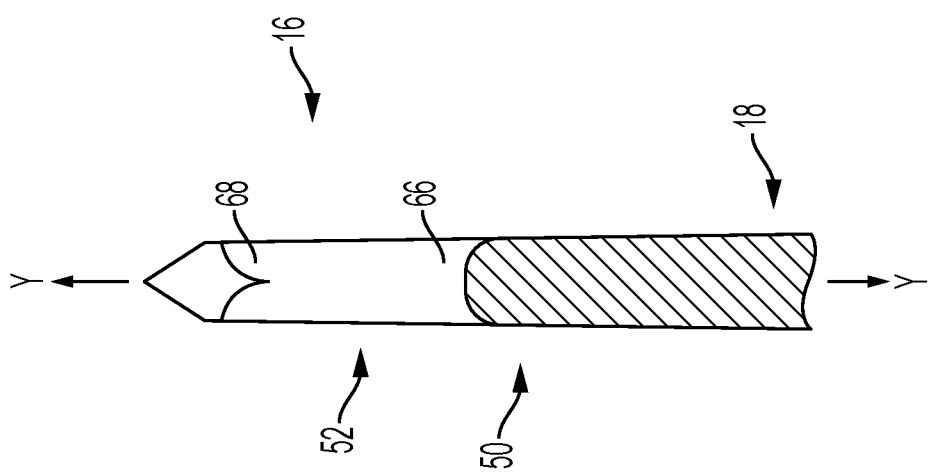

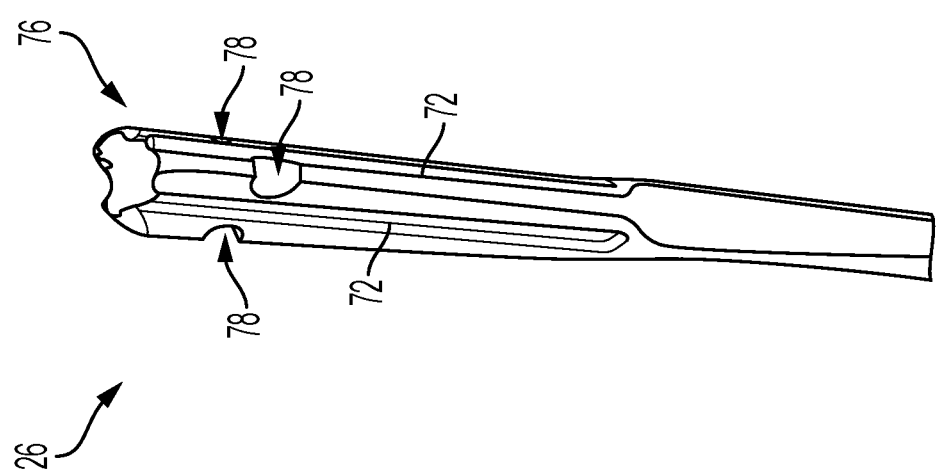

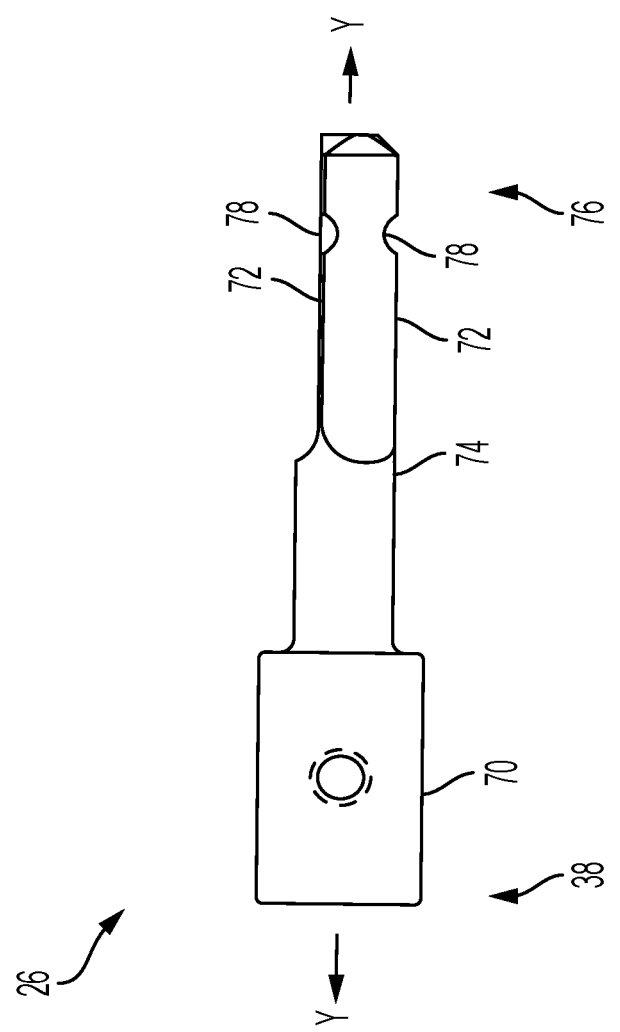

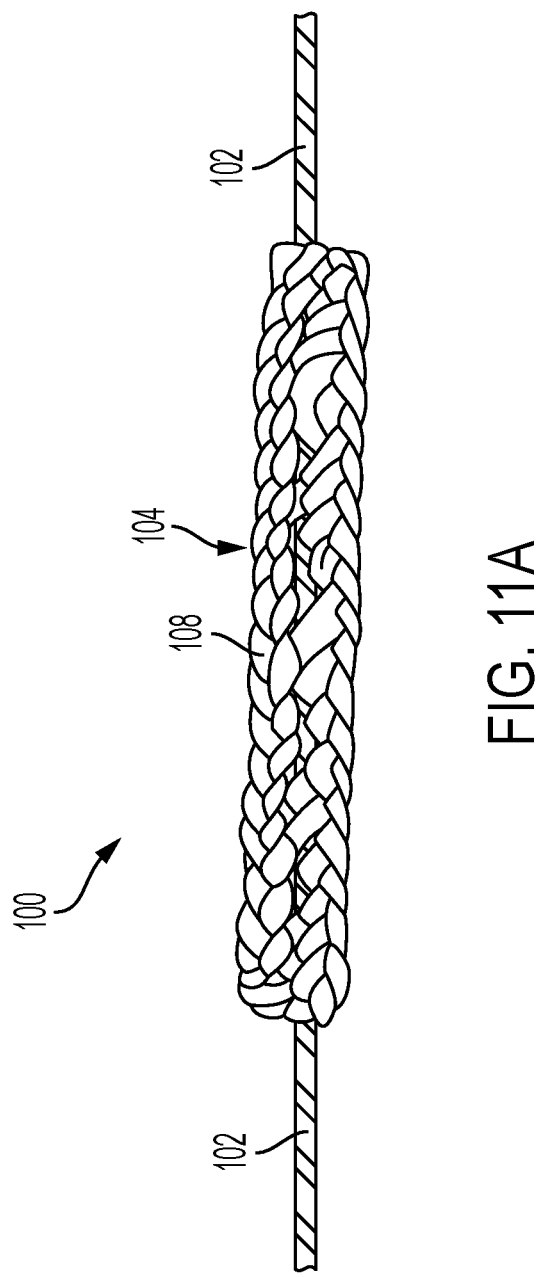

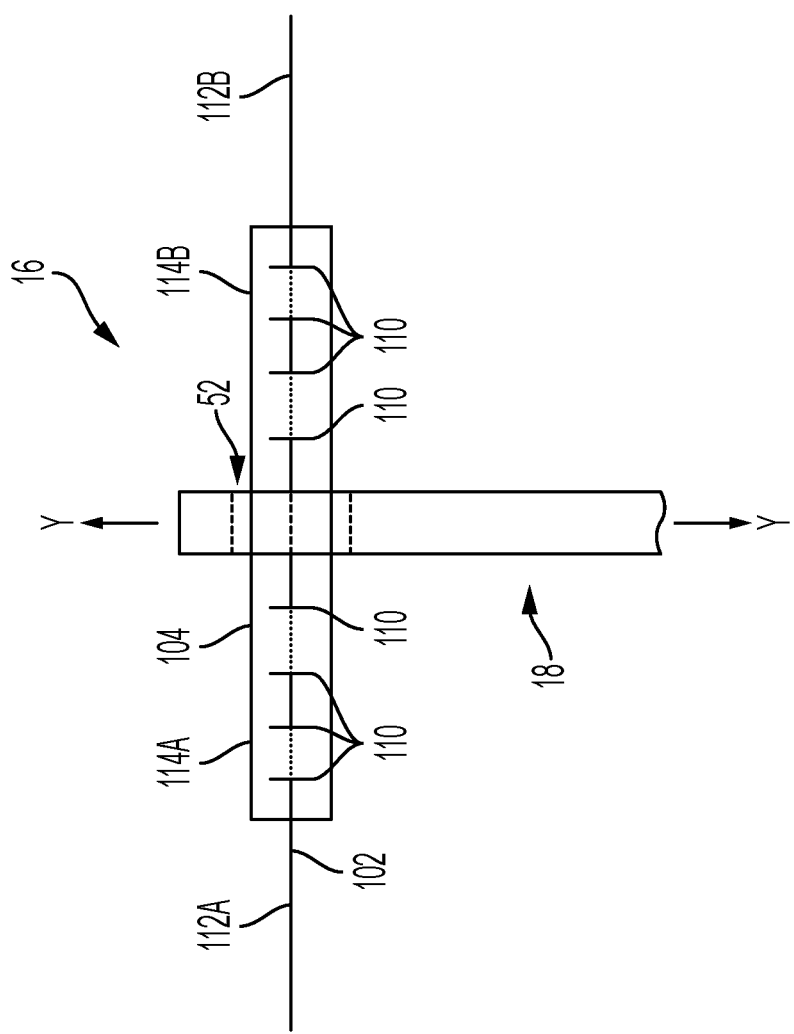

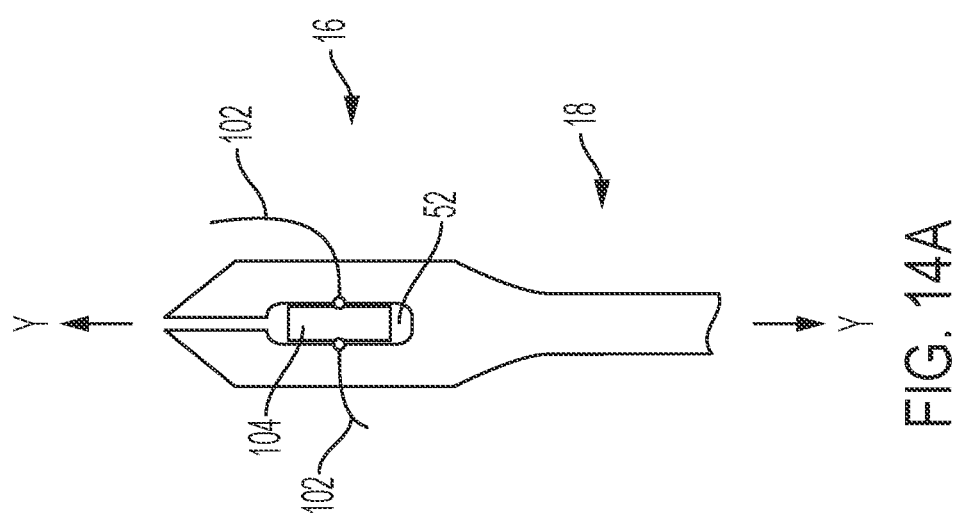

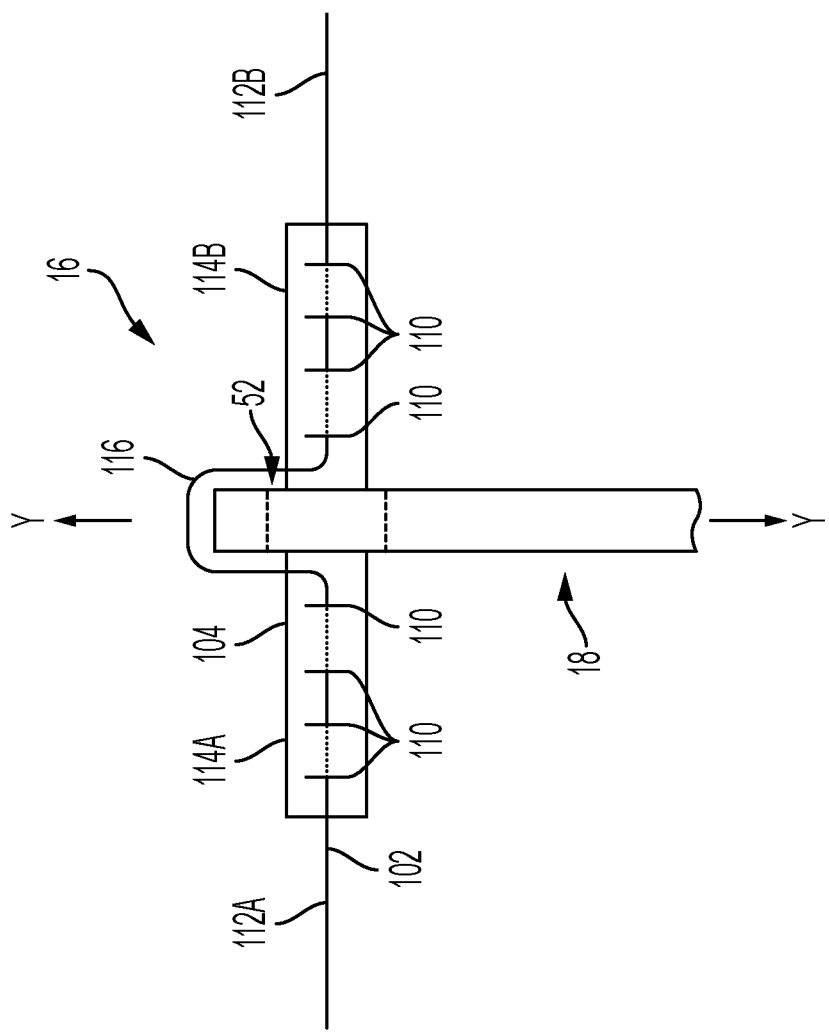

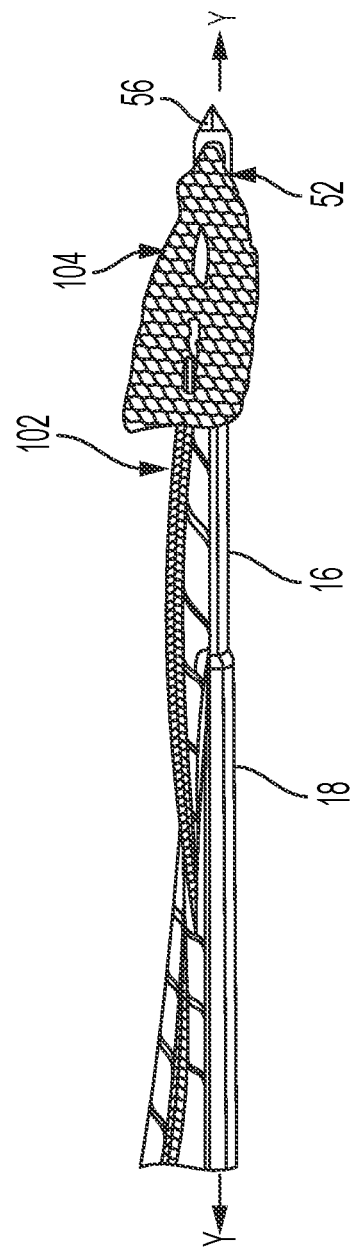

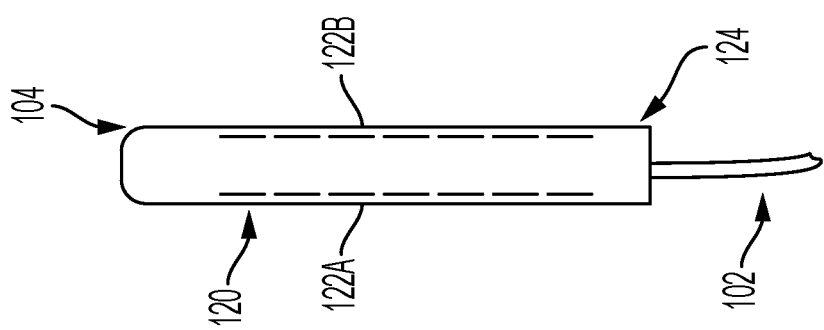

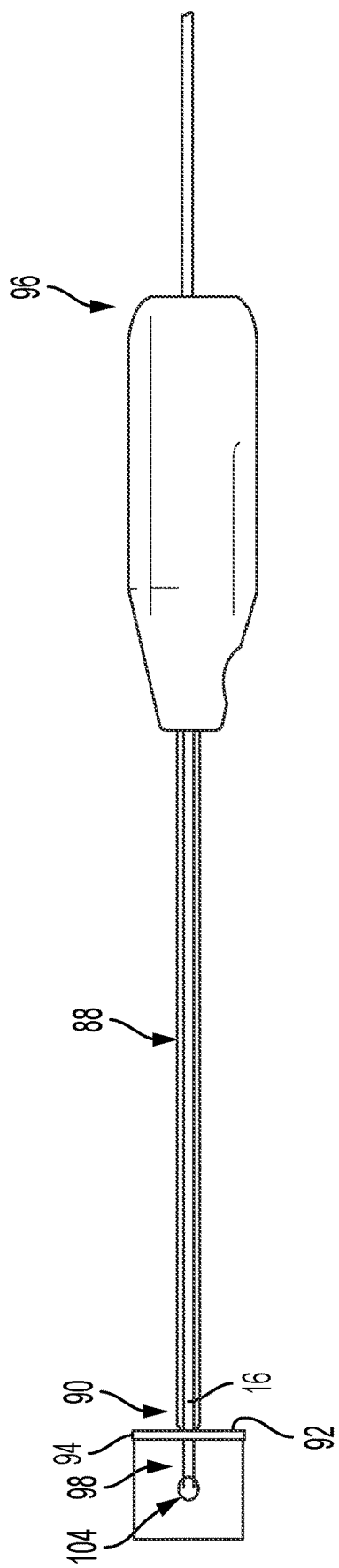

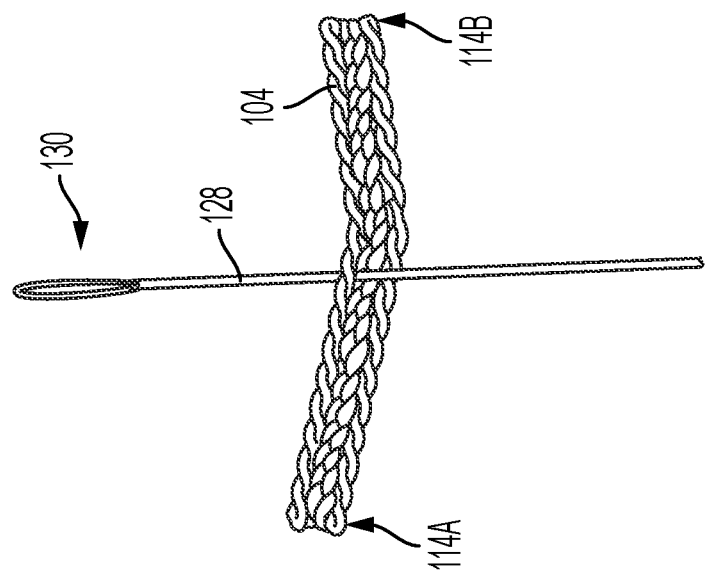

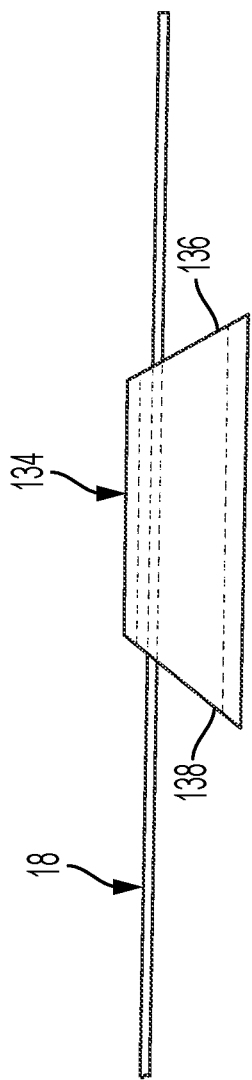

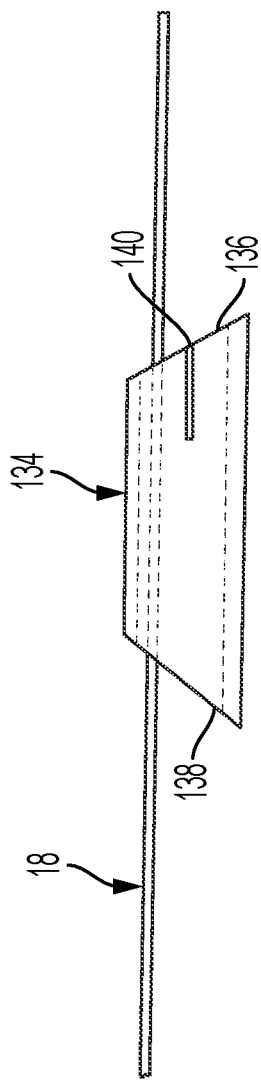

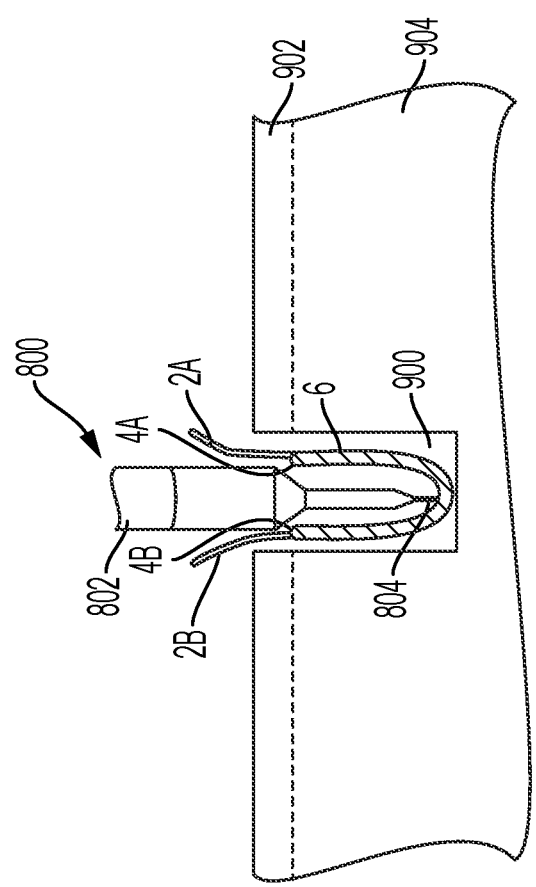

SELF-DRILLING ALL-SUTURE ANCHOR

CROSS-REFERENCE TO RELATED APPLICATION

The present application claims priority to and the benefit of U.S. Provisional Patent Application No. 62/572,369 filed on Oct. 13, 2017, U.S. Provisional Patent Application No. 62/618,851, filed on Jan. 18, 2018, U.S. Provisional Patent Application No. 62/631,034, filed on Feb. 15, 2018, Provisional Patent Application No. 62/543,516, filed on Aug. 10, 2017, and U.S. Provisional Patent Application No. 62/536,208, filed on Jul. 24, 2017.

BACKGROUND OF THE INVENTION

1. Field of the Invention

The present invention relates to drills, anchor drivers, and a drill guide for drilling a bone hole at a surgical repair site and inserting a suture anchor in the bone hole and, more particularly, to a self-drilling all-suture anchor and inserter.

2. Description of Related Art

Many orthopedic surgical and medical procedures require the fixation of one body to another body. Such bodies may include bone, soft tissue, and prosthetics. One body can be fixed in a position relative to another using connector devices, such as screws and suture anchors (e.g., cannulated knotless suture anchors and soft all suture anchors). For example, various orthopedic surgeries require the insertion and fixation of a suture anchor within a bone.

One example of a suture anchor is a soft suture anchor, such as the Y-Knot® device. See, e.g., U.S. Pat. No. 9,826,971. Since soft anchors are commonly made entirely of suture materials, they are sometimes called "all-suture" anchors, and generally include a fibrous construct anchor body portion (or fibrous, braided or woven fabric-type structure such as a flexible web, as described in U.S. Pat. No. 9,173,652) and a suture or filament portion. In a traditional Y-Knot device, the suture is pierced entirely through the braid material a number of times, such that the suture passes through a "front" surface and a "back" surface. When a Y-Knot anchor is constructed in the traditional manner, the segments of suture on the back surface of the braid are in contact with bone and can be abraded by the bone due to friction.

There are at least two general, conventional methods for inserting a suture anchor within a bone. In one method, a bone hole is created and prepared using a drill bit. The drill bit is typically advanced through a drill guide to create the bone hole and then, a suture anchor is passed through or down the drill guide into the bone hole for deployment. If the drill guide is moved between creation of the bone hole and advancement of the suture anchor, the drill guide may be moved out of alignment with the bone hole. If the drill guide is no longer aligned with the bone hole, the suture anchor often cannot be inserted and deployed. Therefore, the creation of a second bone hole is often required when drill guide moves out of alignment with the first bone hole.

In a second method, the drilling step is eliminated in an attempt to avoid the aforementioned misalignment issue. A self-punching suture anchor, such as the Y-Knot RC Suture Anchor, for example, is designed with an inserter that allows the anchor in the inserter to be directly positioned on the bone at the desired location. When the anchor in the inserter is positioned at the desired location, the inserter can be hammered, forcing the anchor directly into the bone. However, hammering the anchor into the bone imparts impact forces to the bone which may be undesirable for some surgical site locations. For example, impact forces may be particularly undesirable at the glenoid bone or smaller bones, such as in the extremities. Further, self-punching anchors are generally required to be larger in size. Thus, such anchors may not only be undesirable but unusable in smaller bones.

Therefore, there is a need for a suture anchor inserter that can insert a small suture anchor into the bone without the need to drill a bone hole or to impart impact forces on the bone.

Description of the Related Art Section Disclaimer: To the extent that specific patents/publications/applications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/applications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention recognize that there are potential problems and/or disadvantages with the conventional methods for drilling a bone hole and inserting a suture anchor (as discussed herein and above). For example, removing a drill bit from the drill guide and replacing it with a driver to insert the suture anchor increases the risk of misalignment of the drill guide with the bone hole, which requires additional surgical time and risks trauma to the surrounding tissue and bone. In another example, hammering the anchor into the bone imparts impact forces to the bone which may be undesirable for some surgical site locations. Therefore, a need exists for a simple-to-use suture anchor inserter that can insert a suture anchor into the bone without the need to drill a bone hole or to impart impact forces on the bone. Various embodiments of the present invention may be advantageous in that they may solve or reduce one or more of the potential problems and/or disadvantages discussed herein.

The present disclosure is directed to an inventive configuration, structure, and resulting function of a self-drilling anchor inserter configured to insert suture anchors into bone. According to one aspect, the present invention is a suture anchor inserter. The suture anchor inserter includes a shaft extending along a longitudinal axis having a proximal end and a distal end, which is connected to a tubular portion. The inserter also includes an inserter tip, which is attached to and extends distally from the shaft. The inserter tip comprises a suture anchor retention slot extending therethrough. The inserter tip also comprises a distal end with a drilling point. The tubular portion can also include, but is not limited to, an outer tube having a first inner volume and a suture tube having a second inner volume. The suture tube extends within the first inner volume of the outer tube.

According to another aspect, the present invention is a self-drilling anchor inserter system further including an anchor with a length of suture positioned (or can be woven) therethrough. The anchor extends through the suture anchor retention slot such that a first end of the length of suture extends along a first side of the shaft and a second end of the length of suture extends along a second side of the shaft.

According to yet another aspect, a method of drilling a bone hole and inserting a suture anchor in the bone hole includes, but is not limited to, the steps of: (i) providing an inserter comprising a shaft extending along a longitudinal axis having a proximal end and a distal end, the distal end connected to a tubular portion, an inserter tip attached to and extending distally from the shaft, a suture anchor retention slot extending through the inserter tip, a drilling point at the distal end of the inserter tip, an outer tube of the tubular portion having a first inner volume, and a suture tube of the tubular portion having a second inner volume, the suture tube extending within the first inner volume of the outer tube; (ii) inserting a suture anchor with a length of suture positioned (or can be woven) therethrough through the suture anchor retention slot; (iii) tensioning a first end of the length of suture on a first side of the shaft and a second end of the length of suture on a second side of the shaft; (iv) positioning a distal end of a guide tube against a bone; (v) extending the inserter through the guide tube such that the drilling point is at a surface of a bone at a desired bone hole location; and (vi) drilling a bone hole into the bone with the drilling point of the inserter.

Suture material or sutures, as the terms are used and described herein, can include monofilament or multi-filament suture as well as any other metallic or non-metallic filamentary or wire-like material suitable for performing the function of a suture. This material can include both bioabsorbable and non-absorbable materials.

Suture anchors, as the term is used herein, can include soft suture anchors and rigid suture anchors. Soft suture anchors are formed from filaments of suture material which are retained within pre-formed bone holes by being deformable to increase their diameter to a size greater than that of the bone hole, to thereby reside within the cancellous bone and under the bone cortex. One such suture anchor is disclosed in U.S. Pat. No. 9,826,971 assigned to the assignee hereof and incorporated by reference herein in its entirety. Since soft anchors are commonly made entirely of suture materials, they are sometimes called "all-suture" anchors, and generally include a fibrous construct anchor body portion (or fibrous, braided or woven fabric-type structure such as a flexible web, as described in U.S. Pat. No. 9,173,652) and a suture or filament portion. Methods and devices for inserting/deploying such all-suture anchors are known, examples of which are disclosed in U.S. Pat. No. 9,173,652.

As described in U.S. Pat. No. 8,409,252, for example, "non-soft," "hard" or "rigid" suture anchors generally include a "hard" anchor body portion (that may or may not include inner and outer members) and a suture/filament portion. The anchor body of such suture anchors may be formed of a biocompatible and/or bioabsorbable material. These materials may be of such composition that they are reabsorbed by the body, e.g., during the healing process of the bone. Exemplary materials that are suitable for use in the inner and outer members include, but are not limited to, polyetheretherketone ("PEEK"), polylactic acid/beta-tricalcium phosphate ("PLA/Beta-TCP") composites, ultra-high molecular weight polyethylene ("UHMWPE"), as well as other metallic, non-metallic, and polymeric materials.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which:

FIG. 6B is a cross-sectional view schematic representation of the inserter tip of FIG. 6A;

FIG. 9A is a top perspective view schematic representation of the quick change connector, according to an alternative embodiment;

FIG. 9B is a side view schematic representation of the quick change connector of FIG. 9A;

FIG. 11A is a back view schematic representation of an all-suture anchor, according to an embodiment;

FIG. 13B is a side view schematic representation of the all-suture anchor loaded onto the inserter tip of FIG. 13A;

FIG. 14A is a top view schematic representation of an all-suture anchor loaded onto the inserter tip, according to an alternative embodiment;

FIG. 14B is a side view schematic representation of the all-suture anchor loaded onto the inserter tip of FIG. 14A;

FIG. 15 is a side view schematic representation of an all-suture anchor loaded onto the inserter tip with the anchor deployment passage in a closed position, according to an embodiment;

Figure 1:
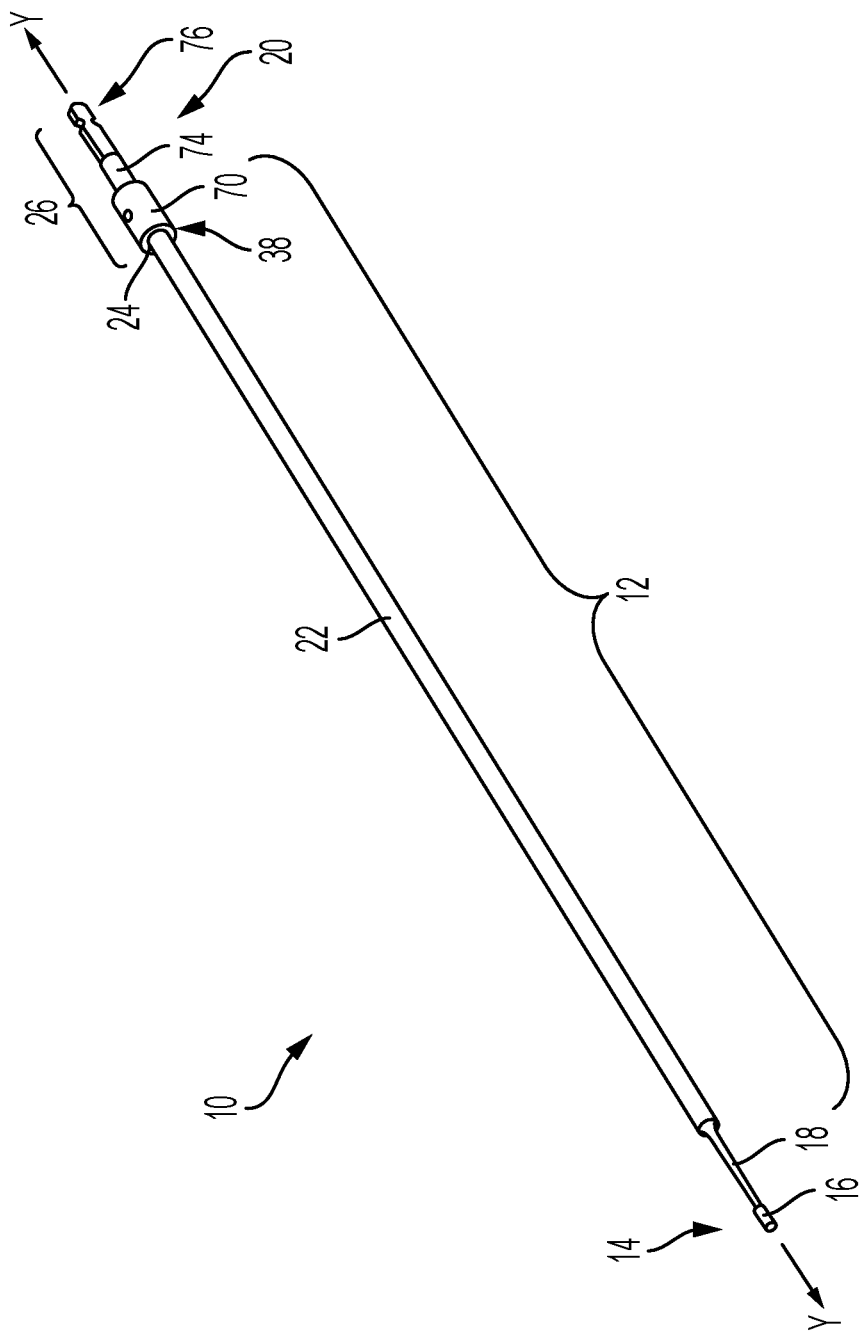
FIG. 1 is a perspective view schematic representation of an inserter in the unloaded, pre-deployment configuration.
Figure 17A:
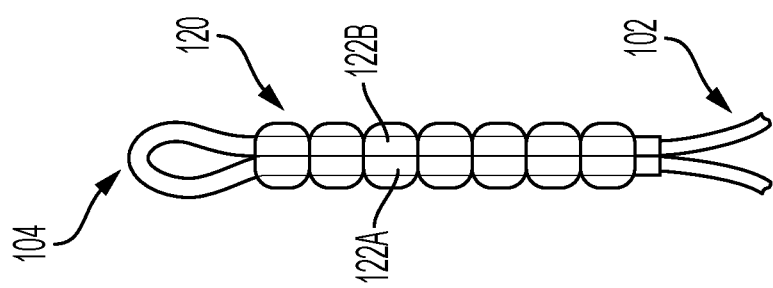
FIG. 17A is a top view schematic representation of an anchor braid folded and stitched, according to an embodiment.
Figure 18:
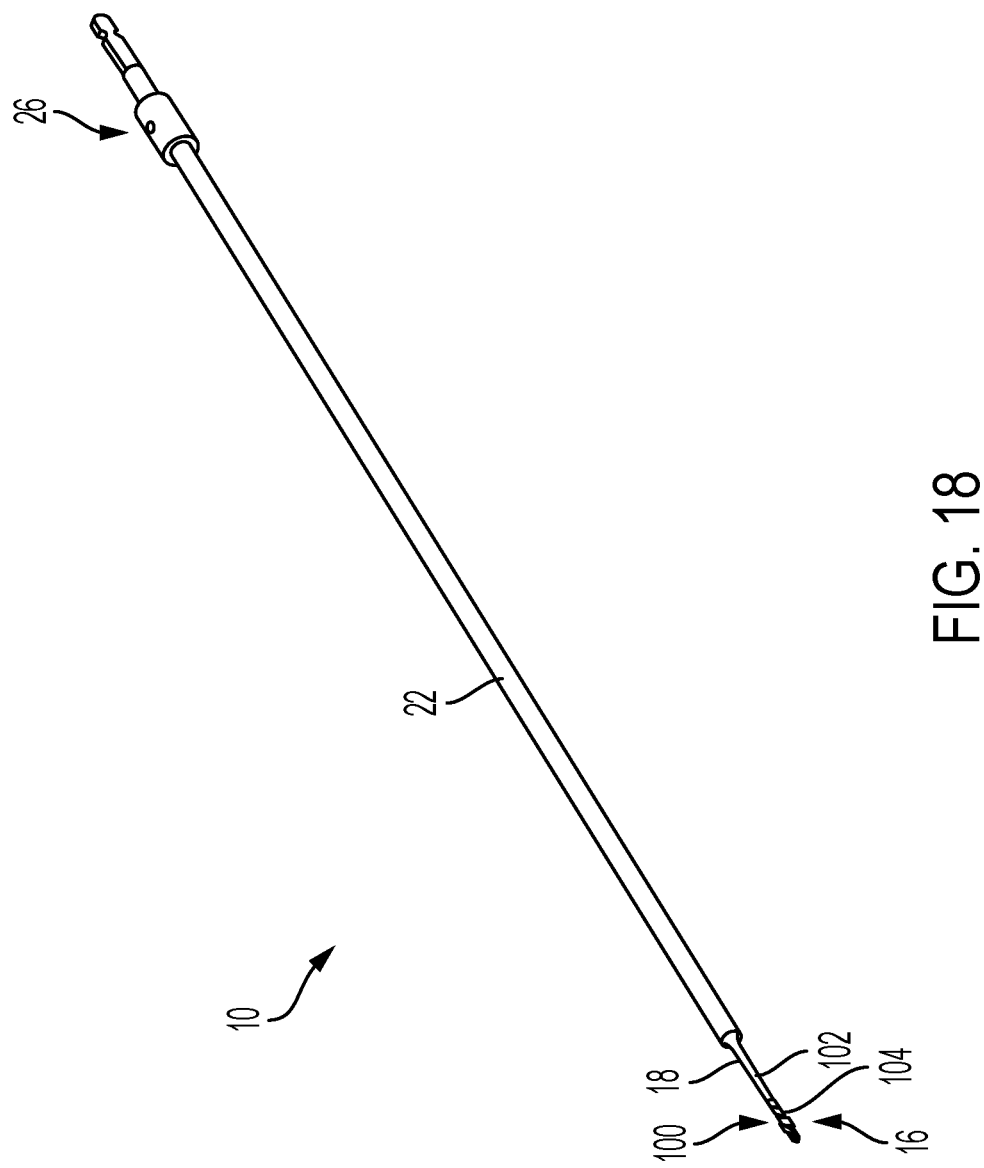
Figure 19:
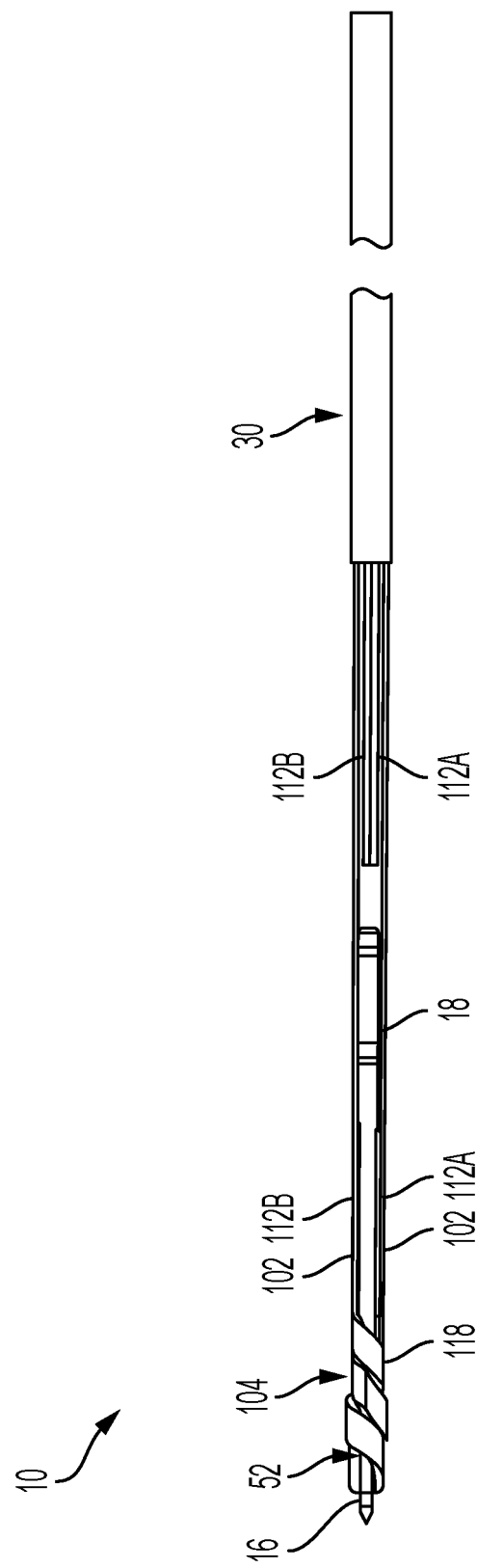
Figure 20:
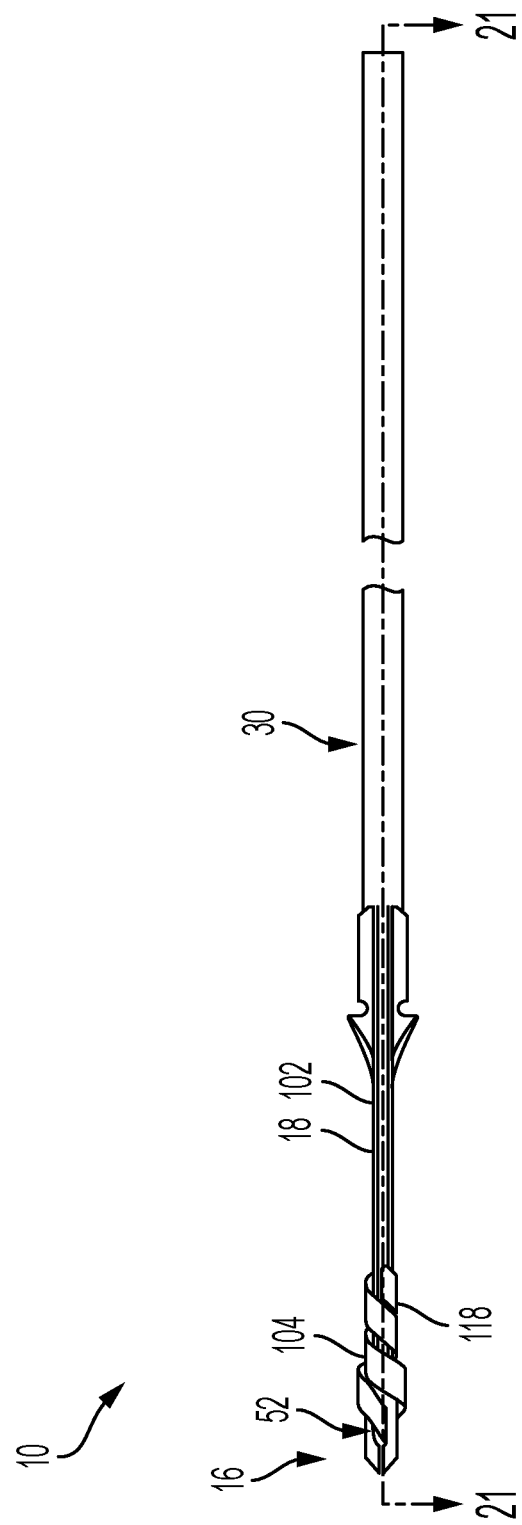
Figure 21:
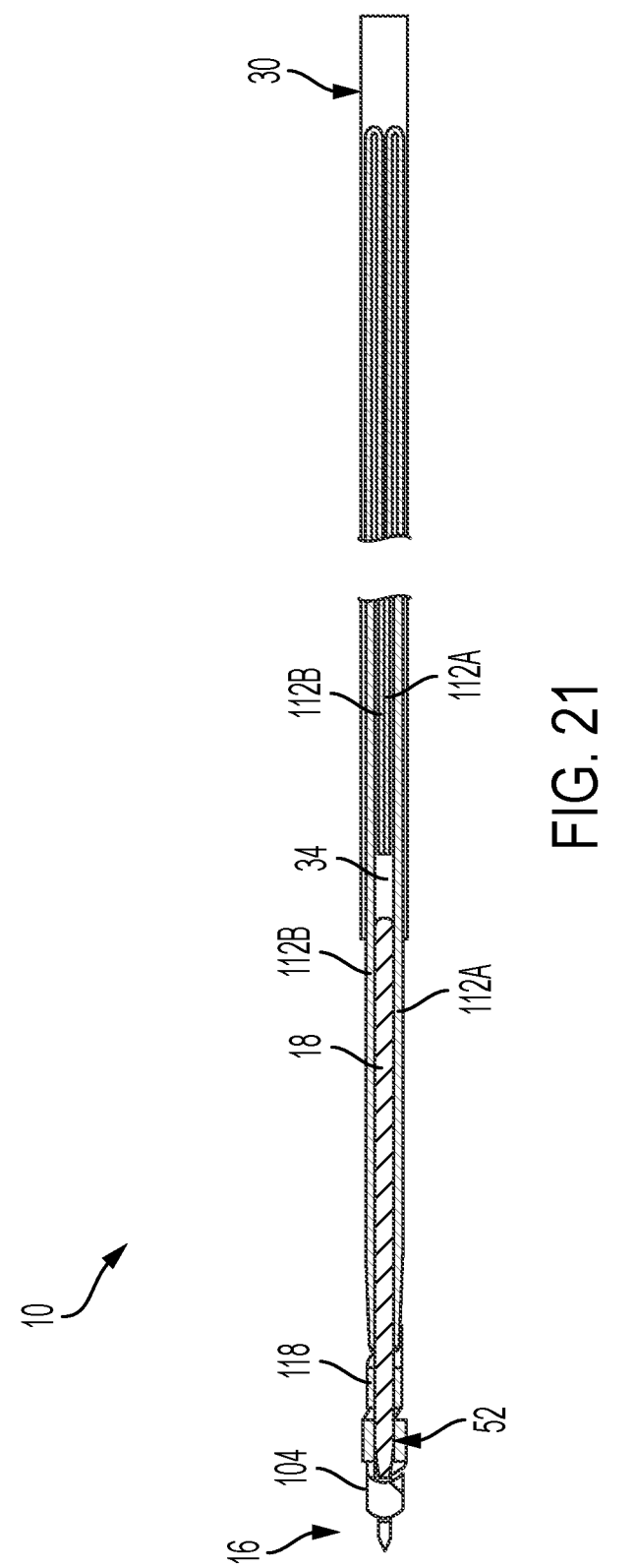
Figure 22:
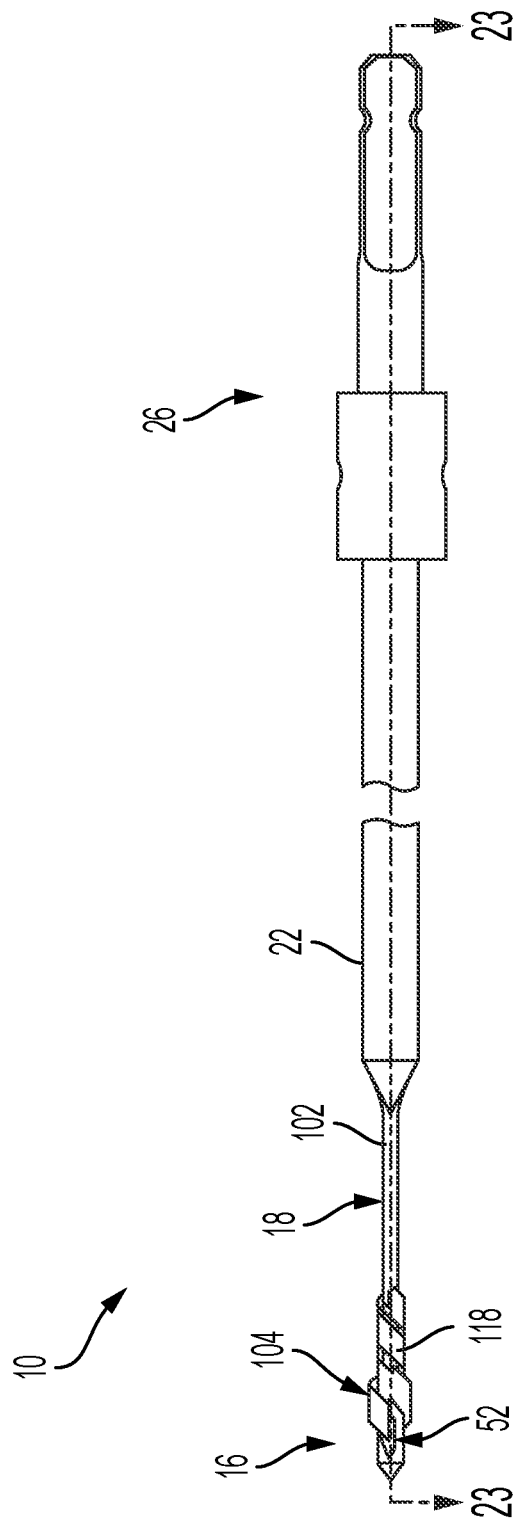
Figure 23:
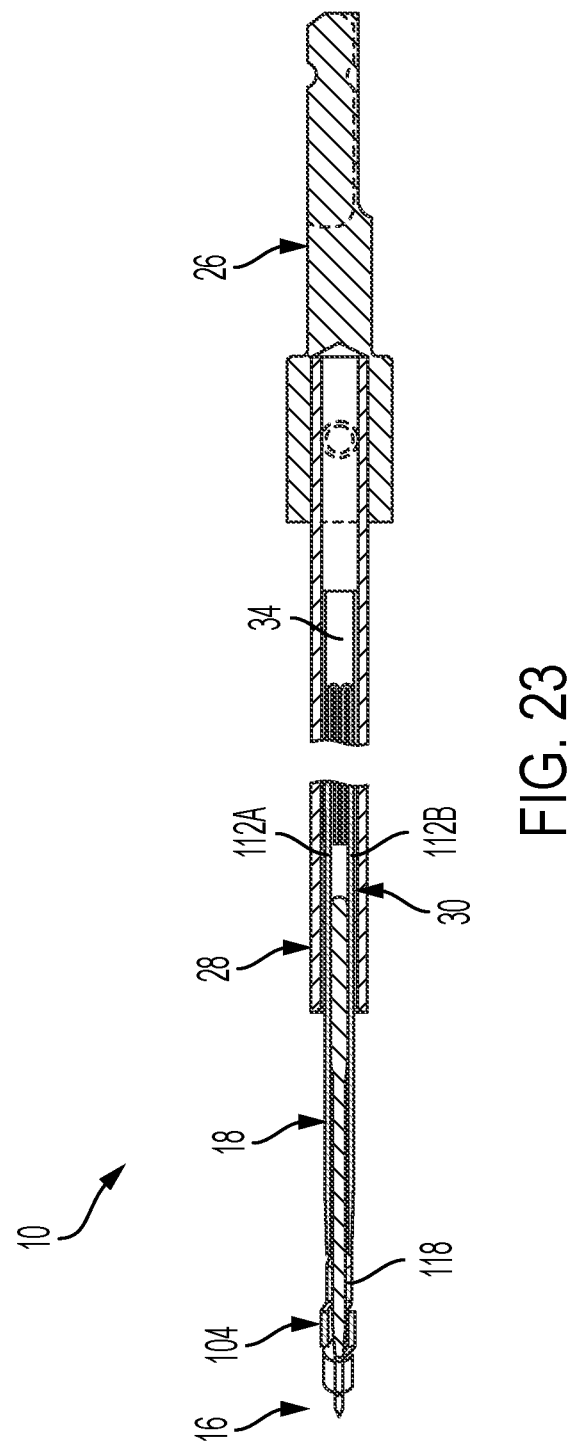
Figure 24:
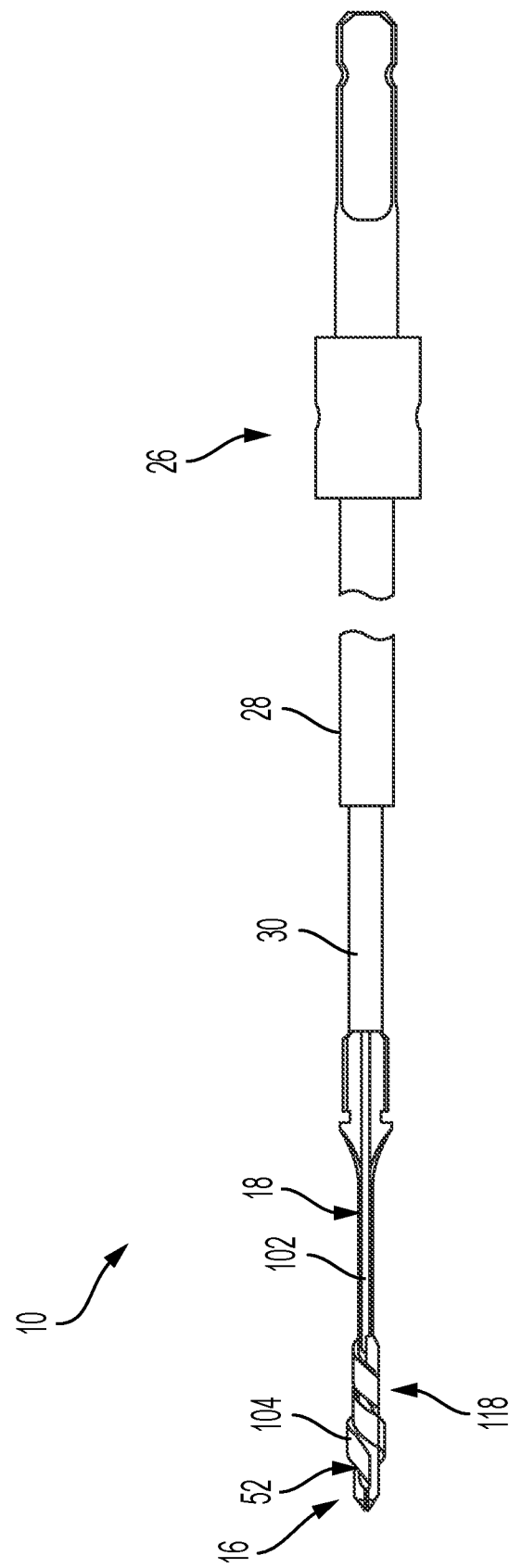
Figure 25:
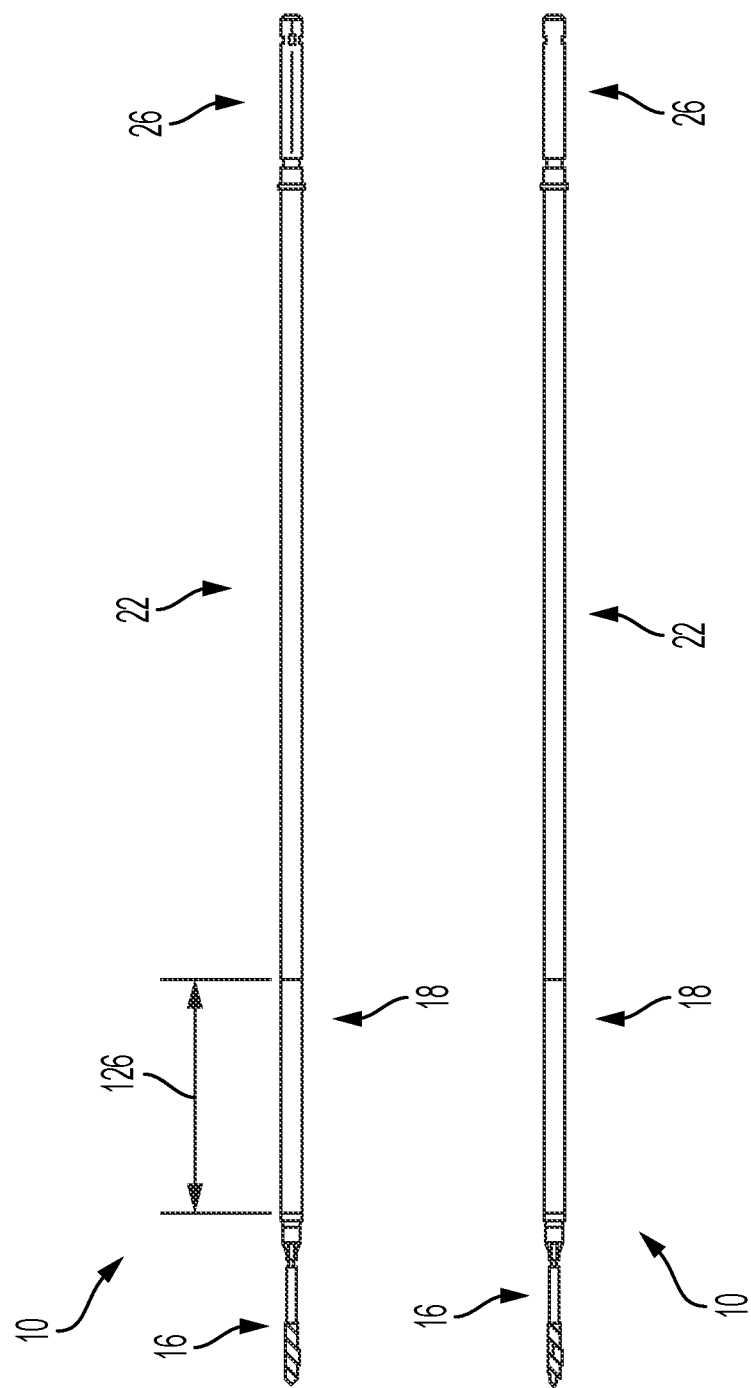
Figure 26:
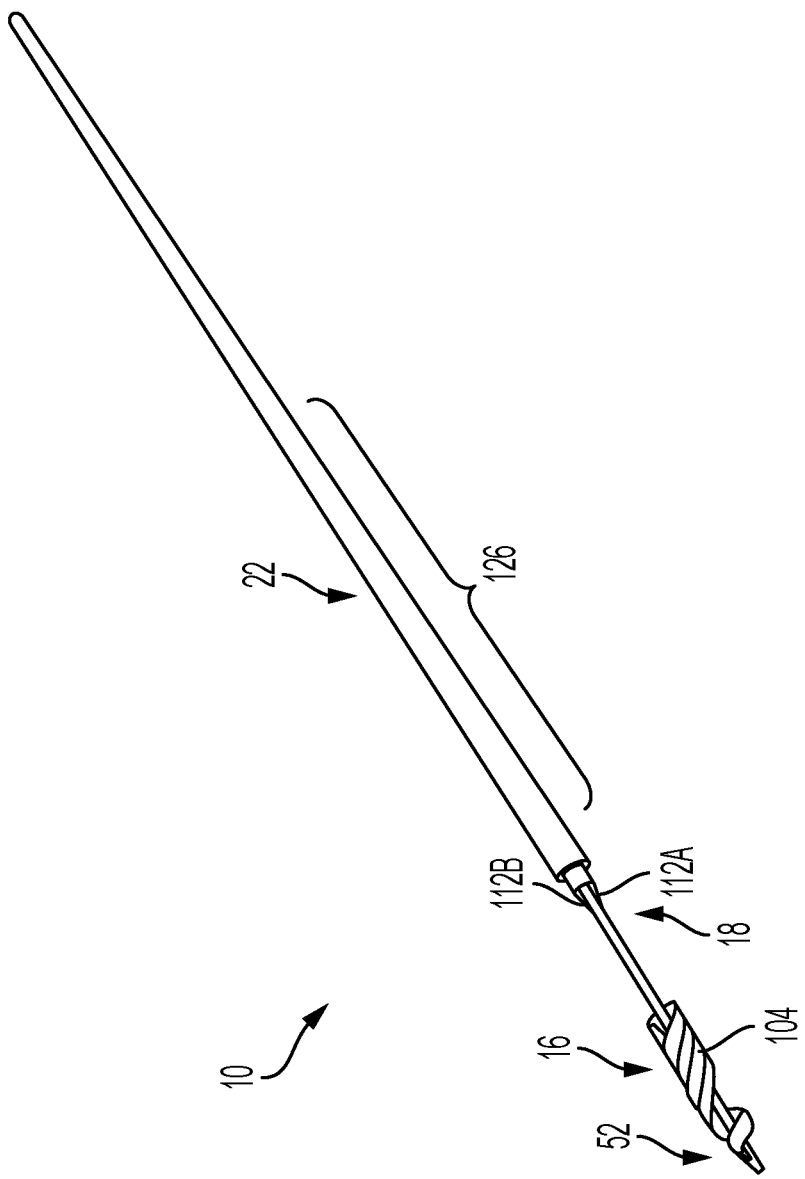
Figure 27:
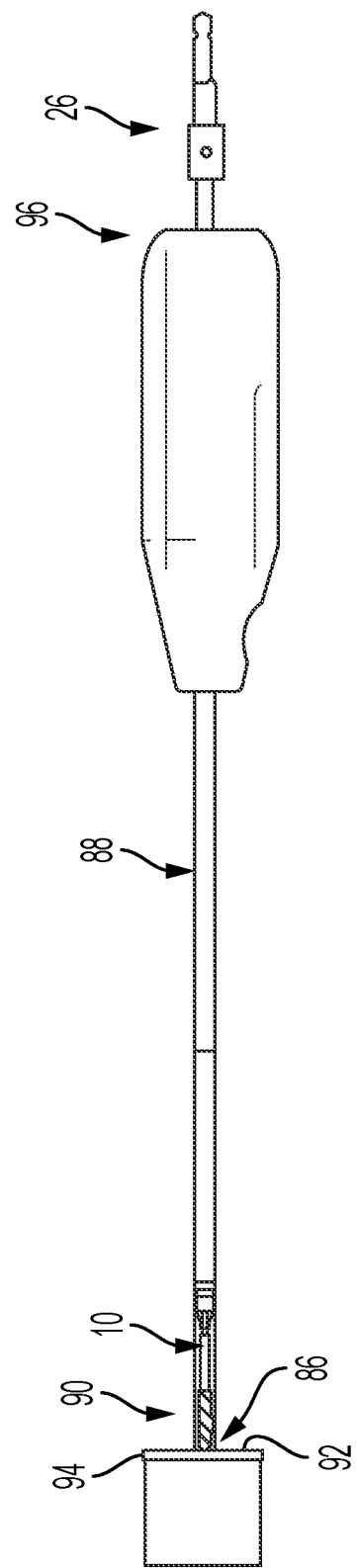
Figure 28:
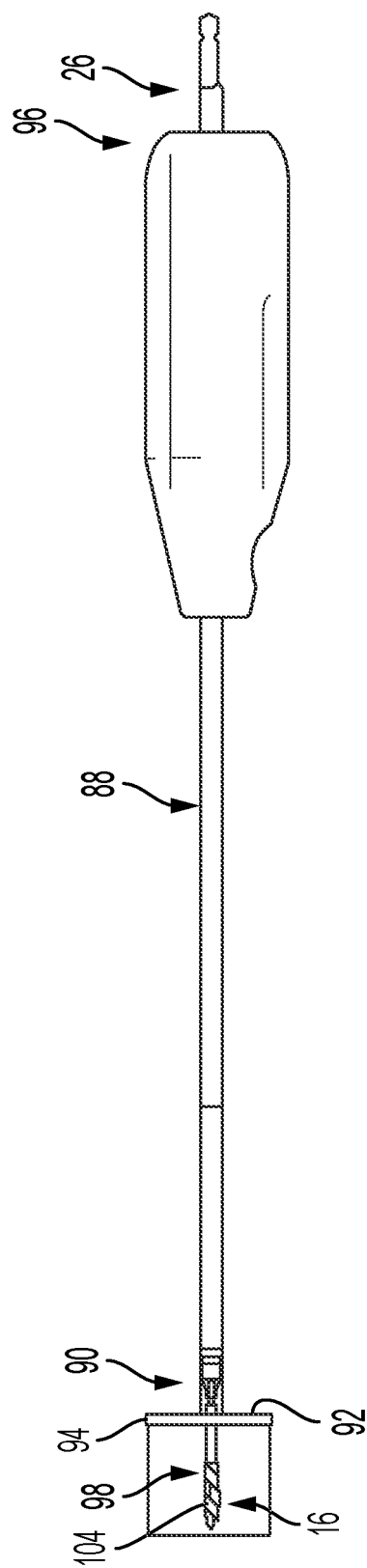
Figure 30A:
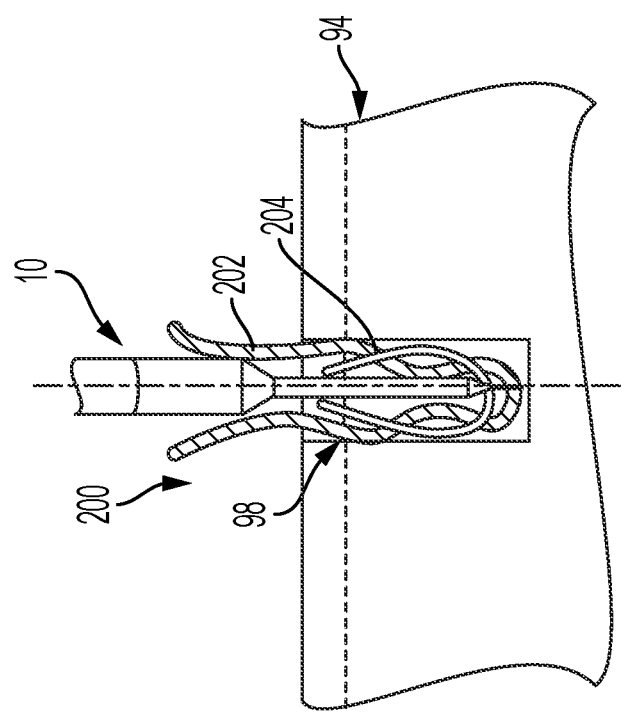
Figure 30B:
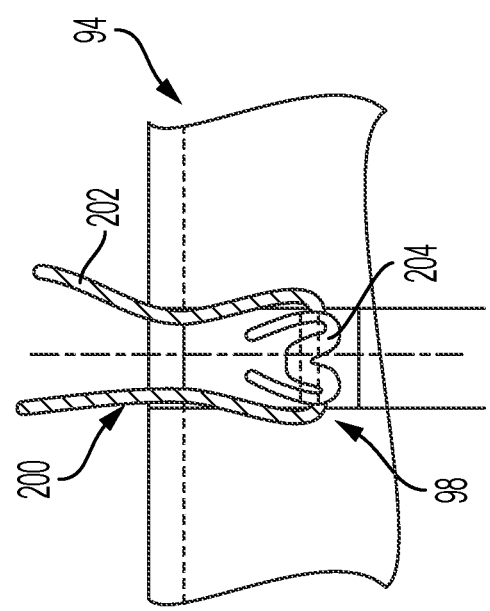
Figure 31:
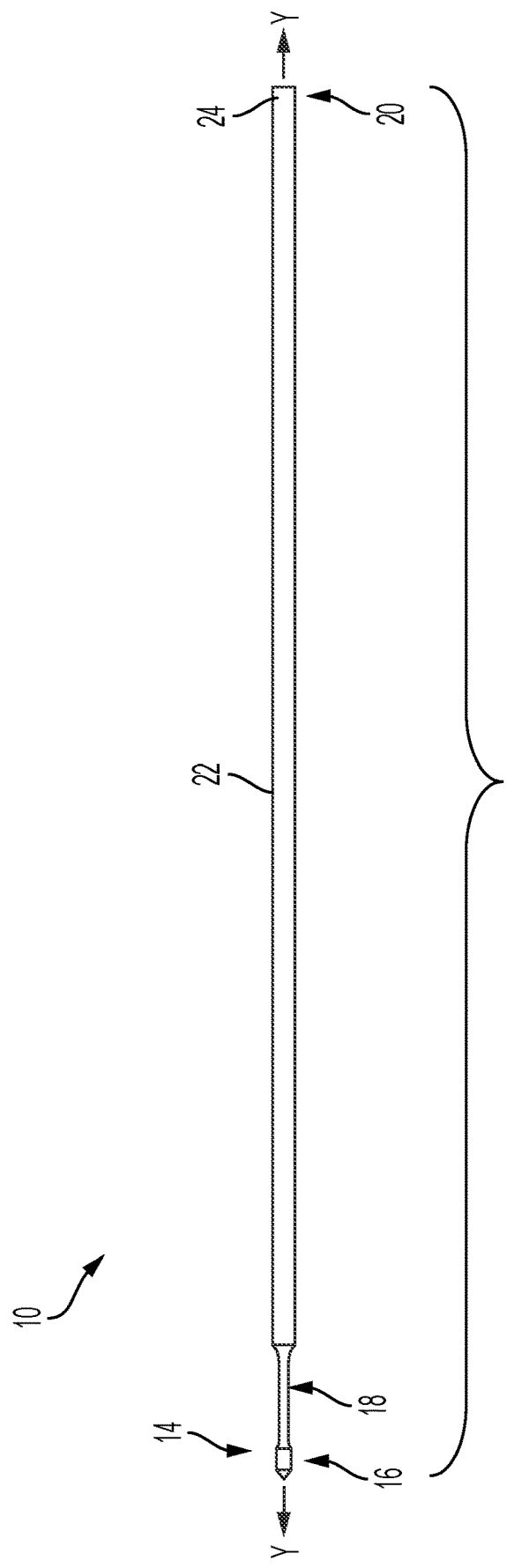
Figure 32:
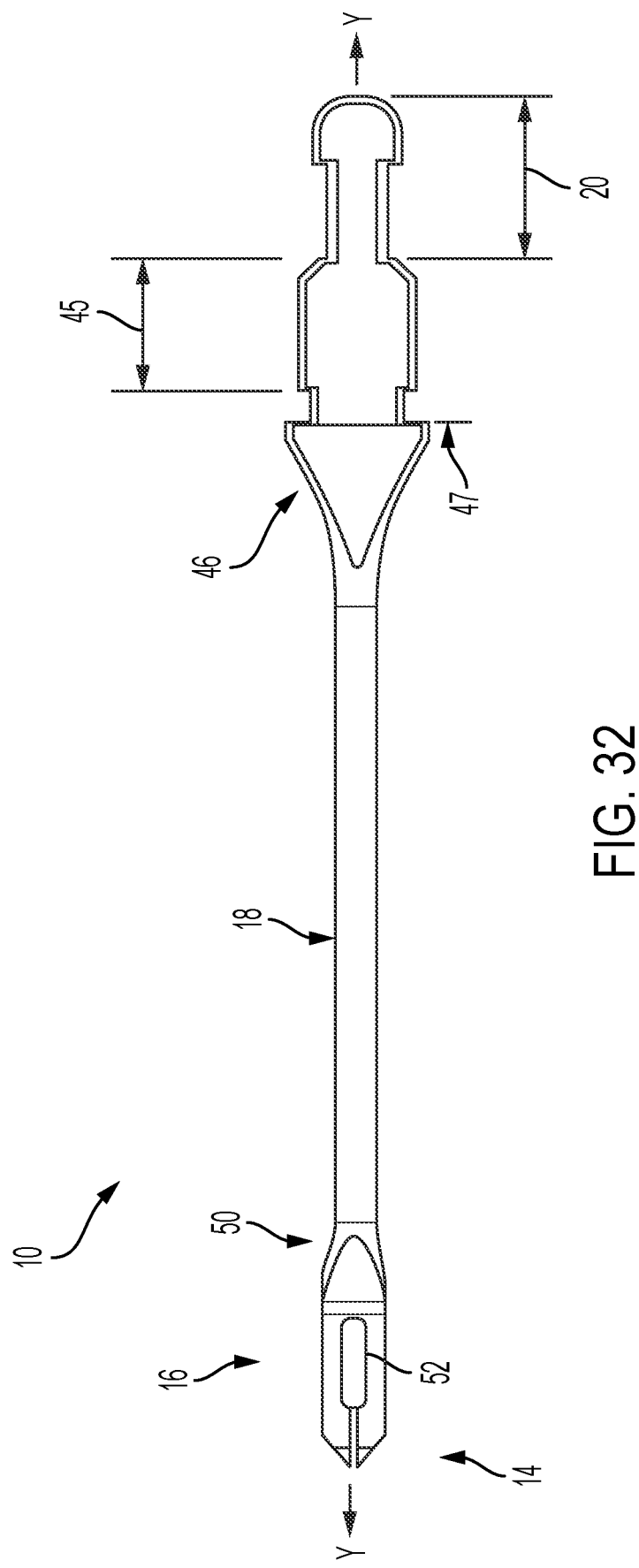
Figure 33:
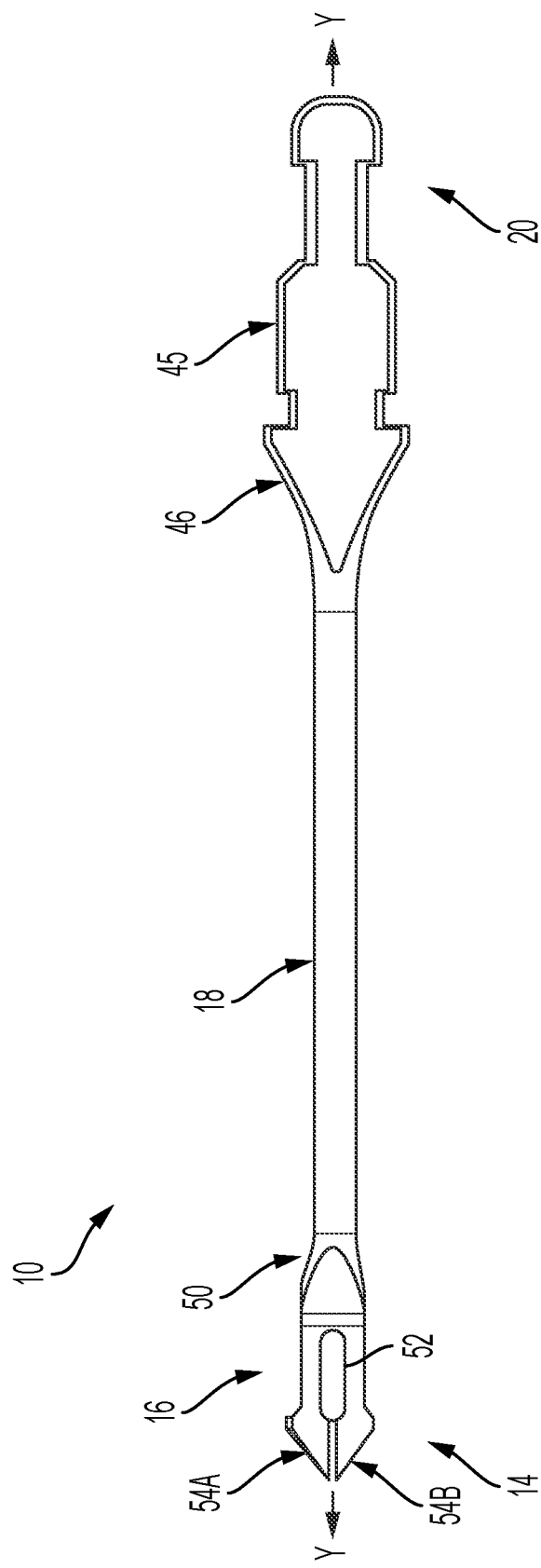
Figure 34:
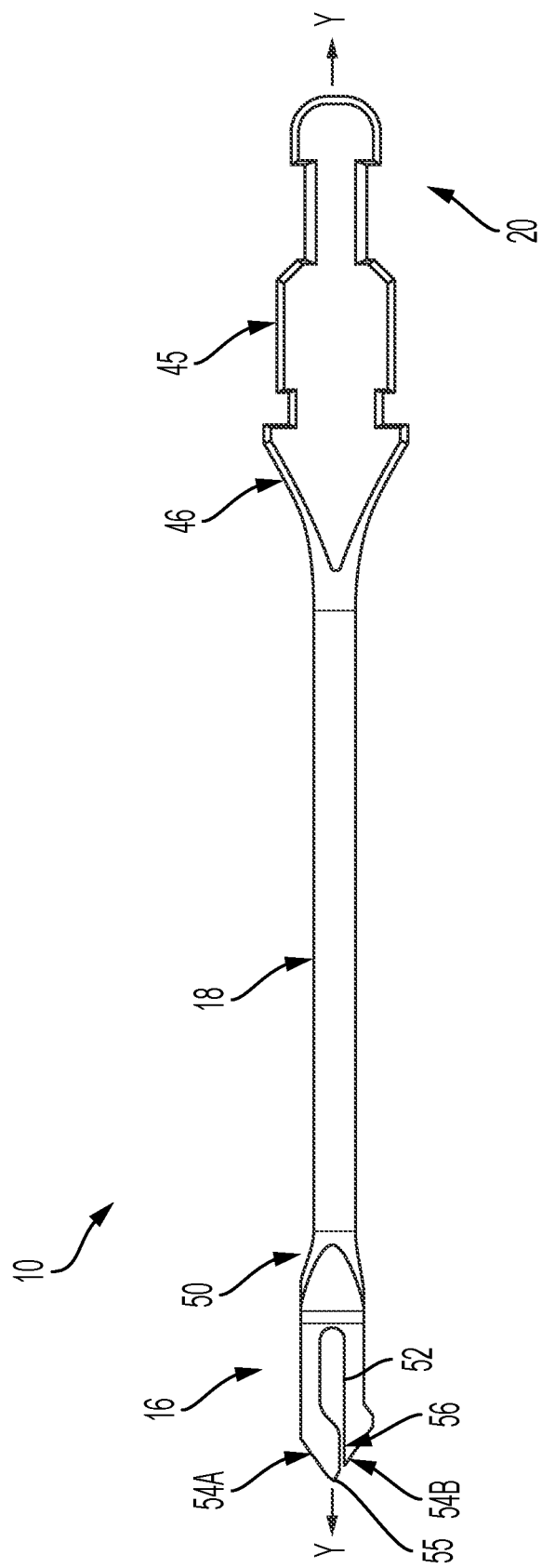
Figure 35:
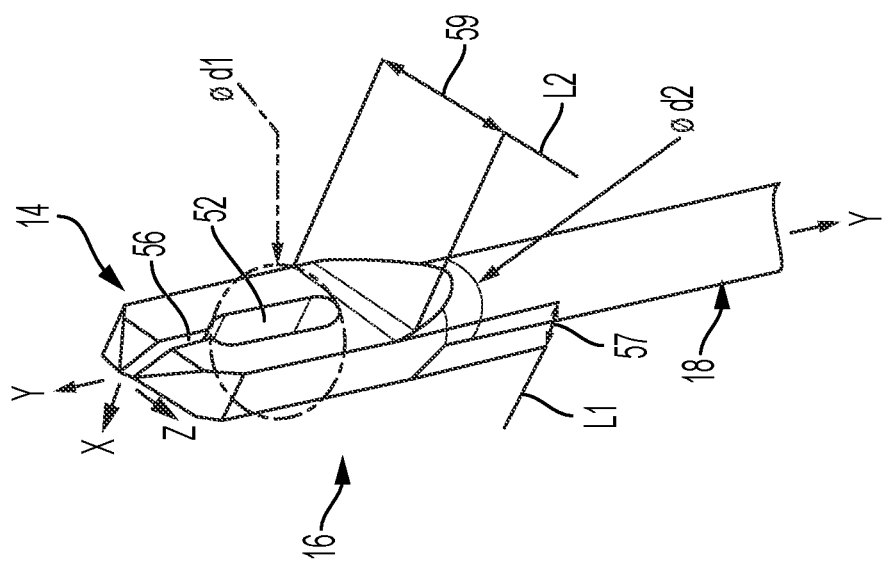
Figure 36A:
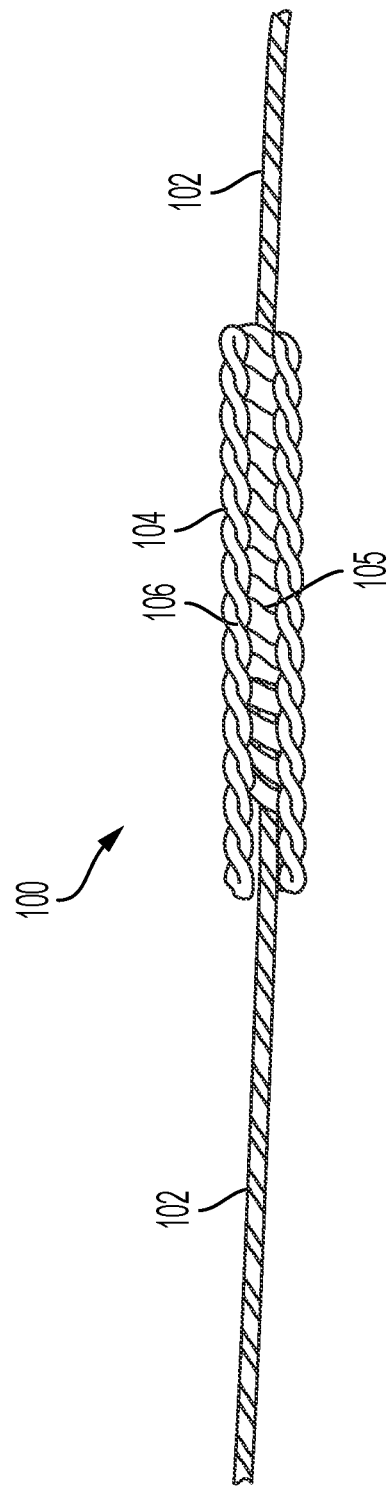
Figure 36B:
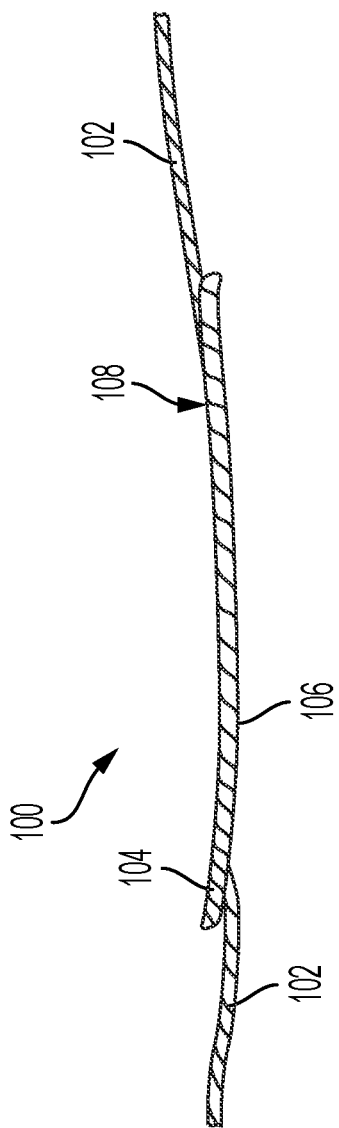
Figure 37B:
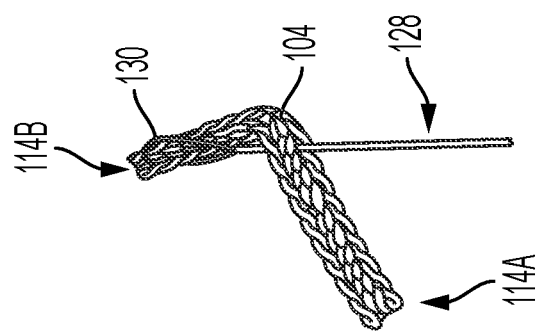
Figure 37C:
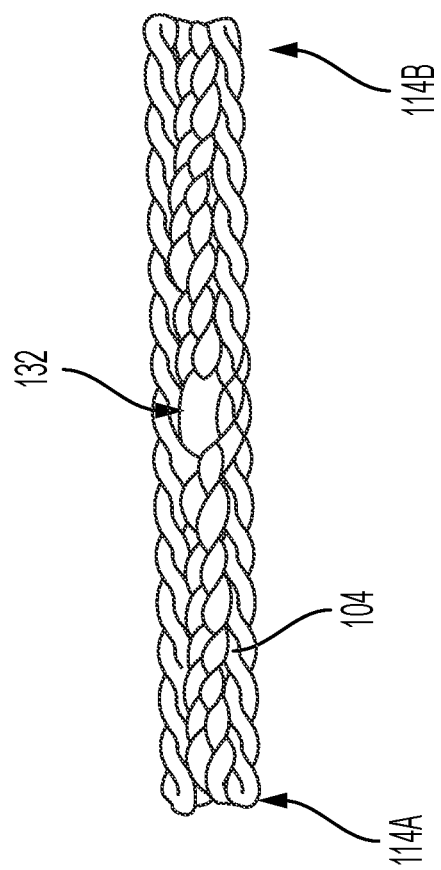
Figure 38:
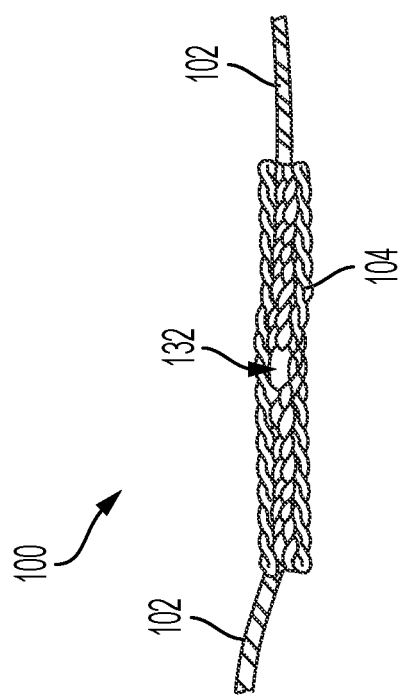
Figure 39A:
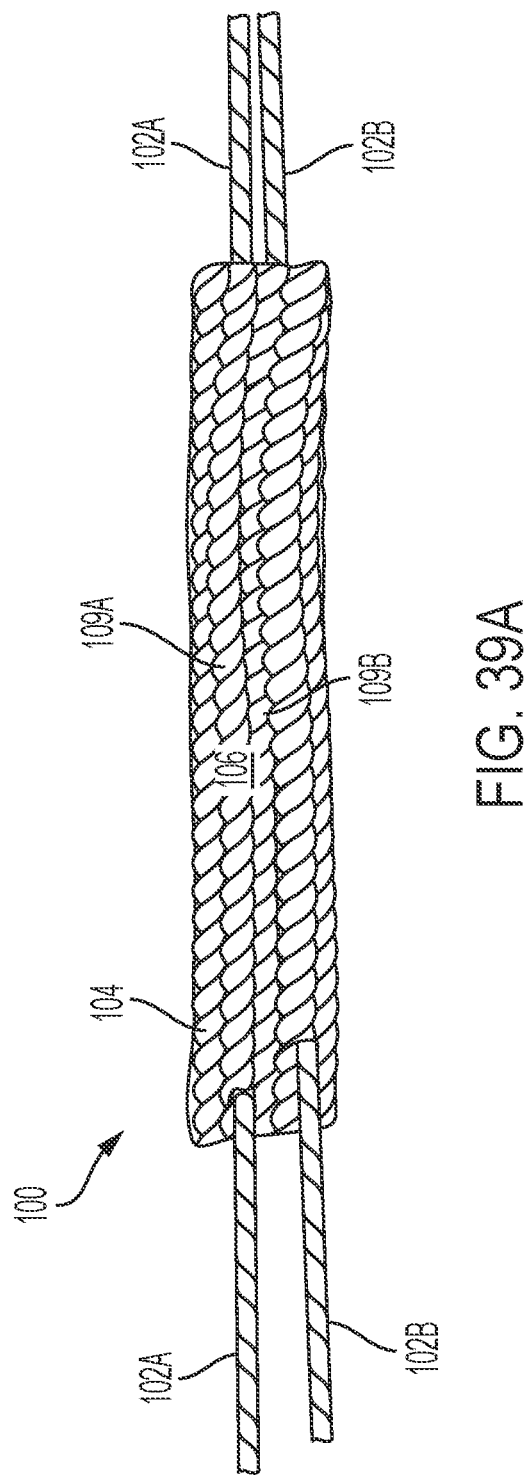
Figure 39B:
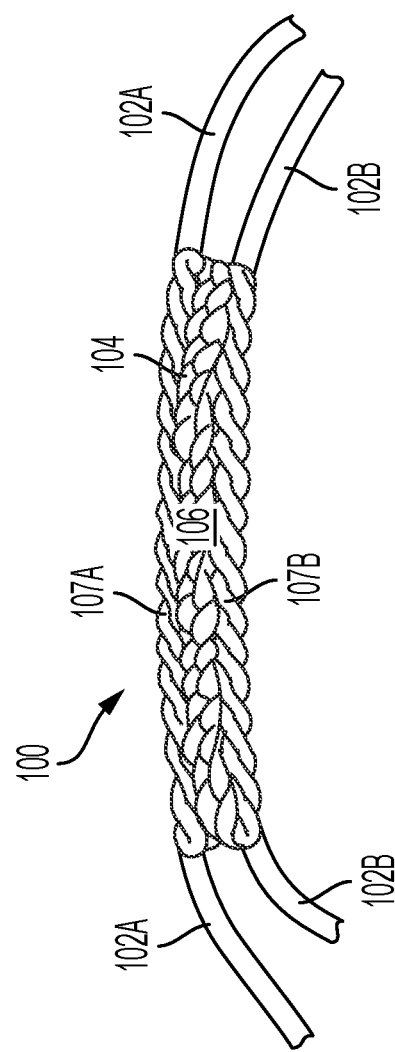
Figure 41:
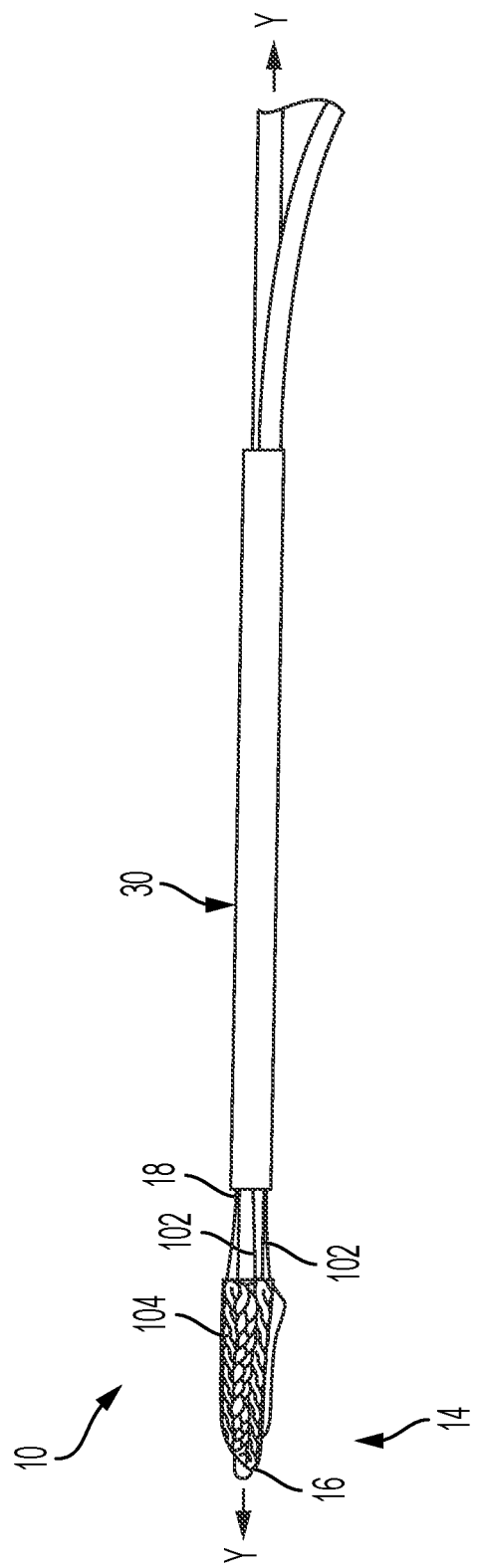
Figure 42:
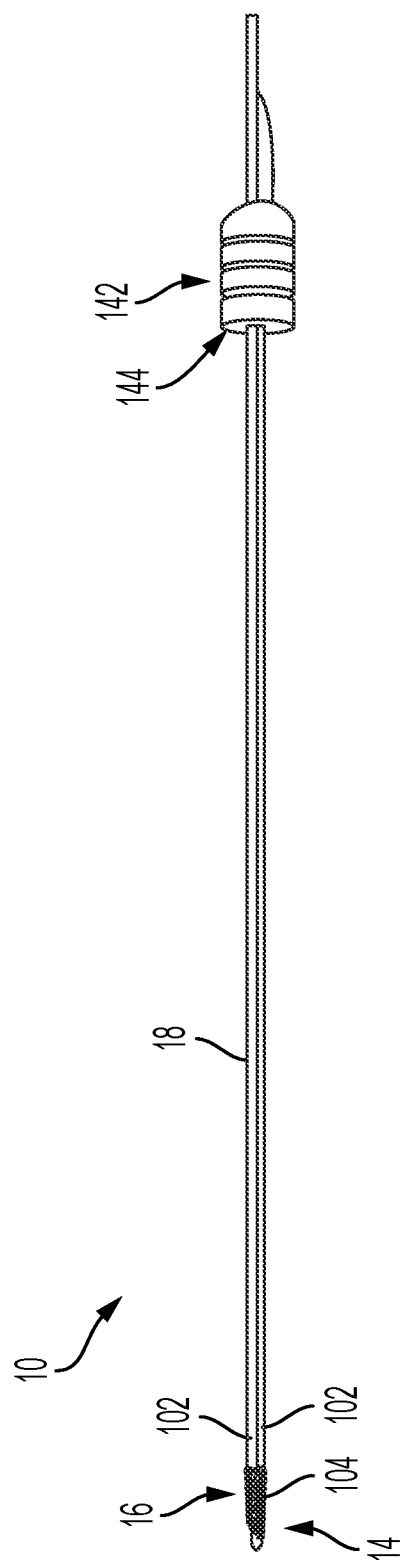
Figure 43:
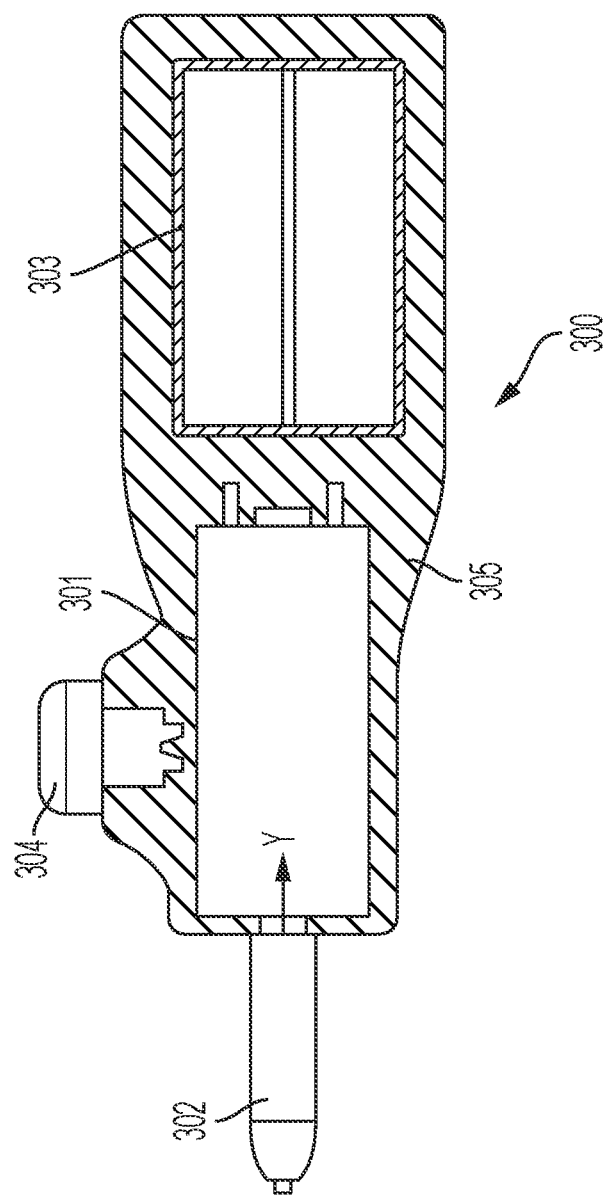
Figure 44:
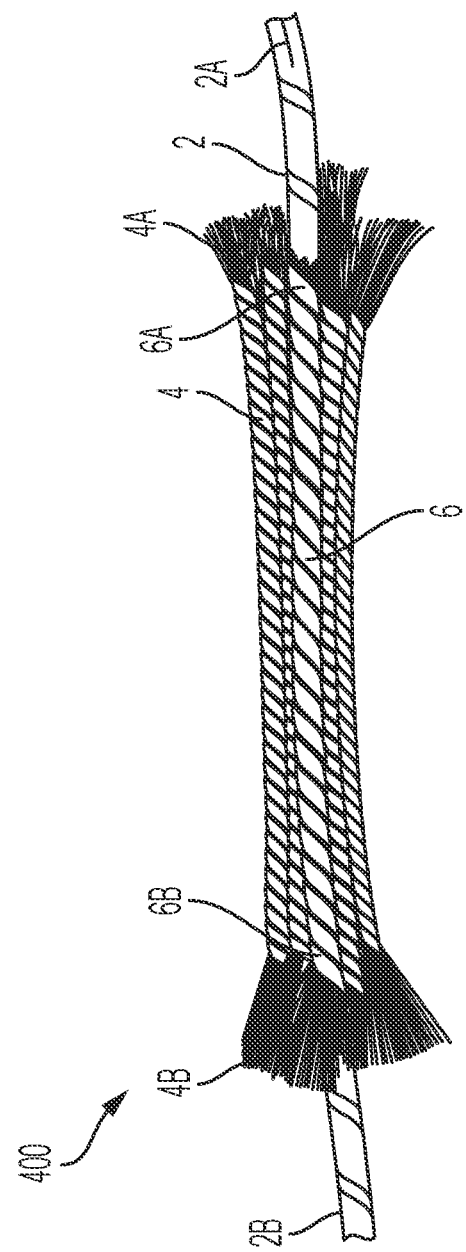
Figure 45B:
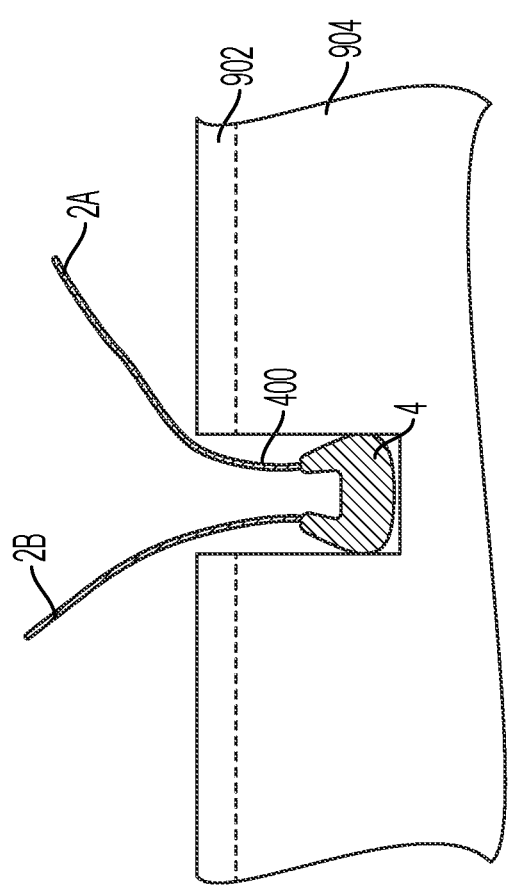
Figure 45C:
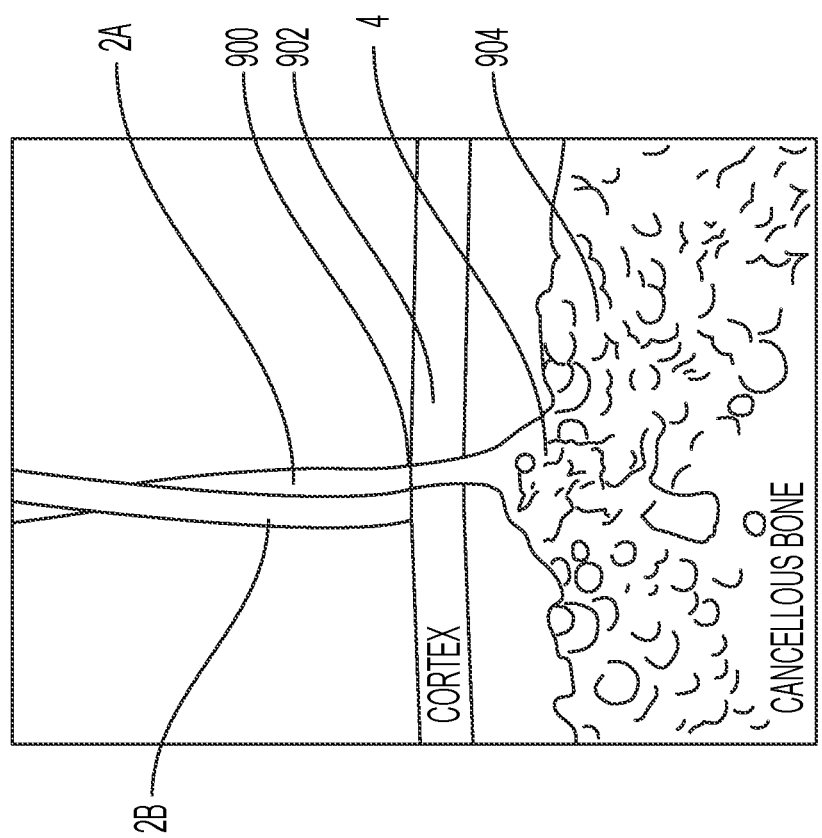
Figure 46:
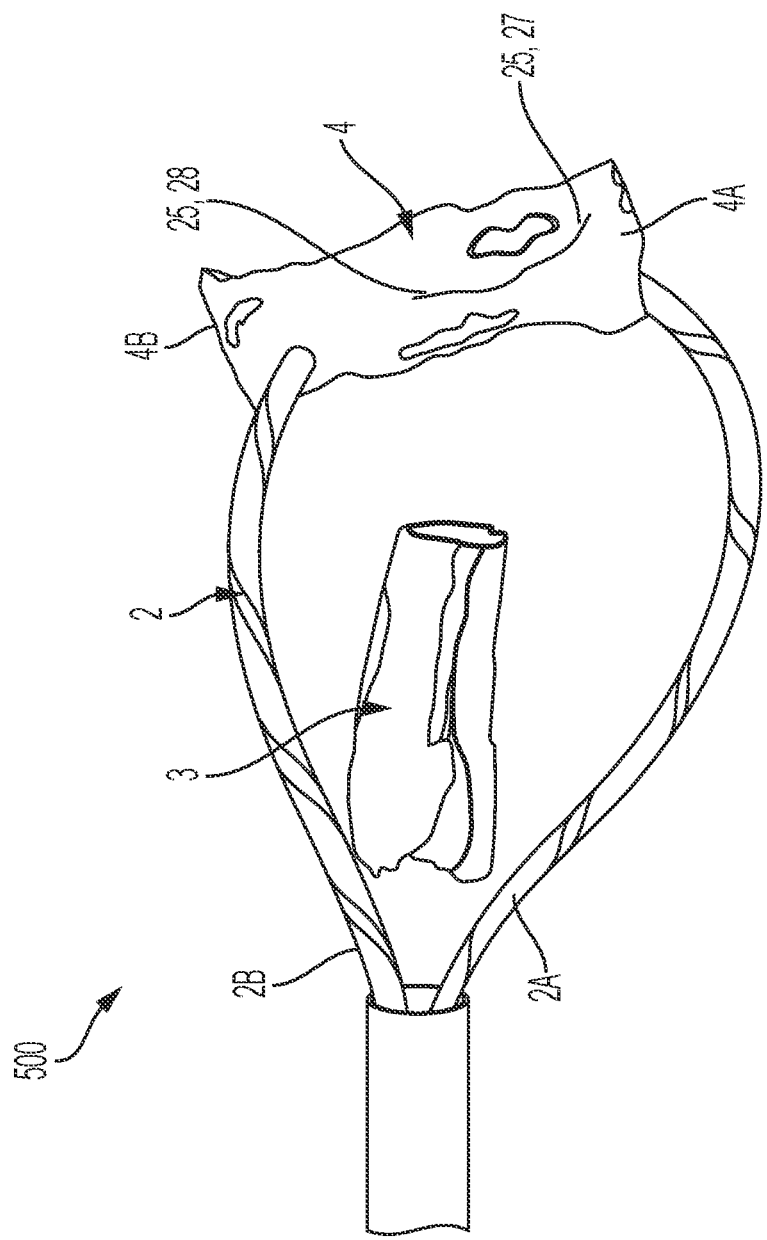
Figure 47A:
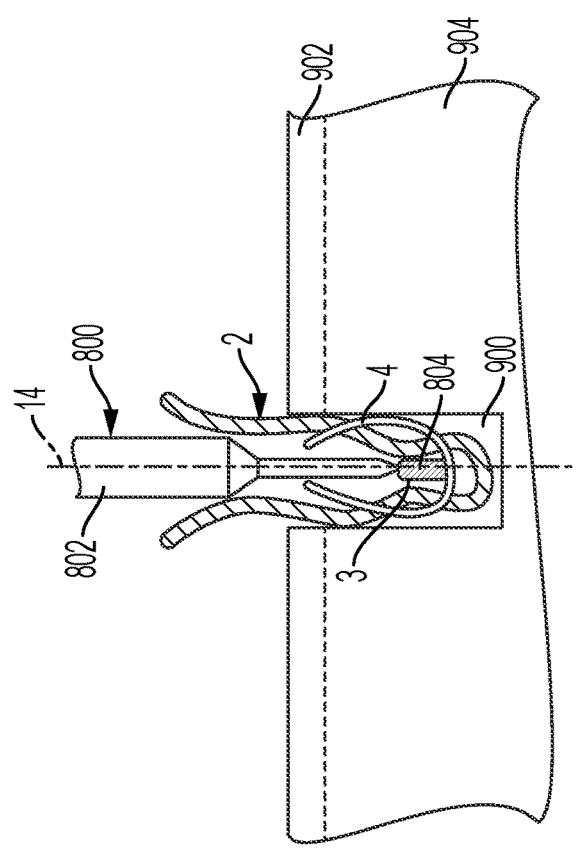
Figure 47B:
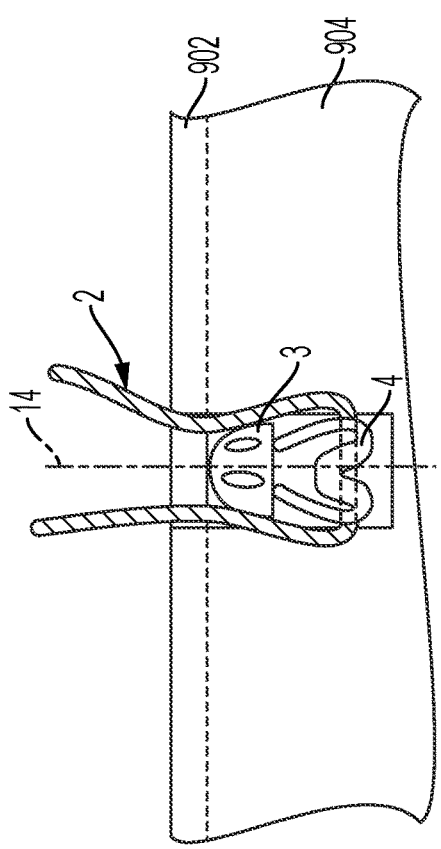
Figure 47C:
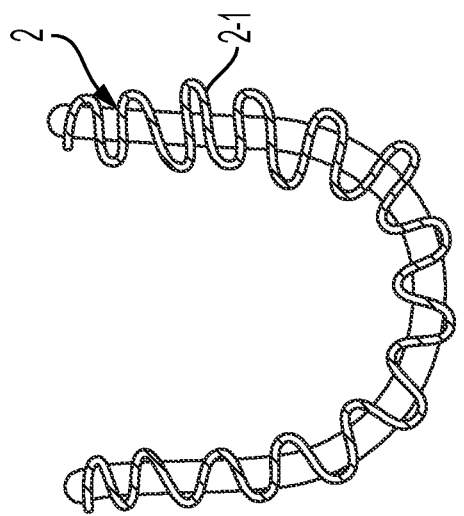
Figure 48:
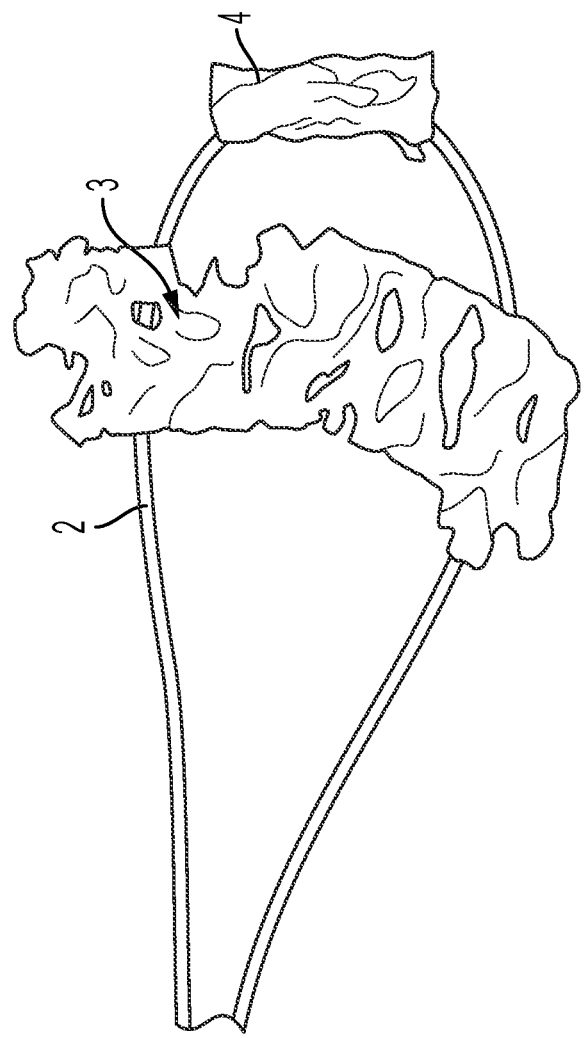
Figure 49:
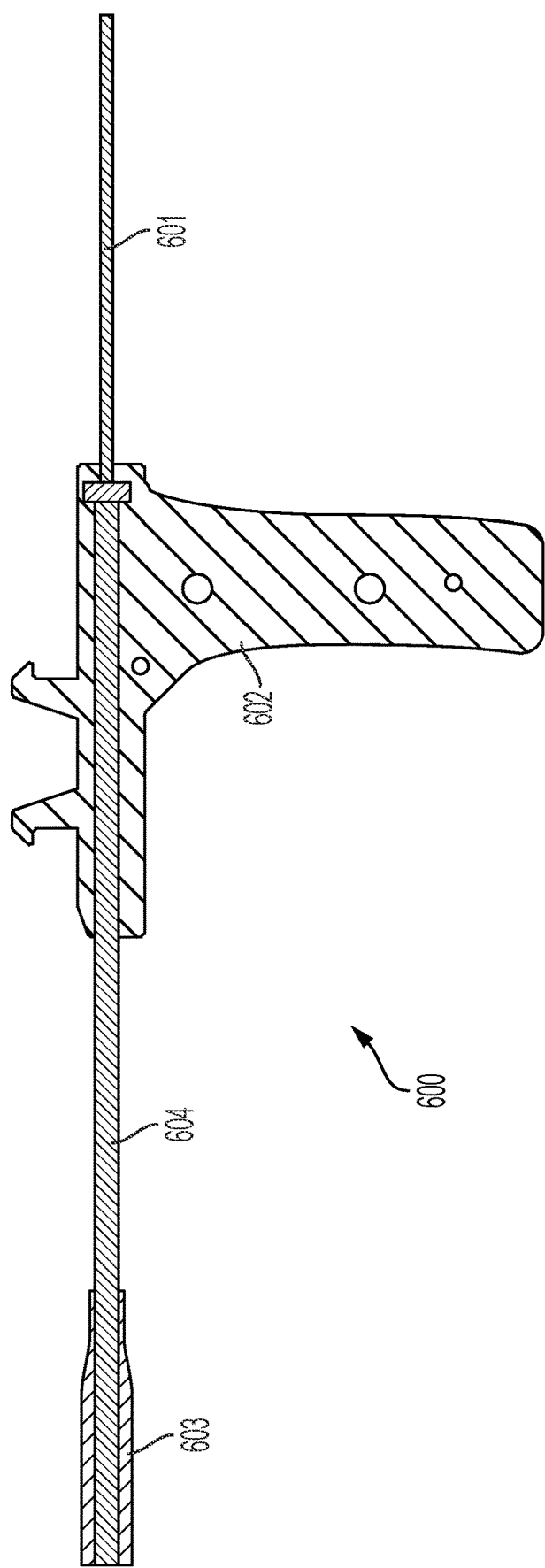
Figure 50:
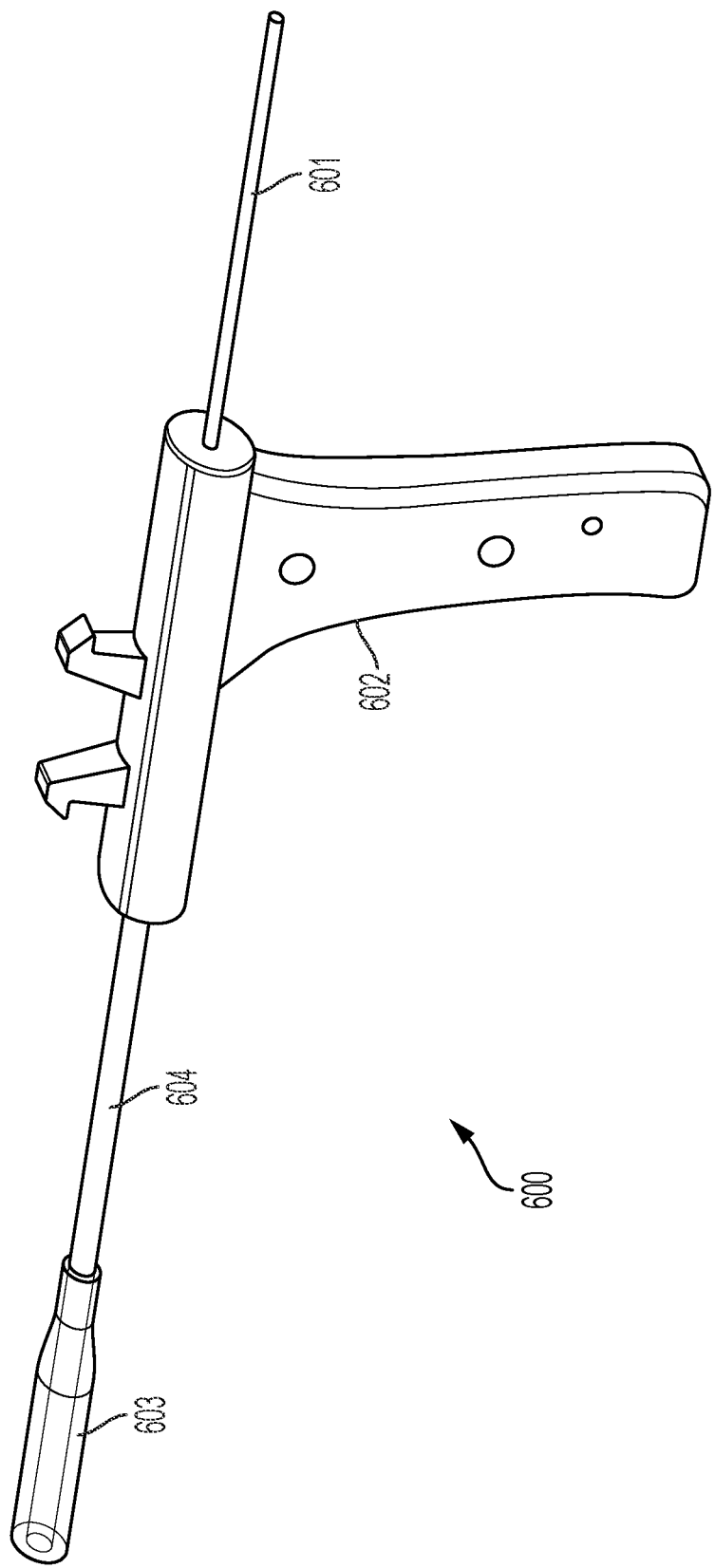
Figure 51:
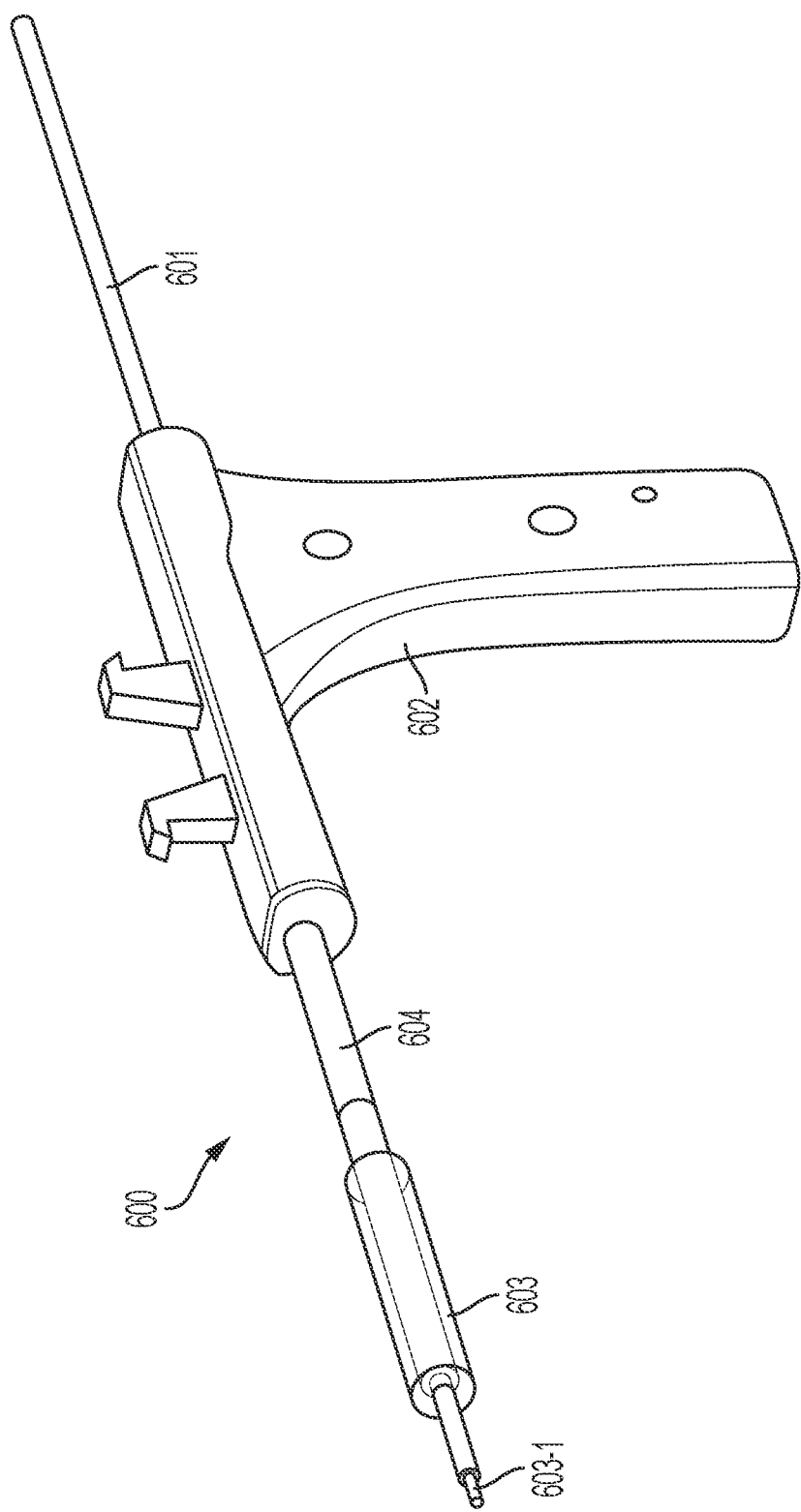

FIG. 17B a top view schematic representation of an anchor braid of FIG. 17A with an additional material covering;

FIG. 18 is a perspective view schematic representation of the inserter in the loaded, pre-deployment configuration, according to an embodiment;

FIG. 19 is a side view schematic representation of the inserter in the loaded, pre-deployment configuration with components removed, according to the embodiment;

FIG. 20 is a top view schematic representation of the inserter in the loaded, pre-deployment configuration with components removed, according to the embodiment;

FIG. 21 is a cross-sectional schematic representation of the inserter of FIG. 20;

FIG. 22 is a top view schematic representation of the inserter in the loaded, pre-deployment configuration, according to an embodiment;

FIG. 23 is a cross-sectional view schematic representation of the inserter of FIG. 22;

FIG. 24 is a top view schematic representation of the inserter in the loaded, pre-deployment configuration, according to an embodiment;

FIG. 25 is a top view and side view schematic representation of the inserter in the loaded, pre-deployment configuration, according to an alternative embodiment;

FIG. 26 is a perspective view schematic representation of the inserter in the loaded, pre-deployment configuration, according to an alternative embodiment;

FIG. 27 is a side view schematic representation of the inserter in the loaded, pre-deployment configuration at a bone hole location, according to an embodiment;

FIG. 28 is a side view schematic representation of the inserter in the loaded, pre-deployment configuration in a bone hole, according to an embodiment;

FIG. 29 is a side view schematic representation of the inserter in the unloaded, post-deployment configuration, according to an embodiment;

FIG. 30A is a side view schematic representation of an embodiment of a suture anchor in the undeployed state, according to an embodiment;

FIG. 30B is a side view schematic representation of the suture anchor of FIG. 30A shortened and expanded in the deployed state, according to an embodiment;

FIG. 31 is a top view schematic representation of the inserter in the unloaded, pre-deployment configuration without a quick change connector, according to an embodiment;

FIG. 32 is another top view schematic representation of the inserter in the unloaded, pre-deployment configuration, according to an embodiment;

FIG. 33 is a top view schematic representation of the inserter in the unloaded, pre-deployment configuration, according to an alternative embodiment;

FIG. 34 is a top view schematic representation of the inserter in the unloaded, pre-deployment configuration, according to an additional alternative embodiment;

FIG. 35 is a close-up perspective view schematic representation of the distal end of the inserter, according to an embodiment;

FIG. 36A is a top view schematic representation of an all-suture anchor, according to an embodiment;

FIG. 36B is a side view schematic representation of the all-suture anchor in FIG. 36A;

FIG. 37A is a top view schematic representation of a threader passed through an anchor braid, according to an embodiment;

FIG. 37B is a top view schematic representation of the anchor braid of FIG. 37A with a first end loaded into the threader;

FIG. 37C is a top view schematic representation of the anchor braid of FIG. 37A with a central eyelet;

FIG. 38 is a top view schematic representation of the anchor braid of FIG. 37C with a length of suture passing through the central eyelet;

FIG. 39A is a top view schematic representation of an anchor braid loaded with two lengths of suture, according to an embodiment;

FIG. 39B is a top view schematic representation of an anchor braid loaded with two lengths of suture, according to an alternative embodiment;

FIG. 40A is a side view schematic representation of a cleat component, according to an embodiment;

FIG. 40B is a side view schematic representation of a cleat component with a suture slot, according to an embodiment;

FIG. 41 is a top view schematic representation of the inserter in the loaded, pre-deployment configuration, according to an embodiment;

FIG. 42 is a top view schematic representation of the inserter in the loaded, pre-deployment configuration with a sleeve, according to an embodiment;

FIG. 43 is a side view schematic representation of a disposable handpiece with a according to an embodiment;

FIG. 44 is a perspective view digital photograph of a soft all-suture anchor in an unloaded (not loaded onto an installation device or inserter), pre-deployment configuration according to an embodiment;

FIG. 45A is a side view schematic representation of an embodiment of the all-suture anchor of FIG. 44 connected to an installation device or inserter in a pre-deployment configuration according to an embodiment FIG. 45B is a side view schematic representation of an embodiment of the all-suture anchor of FIG. 44 in a post-deployment configuration positioned in a bone hole according to an embodiment;

FIG. 45C is a side view digital photograph of an embodiment of the all-suture anchor of FIG. 1 in a post-deployment configuration positioned in a bone hole according to an embodiment;

FIG. 46 is a perspective view digital photograph of a soft all-suture anchor in an unloaded (not loaded onto an installation device or inserter), pre-deployment configuration according to an embodiment;

FIG. 47A is a side view schematic representation of an embodiment of the all-suture anchor of FIG. 46 connected to an installation device or inserter in a pre-deployment configuration according to an embodiment;

FIG. 47B is a side view schematic representation of an embodiment of the all-suture anchor of FIG. 46 in a post-deployment configuration positioned in a bone hole according to an embodiment;

FIG. 47C is a side view schematic representation of a portion of an alternative embodiment of the all-suture anchor according to an embodiment;

FIG. 48 is a side view digital photograph of an embodiment of the all-suture anchor of FIG. 46 in a post-deployment configuration after addition of an activator according to an embodiment;

FIG. 49 is a side view schematic representation of an all-suture anchor insertion device according to an alternative embodiment;

FIG. 50 is a perspective view schematic representation of an all-suture anchor insertion device in a pre-deployed configuration and position according to an alternative embodiment; and FIG. 51 is a perspective view schematic representation of an all-suture anchor insertion device in a pre-deployed configuration and position according to an alternative embodiment.

DETAILED DESCRIPTION OF THE INVENTION

Set forth below are example descriptions related to the structure and functionality of, and to a method associated therewith, a self-drilling all-suture anchor and inserter of embodiments of the present invention. Advantages of the invention are illustrated by the example descriptions set forth herein. However, the particular conditions and details are to be interpreted to apply broadly in the art and should not be construed to unduly restrict or limit embodiments of the invention in any way.

Referring now to the drawings, wherein like reference numerals refer to like parts throughout, there is seen in FIG. 1 a perspective view schematic representation of an inserter 10 in the unloaded, pre-deployment configuration, according to an embodiment. The inserter 10 is generally composed of metal, such as stainless steel or nitinol; however, other suitable materials with sufficient strength to handle the forces required to drill and insert an anchor may be used (as should be understood by a person of ordinary skill in the art in conjunction with a review of this disclosure). Further, different features of the inserter 10 may be composed of different materials. For example, a sufficiently small diameter nitinol can be used for a length 12 of the inserter 10 to allow the inserter 10 to have the required flexibility to pass and operate in a curved guide tube to reach a desired insertion location. In another example, a sufficiently large diameter stainless steel can be used for the length 12 of the inserter 10 to allow the inserter 10 to have the required stiffness to be located at the desired insertion location and operate under its own support without the use of a guide tube.

Figure 9C:
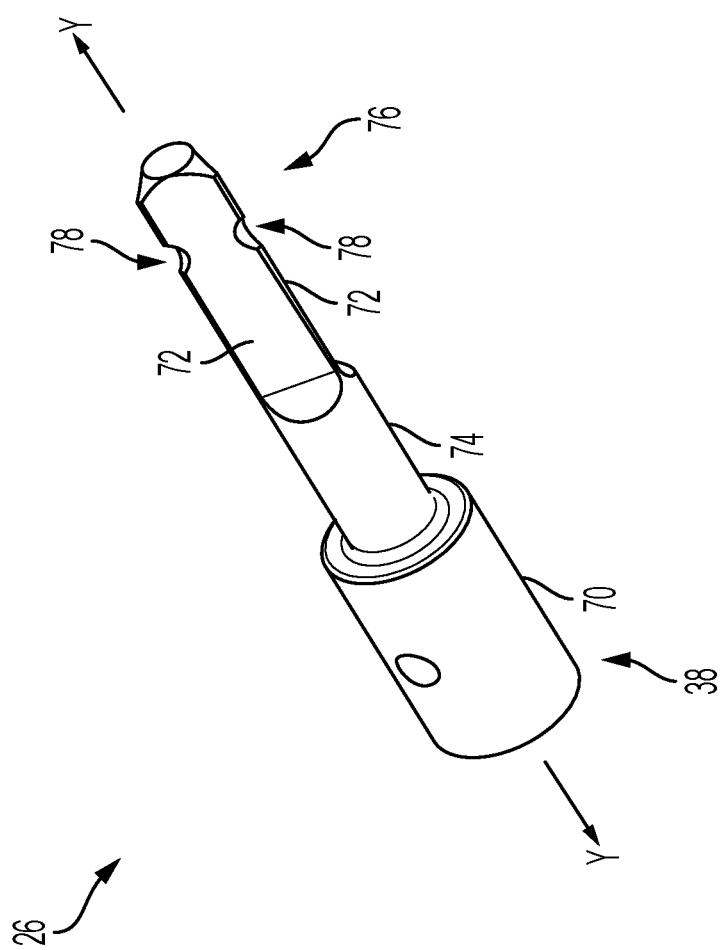
FIG. 9C is a perspective view schematic representation of the quick change connector of FIG. 9A.
Figure 10B:
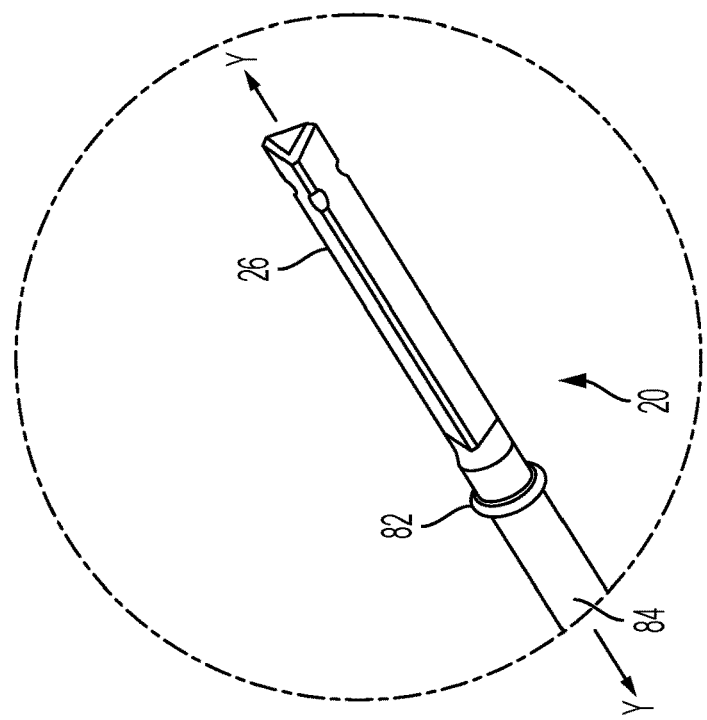
FIG. 10 is a detailed view schematic representation a proximal hard stop feature on the inserter, according to an embodiment.
Figure 10A:
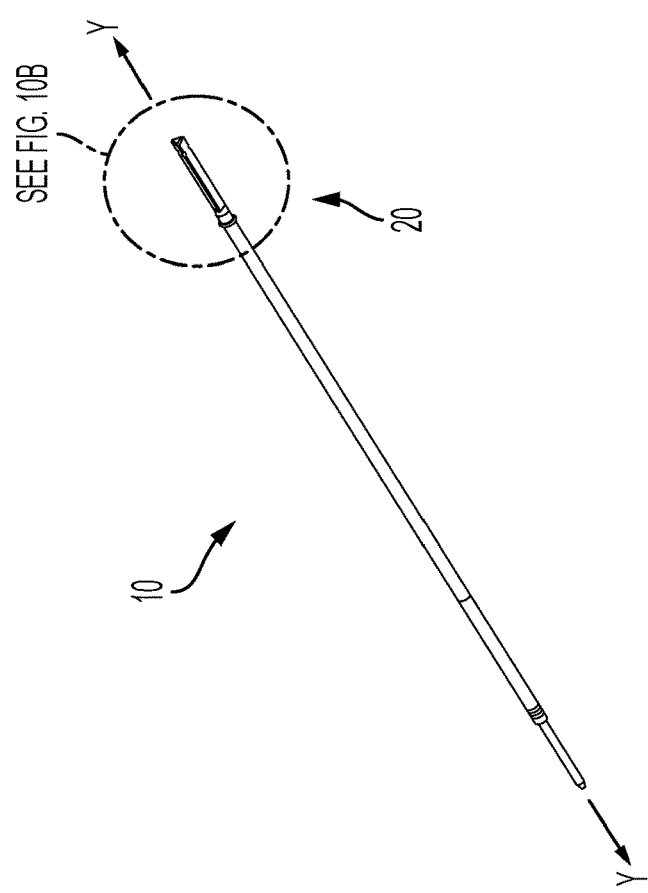

As shown in FIG. 1, the inserter 10 comprises a distal end 14 having an inserter tip 16 connected to a shaft 18, which extends proximally along a central longitudinal y-y axis to connect to a tubular portion 22. The tubular portion 22 extends between the shaft 18 and the proximal end 20. However, in one embodiment, the shaft 18 extends the full length of the inserter 10 without a tubular portion 22, as shown in FIGS. 32-35. In another embodiment shown in FIG. 31, the proximal end 20 of the inserter 10 is at a proximal end 24 of the tubular portion 22. In such an embodiment, the drilling (as described below) is performed by gripping and rotating the tubular portion 22 with a handpiece chuck. The tubular portion 22 may include flat surfaces, as shown in FIGS. 9A and 10 (e.g., flat surfaces 72), or other features that facilitate connection with the chuck. In the embodiment wherein the shaft 18 extends the full length of the inserter 10, the shaft 18 may also include flat surfaces (e.g., flat surfaces 72 in FIGS. 9A and 10) on the proximal end 20 of the inserter 10 (i.e., shaft 18) to similarly facilitate drilling. However, as shown in FIG. 1 and described hereinafter, the tubular portion 22 can extend to a power handpiece interface, such as a quick change connector 26, at the proximal end 20 of the inserter 10. A quick change connector 26 refers generally to a feature that facilitates the use of a power attachment for drilling. Embodiments of the quick change connector 26 are described in detail below.

Figure 2:
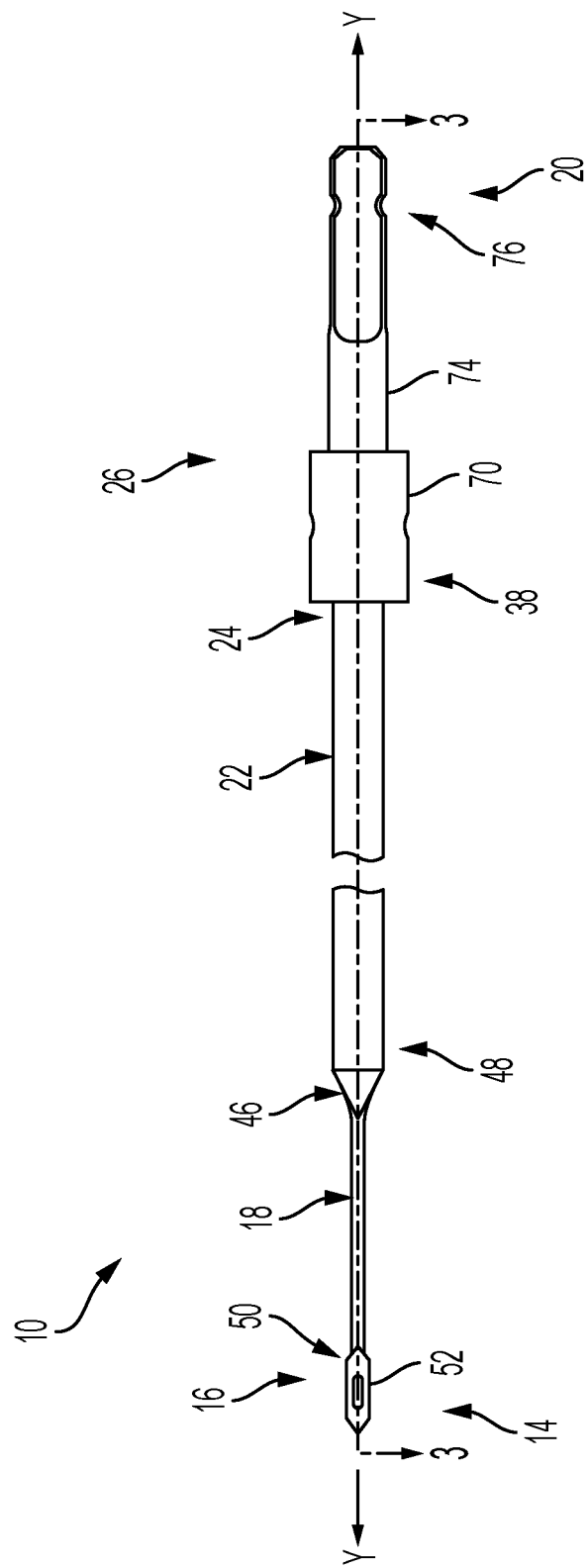
FIG. 2 is a top view schematic representation of the inserter in the unloaded, pre-deployment configuration.
Figure 3:
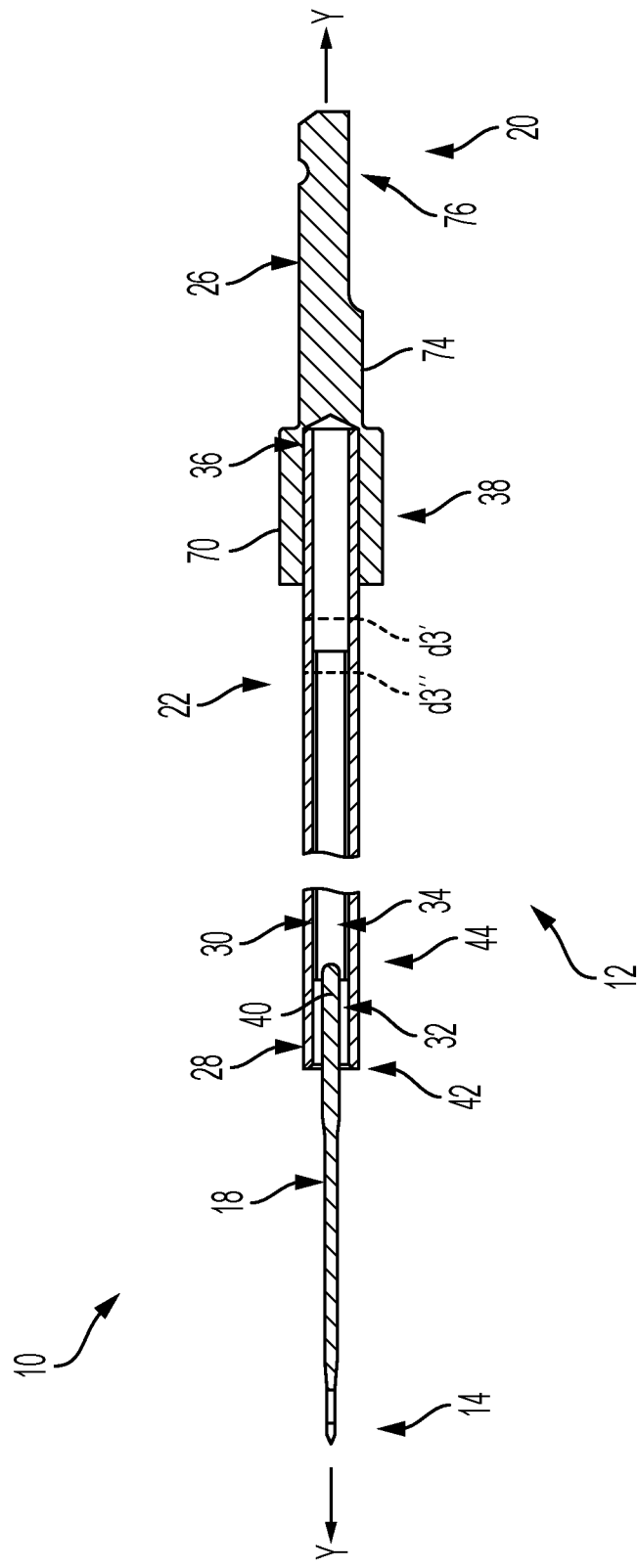
FIG. 3 is a cross-sectional view schematic representation of the inserter of FIG. 2.

Turning now to FIGS. 2-3 there is shown a top view schematic representation and a cross-sectional view schematic representation of the inserter 10 in the unloaded, pre-deployment configuration, according to an embodiment. As shown in FIGS. 2-3, the inserter tip 16 has a relatively thin profile compared to the shaft 18, tubular portion 22, and the quick change connector 26. In the embodiment shown in FIG. 3, the tubular portion 22 can also include, but is not limited to, an outer tube 28 and an inner suture tube 30. As shown, the suture tube 30 is positioned or otherwise located within the outer tube 28. Thus, a diameter d3' of the outer tube 28 is greater than a diameter d3" of the suture tube 30. Therefore, the suture tube 30 extends within a first inner channel 32 of the outer tube 28. Further, the suture tube 30 comprises a second inner channel 34 extending therethrough such that the first inner channel 32 of the outer tube 28 and the second inner channel 34 of the suture tube 30 are in communication. It is important to note that the suture tube 30 does not need to be attached or otherwise directly connected to the inserter tip 16 or shaft 18 of the inserter 10.

In an alternative embodiment, the inserter 10 comprises two or more suture tubes 30 for maintaining separation of lengths of suture. Such multiple suture tubes 30 may be adjacent, concentric, or in any other configuration relative to each other within the outer tube 28. In yet another embodiment, instead of multiple suture tubes 30, a single suture tube 30 comprises a single multi-lumen extrusion and each lumen comprises a length of suture in order to maintain separation of multiple lengths of suture.

As also shown in FIG. 3, at least a proximal portion 36 of the outer tube 28 extends into a distal end 38 of the quick change connector 26. Further, in the depicted embodiment, at least a proximal end 40 of the shaft 18 extends into the tubular portion 22. Specifically, in the depicted embodiment, the proximal end 40 of the shaft 18 extends into both a distal portion 42 of the outer tube 28 and a distal portion 44 of the suture tube 30. In the embodiment shown in FIG. 2, the shaft 18 comprises a tapered portion 46. The tapered portion 46 extends from a distal end 48 of the tubular portion 22 to a position proximal to the proximal end 50 of the inserter tip 16, as shown in FIG. 2. The tapered portion 46 can include external threads (not shown) rigidly connecting the shaft 18 to the outer tube 28. However, other connection methods may be used, such as an interference press fit or welding.

Turning briefly to FIG. 32, there is shown a top view schematic representation of the inserter 10 in the unloaded, pre-deployment configuration, according to an embodiment. In FIG. 32, the inserter 10 comprises a threaded section 45 at the proximal end 20. In the depicted embodiment, the tapered portion 46 extends distally to a contact surface 47 of the outer tube 28. Thus, the outer tube 28 (not shown) can be connected to the inserter 10 via external threads (not shown) on the threaded section 45. In the embodiment shown in FIG. 32, the suture tube 30 is configured to fit over and around the proximal end 20 of the inserter 10.

Still referring to FIG. 2, the inserter tip 16 comprises a suture anchor retention slot 52. The suture anchor retention slot 52 is sized or otherwise configured to hold an anchor braid and length of suture of an all-suture anchor, permitting the all-suture anchor to be pushed into a bone hole created by drilling points 54A, 54B (shown in FIG. 4) at the distal end 14 of the inserter 10 (and inserter tip 16).

Figure 4:
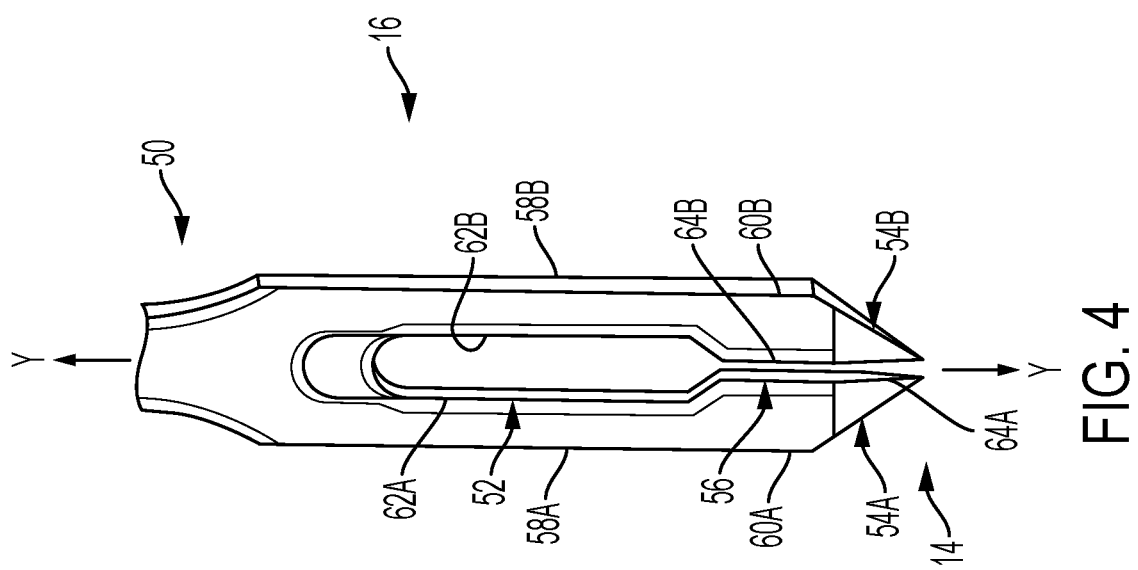
FIG. 4 is a close-up top view schematic representation of the distal end of the inserter, according to an embodiment.
Figure 5:
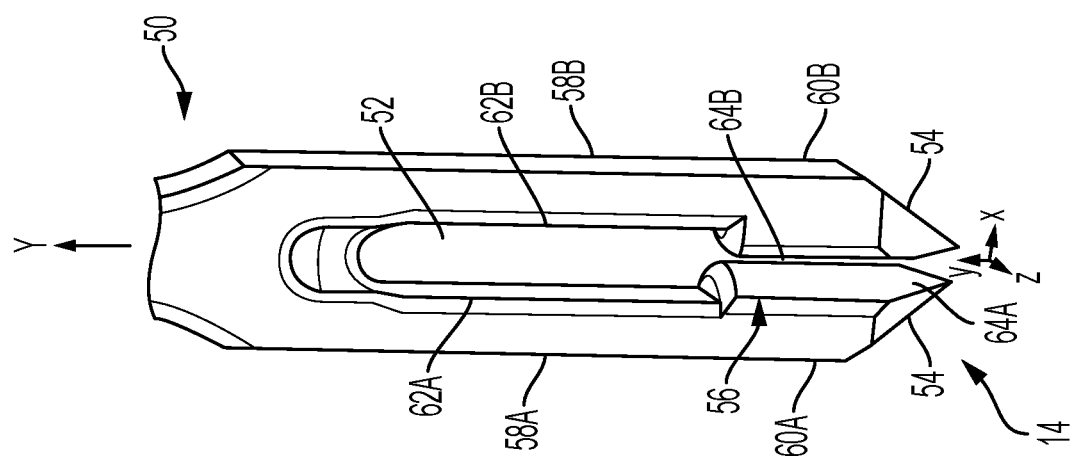
FIG. 5 is a close-up top perspective view schematic representation of the distal end of the inserter, according to an embodiment.

Turning now to FIGS. 4-5, there are shown close-up top and top perspective views schematic representations of the distal end 14 of the inserter 10, according to an embodiment. As shown in FIGS. 4-5, the distal end 14 of the inserter 10 (and inserter tip 16) comprises the suture anchor retention slot 52 which extends through a distal anchor deployment passage 56 to the drilling points 54A, 54B. The anchor deployment passage 56 allows the anchor to be removed from the inserter 10. The anchor deployment passage 56 may be sized equal to, narrower, or wider than the suture anchor retention slot 52. Furthermore, the suture anchor retention slot 52 may change in size during useful life. In another embodiment, the drill points 54A, 54B and anchor deployment passage 56 may be configured such that the material of the inserter 10 flexes in response to rotational or compressive forces applied to the drill points 54A, 54B in a manner to close or open the anchor deployment passage 56.

In the embodiment depicted in FIGS. 4-5, the suture anchor retention slot 52 is elongated, creating a pair of prongs 58A, 58B. Each prong 58A, 58B extends around the suture anchor retention slot 52 to a drilling end 60A, 60B, each with its respective drilling point 54A, 54B. Thus, in the depicted embodiment, there is a pair of drilling points 54A, 54B, each extending from one of a pair of prongs 58A, 58B. The drilling points 54A, 54B are configured to cut bone as they are rotated. The rotation may be multiple single direction revolutions of the inserter 10, or the rotation may oscillate clockwise and counterclockwise in full or partial revolutions of the inserter 10. The drilling points 54A, 54B may have an effective diameter larger or smaller diameter than the other material of the inserter 10. As shown in FIG. 5, the central longitudinal y-y axis extends through, at least approximately, the center of the suture anchor retention slot 52 and the anchor deployment passage 56. In the depicted embodiment, a z-z axis extends perpendicular to the central longitudinal y-y axis.

Still referring to FIG. 5, each of the pair of prongs 58A, 58B comprises an inner wall 62A, 62B defining the suture anchor retention slot 52. The inner walls 62A, 62B each extends along an axis that is parallel to the z-z axis. Similarly, the drilling ends 60A, 60B of the prongs 58A, 58B each have a drilling face 64A, 64B. The drilling faces 64A, 64B oppose each other and each drilling face 64A, 64B extends along an axis that is not parallel to the z-z axis. In other words, the drilling faces 64A, 64B are at an angle relative to the z-z axis and are therefore at an angle relative to the inner walls 62A, 62B. The drilling faces 64A, 64B of the prongs 58A, 58B restricts the suture anchor retention slot 52 from opening in the YZ plane, thereby locking the anchor deployment passage 56 during insertion of the inserter tip 16 into a bone. Further, the angular relationship of the drilling faces 64A, 64B to the inner walls 62A, 62B prevents one of the prongs 58A, 58B from moving in a first direction along an axis parallel to the z-z axis while the other of the prongs 58A, 58B moves in a second direction, opposite the first direction, along an axis parallel to the z-z axis when force is applied to close the prongs 58A, 58B. Thus, the prongs 58A, 58B cannot be moved in opposing directions along an axis parallel to the z-z axis when force is applied along a lateral x-x axis to close the prongs 58A, 58B. As shown in FIG. 5, the lateral x-x axis is perpendicular to the central longitudinal y-y axis.

Turning briefly now to FIG. 35, there is shown a close-up perspective view schematic representation of the distal end 14 of the inserter 10, according to an embodiment. As shown in FIG. 35, the inserter tip 16 has a first face 57 with a length L1 and a second face 59 with a length L2. Specifically, L2 is greater than L1 to create an effective drilling diameter d1 that is larger than a diameter d2 of the shaft 18. The difference in diameters d1, d2 allows clearance for the anchor, suture, and shaft 18 in a bone hole.

Turning now to FIGS. 33-34, there are shown top views schematic representations of the inserter 10 in the unloaded, pre-deployment configuration, according to alternative embodiments. In the embodiment shown in FIG. 33, the inserter tip 16 is spade-shaped. The spade-shaped inserter tip 16 allows the drilling points 54A, 54B to drill a larger hole, as compared to the inserter tip 16 in FIGS. 4-5, while providing space for an anchor braid behind the drilling points 54A, 54B. FIG. 34 shows an embodiment of the inserter tip 16 with an offset anchor deployment passage 56 (offset relative to the central longitudinal y-y axis). The offset anchor deployment passage 56 allows for a true drill point 55 at the first drilling point 54A.

Figure 6A:
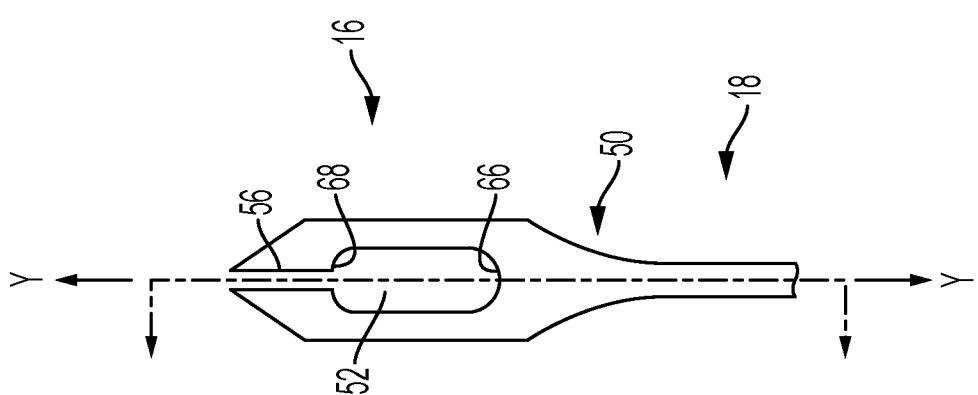
FIG. 6A is a top view schematic representation of an inserter tip, according to an embodiment.
Figure 7A:
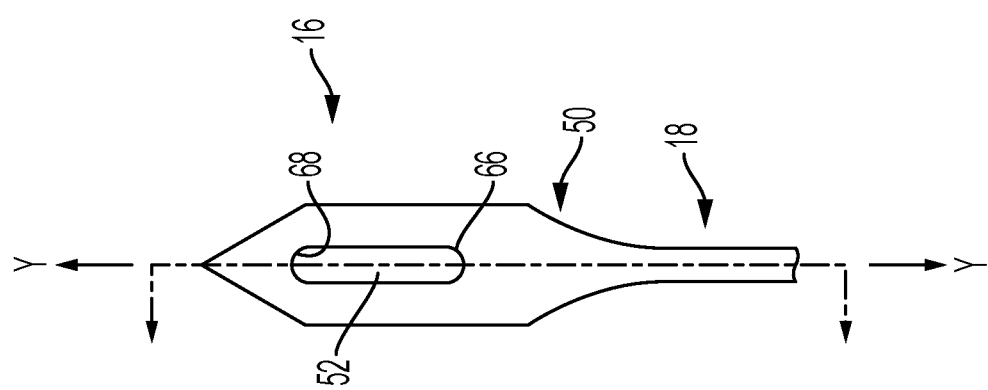
FIG. 7A is a top view schematic representation of an inserter tip, according to an alternative embodiment
Figure 7B:
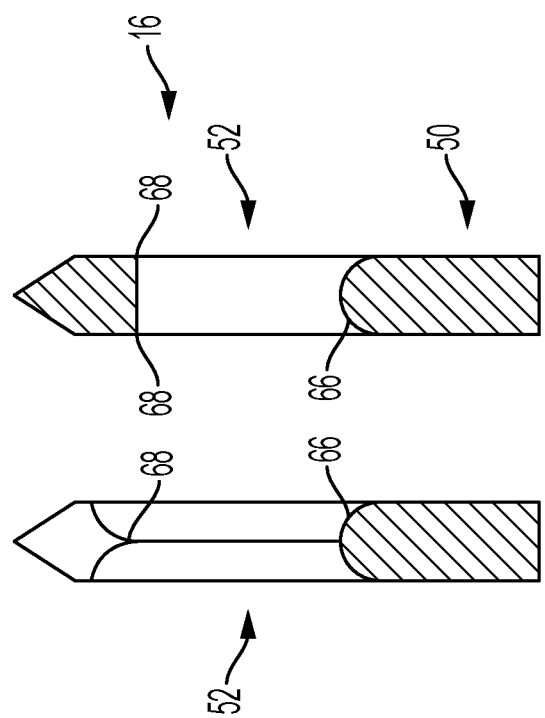
FIG. 7B is a cross-sectional view schematic representation of the inserter tip of FIG. 7A.

Referring now to FIGS. 6A-6B, there is shown a top view schematic representation and a cross-sectional view schematic representation of an inserter tip 16, according to an embodiment. As shown in FIGS. 6A-6B, the suture anchor retention slot 52 comprises a rounded proximal edge 66 and a sharp distal edge 68. The sharp distal edge 68 allows the inserter 10 to withdraw from the bone easily and to release the all-suture anchor reliably. In particular, the sharp distal edge 68 is used to cut the anchor braid (not a length of suture) so that the inserter 10 can be removed without loosening or pulling out the all-suture anchor. On the other hand, the rounded proximal edge 66 protects the anchor braid during insertion. While the inserter tip 16 shown in FIGS. 6A-6B comprises the anchor deployment passage 56, the inserter tip 16 of FIGS. 7A-7B does not. In the alternative embodiment of the inserter tip 16 shown in FIGS. 7A-7B, the all-suture anchor is loaded into the anchor retention slot 52 and advanced into the bone by force from the rounded proximal edge 66. The all-suture anchor is then cut into two pieces by the sharp distal edge 68 when the inserter 10 is retracted and removed.

Figure 8A:
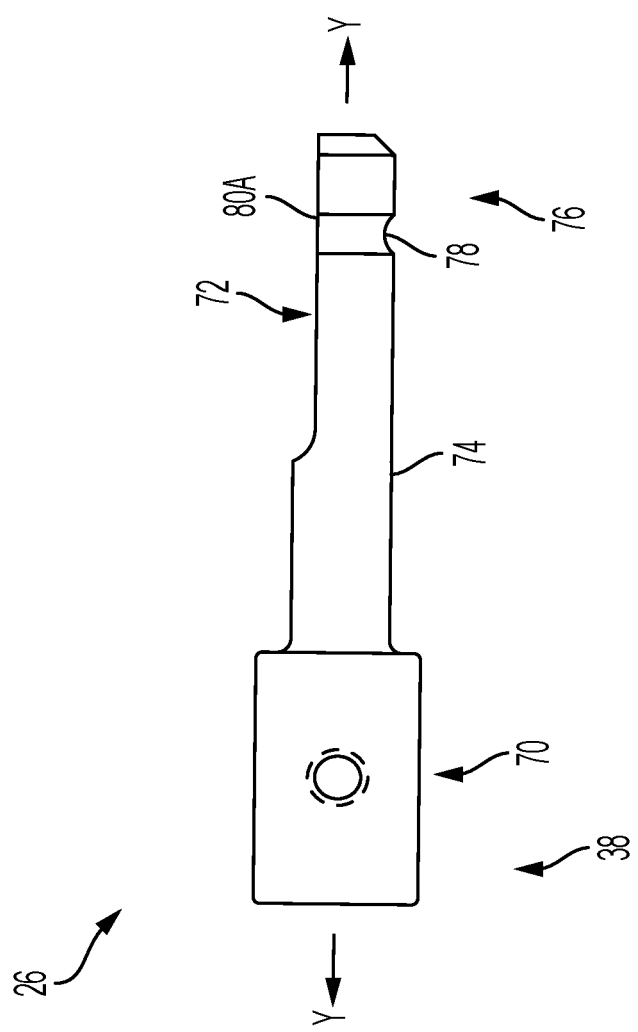
FIG. 8A is a side view schematic representation of a quick change connector, according to an embodiment.
Figure 8B:
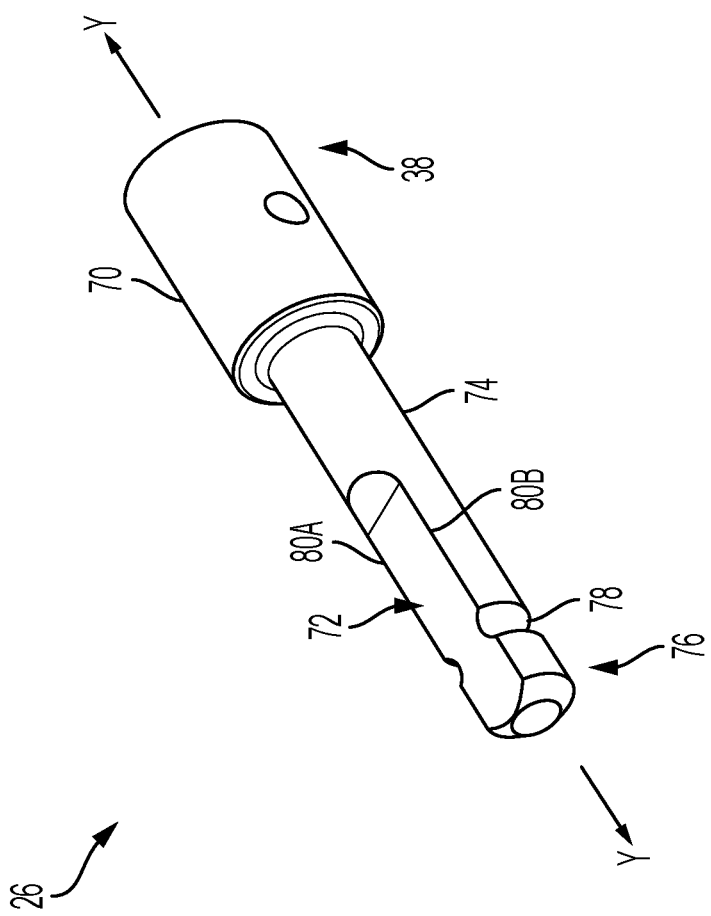
FIG. 8B is a perspective view schematic representation of the quick change connector of FIG. 8A.
Figure 8C:
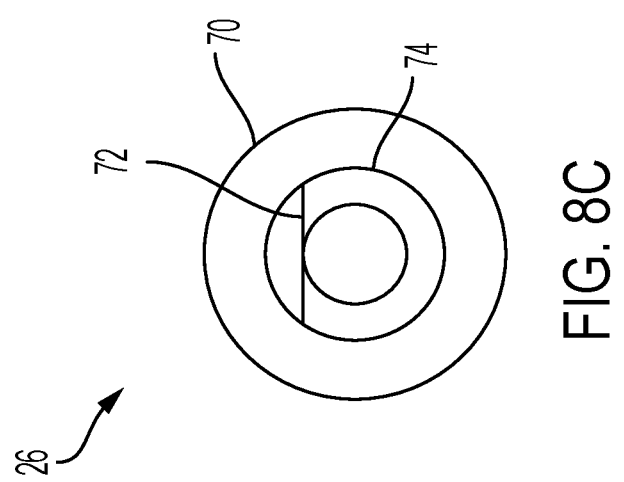
FIG. 8C is a front view schematic representation of the quick change connector of FIG. 8A.

Referring briefly back to FIGS. 2-3, the quick change connector 26 comprises an adapter 70 at its distal end 38 with a rod 74 extending therefrom to a proximal end 76. Turning now to FIGS. 8A-8C, there are shown various views schematic representations of a quick change connector 26, according to an embodiment. As shown in FIGS. 8A-8C, the adapter 70 is compatible with a traditional AO connection (as should be understood by a person of ordinary skill in the art in conjunction with a review of this disclosure). However, other connections, such as a Trinkle or Hudson connection can be used. The rod 74 comprises a flat surface 72 extending along an axis parallel to the central longitudinal y-y axis, as shown in FIGS. 8A-8B. In the depicted embodiment, the rod 74 comprises a groove 78. The groove 78 extends into the rod 74 from a first edge 80A of the flat surface 72 to a second edge 80B of the flat surface 72.

Turning now to FIG. 9A-9D, there is shown various views schematic representations of the quick change connector 26, according to an alternative embodiment. As shown in FIG.

Figure 9D:
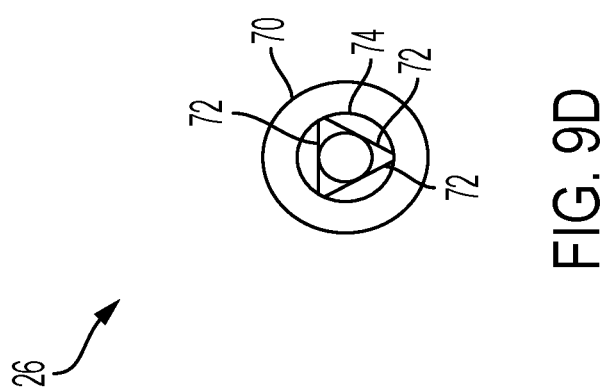
FIG. 9D is a front view schematic representation of the quick change connector of FIG. 9A.

9A, the rod 74 comprises three flat surfaces 72, having a triangular cross-section (shown in FIG. 9D). The rod 74 also comprises three grooves 78, which extend into the rod 74 at positions wherein the two of the three flat surfaces 72 meet or otherwise converge, as shown in FIGS. 9A and 9C. Also shown in FIGS. 9B-9C, the adapter 70 is compatible with a traditional AO connection (other connections may be used). However, the three flat surfaces 72 permit the central longitudinal y-y axis of the inserter 10 to be co-linear with a central longitudinal y-y axis extending through a grasping chuck (not shown). The quick change connector 26 can be formed from a solid piece of metal (in FIG. 9B, 9C, 9D) or formed into the end of tubing (FIG. 9A). Forming the quick change connector 26 into tubing offers many advantages for use with the inserter 10. For example, the proximal end 76 is kept open to allow better flow of Ethelene Oxide for sterilization of the suture material housed inside the tubing and there can be a reduction in the number of components needed for assembly of the inserter 10.

Referring now to FIG. 10, there is shown a detailed view schematic representation of a proximal hard stop feature 82 on the inserter 10, according to an embodiment. As shown in the depicted embodiment, a hard stop feature 82 is positioned or otherwise located along the proximal end 20 of the inserter 10. The hard stop feature 82 is distal the quick change connector 26 such that the hard stop feature 82 prevents the quick change connector 26 from entering or advancing through a guide. In the depicted embodiment, the hard stop feature 82 is a ring wrapped around an outer surface 84 of the inserter 10. However, any other shape or configuration for a hard stop feature 82 can be used if sufficiently sized larger than a diameter of the guide.

Figure 11B:
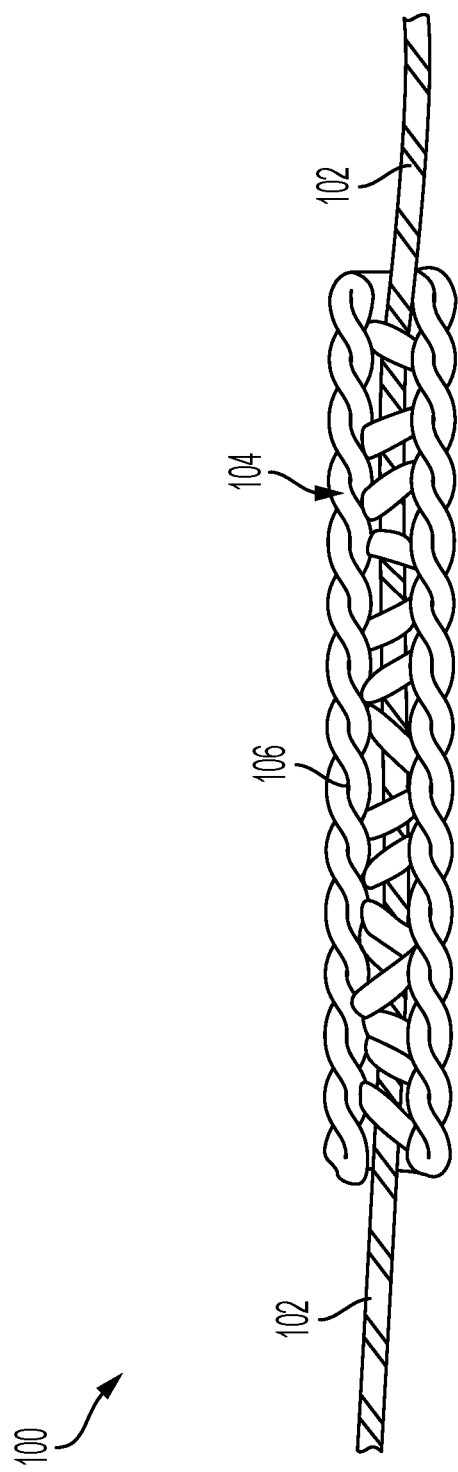
FIG. 11B is a top view schematic representation of the all-suture anchor of FIG. 11A.
Figure 12A:
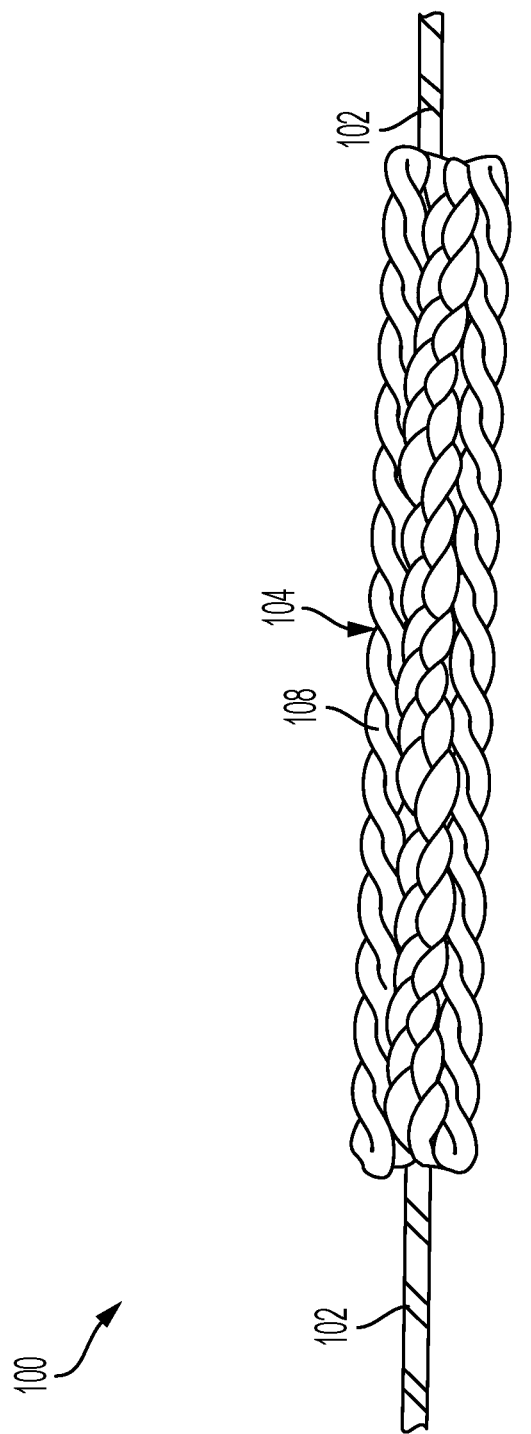
FIG. 12A is a back view schematic representation of an all-suture anchor, according to an embodiment.
Figure 12B:
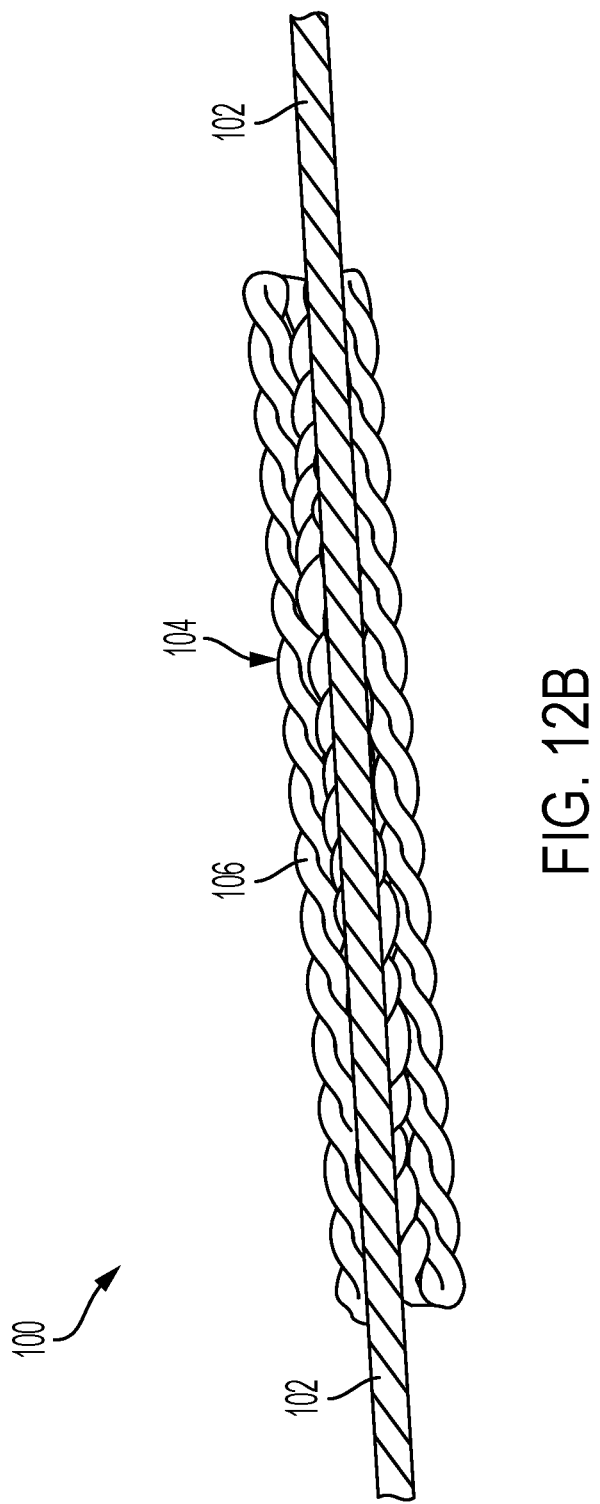
FIG. 12B is a top view schematic representation of the all-suture anchor of FIG. 12A.

Referring briefly to FIGS. 11A-12B, there are shown front and back views schematic representations of the all-suture anchor 100, according to an embodiment. FIG. 11A shows a back view of an all-suture anchor 100, while FIG. 11B shows the front view. As shown, the length of suture 102 passing into and out of the anchor braid/fibrous construct 104 only passes through one (e.g., "front") surface 106 of the anchor braid 104 (FIG. 11B). Similarly, FIGS. 12A-12B also show a back view (FIG. 12B) and front view (FIG. 12A) where the suture 102 passing only through one (e.g., "front") surface 106 of the anchor braid 104 (FIG. 12B). When the all-suture anchor 100 has suture 102 passing only through one (e.g., "front") surface 106, the anchor braid 104 protects the suture 102 from abrasion on the opposing (e.g., "back") surface 108 (FIGS. 11A and 12A) when loaded onto the inserter (as should be understood by a person of ordinary skill in the art in conjunction with a review of this disclosure). In FIGS. 11A-12B, the suture 102 is passed through the anchor braid 104 at numerous passing locations. The number of passing locations in FIGS. 13B and 14B is eight passing locations 110, while the number of passing locations for some alternative all-suture anchors 100 is six passing locations 110. The number of passing locations 110 can vary depending on the composition and size of the suture 102 and/or anchor braid 104. The number of passing locations 110 can be optimized by balancing input parameters, such as anchor braid length, anchor braid width, anchor braid pick density, suture diameter, and others, to yield output parameters, such as manufacturability, anchor creep under load, and pullout strength.

Turning briefly to FIGS. 36A-36B, there are shown top and side views schematic representations of an all-suture anchor 100, according to an alternative embodiment. As shown in FIGS. 36A-36B, the length of suture 102 passes through an approximate center 105 of the anchor braid 104.

In the depicted embodiment, the length of suture 102 enters the anchor braid 104 through one (e.g., "front") surface 106 and exits through the opposing (e.g., "back") surface 108 of the anchor braid 104. With the length of suture 102 positioned on both sides of the anchor braid 104, the anchor braid 104 can be loaded onto the inserter 10 such that anchor braid 104 can be positioned against a bone, while the lengths of suture 102 are along the inserter 10, as shown in FIG. 41

In another alternative embodiment, as shown in FIGS. 39A-39B, the anchor braid 104 can be loaded with multiple lengths of suture 102A, 102B. In the depicted embodiment, the anchor braid 104 is loaded with two lengths of suture 102A, 102B. The lengths of suture 102 may extend through the anchor braid 104 along its opposing edges 107A, 107B (FIG. 39B), through two off-center locations 109A, 109B (FIG. 39A), or any conceivable combination thereof (including an extension of the length of suture 102A, 102B through the approximate center 105 of the anchor braid 104). In addition, the lengths of suture 102A, 102B may enter/exit the anchor braid 104 on the same surface (FIGS. 11A-12B) or on opposing surfaces (FIGS. 36A-36B).

Referring now to FIGS. 37A-38, there are shown top views schematic representations of an all-suture anchor 100, according an additional alternative embodiment. FIGS. 37A-37C depict the process for creating an inverted anchor braid 104. As shown in FIG. 37A, a threader 128 with a threader loop 130 is first passed through the anchor braid 104. Then, in FIG. 37B, an end 114B of the anchor braid 104 is pulled through the threader loop 130. Finally, the threader loop 130 is pulled back through the anchor braid 104, creating a central eyelet 132, as shown in FIG. 37C. A length of suture 102 can be loaded onto the inverted anchor braid 104 by passing the length of suture 102 through the anchor braid 104, as described in conjunction with any of the embodiments shown in FIGS. 11A-12B, 36A-36B, and FIGS. 39A-39B, and passing through the central eyelet 132, as shown in FIG. 38.

Figure 13A:
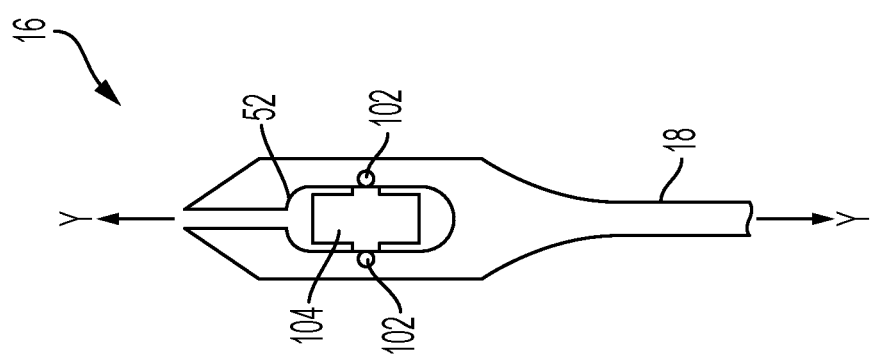
FIG. 13A is a top view schematic representation of an all-suture anchor loaded onto the inserter tip, according to an embodiment.

Referring back to FIGS. 11A-12B, from the unloaded, pre-deployment configuration shown, the all-suture anchor 100 is loaded onto the inserter tip 16, as shown in FIGS. 13A-13B. To load the inserter tip 16, the anchor braid 104 is fed through the suture anchor retention slot 52 such that a pair of ends 112A, 112B of the suture 102 and a pair of ends 114A, 114B of the anchor braid 104 are on opposing sides of the suture anchor retention slot 52 (and inserter 10). Further, in one embodiment, the all-suture anchor 100 is fed through the suture anchor retention slot 50 such that four of the passing locations 110 are on opposing sides of the suture anchor retention slot 52 (and inserter 10). The suture 102 is then pulled taut along the shaft 18, which causes the pair of ends 112A, 112B of the suture 102 and the pair of ends 114A, 114B of the anchor braid 104 to extend along the inserter 10 (i.e., each along an axis approximately parallel to the central longitudinal y-y axis).

Turning now to FIGS. 14A-14B, there are shown top views schematic representations of an all-suture anchor, according to an alternative embodiment, in the unloaded, pre-deployment configuration and the loaded, pre-deployment configuration. The all-suture anchor 10 shown in FIGS. 14A-14B is a Y-Knot suture anchor. Certain structural and functional aspects of embodiments of the present invention are similar to embodiments of the soft suture anchor described and illustrated in U.S. Pat. No. 9,826,971. Those similarities should be understood by a person of ordinary skill in the art in conjunction with a review of this disclosure and accompanying drawings in conjunction with the published application, and are not further discussed in detail herein. Certain differences, including various inventive features of embodiments of the present invention are further briefly described herein and below with reference to the accompanying drawings. However, in the embodiment wherein the all-suture anchor 100 is a Y-Knot suture anchor, only the anchor braid 104 is loaded into the inserter tip 16. As shown in FIG. 14B, when the anchor braid 104 is loaded in the suture anchor retention slot 52, a central portion 116 of the suture 102 is pulled away from (i.e., in a direction distal to) the inserter tip 16. This prevents the suture 102 from falling into the suture anchor retention slot 52. Keeping the suture 102 out of the suture anchor retention slot 52 avoids potential damage to the suture 102 due to heat generated in the prongs 58A, 58B (FIGS. 4-5) of the inserter 10 as it is drilled into bone or from being severed upon removal of the inserter 10. In one embodiment, once the all-suture anchor 100 is loaded onto the inserter tip 16, as shown in either of the embodiments in FIGS. 13A-14B, the anchor deployment passage 56 can be moved to a closed position to create an enclosed suture anchor retention slot 52, as shown in FIG. 15. In one embodiment, the anchor deployment passage 56 is moved to the closed position by bending the prongs 58A, 58B in manner to fully close the anchor deployment passage 56.

Figure 16:
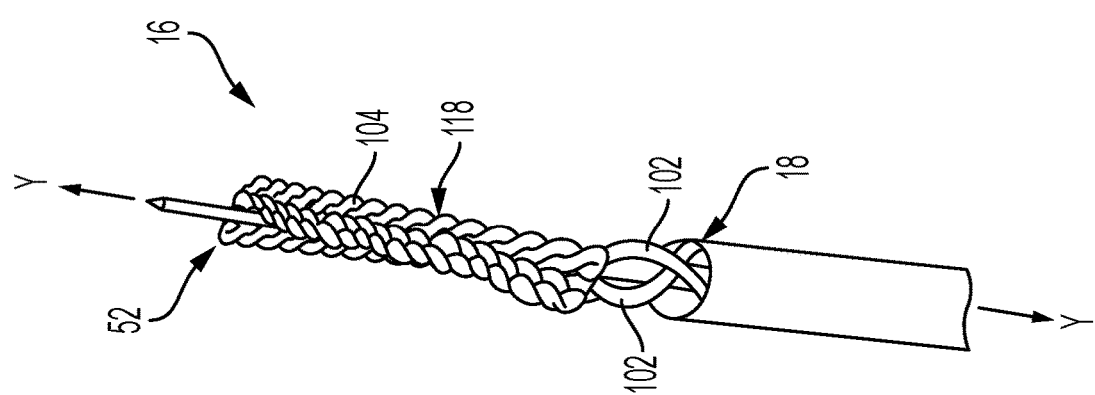
FIG. 16 is a side view of an all-suture anchor in the loaded, pre-deployment configuration on the inserter, according to an embodiment.

Referring now to FIG. 16, there is shown a side view of an all-suture anchor 100 in the loaded, pre-deployment configuration on the inserter 10, according to an embodiment. As shown in FIG. 16, when the all-suture anchor 100 is loaded onto the inserter tip 16, the anchor braid 104 is twisted along the inserter tip 16. When the anchor braid 104 is loaded onto the inserter tip 16 with a tight twist 118, no further twisting of the anchor braid 104 occurs when the anchor braid 104 is inserted into the bone by rotating the all-suture anchor 100 in the direction of the twist 118. In other words, the twist 118 in the anchor braid 104 when it is loaded onto the inserter tip 16 prevents the anchor braid 104 from twisting upon itself as it is inserted into the bone and prevents length of suture 102 from twisting over itself as a result of twisting of the anchor braid 104. Therefore, the suture 102 can exit the bone hole without a twist. In the depicted embodiment, the anchor braid 104 has a 1.5 revolution twist 18, which results in virtually no exposure of the length of suture 102 at the inserter tip 16.

Turning now to FIGS. 17A-17B, there are shown top views schematic representations of an anchor braid 104 with an additional material 120, according to an embodiment. One of ordinary skill in the art should recognize and appreciate potential embodiments of a Y-Knot anchor with additional material, such as monofilament polymers, to add strength. Additional material can be applied to the all-suture anchor 104. As shown in FIG. 17A, the anchor braid 104 is folded in half. A monofilament 120 is used to stitch together each (i.e., two) side edge 122A, 122B of the anchor braid 104 to create an enclosed area 124 with the length of suture 102 inside, as shown in FIG. 17B. In addition to improved strength, this will prevent the anchor braid 104 from rolling over on itself during insertion and exposing the suture 102 to the bone, causing abrasion. Additionally, the described twisting of the anchor braid 104, in combination with a more dense material running in the axis of the anchor braid 104 can result in a threaded all-suture anchor 100.

Turning briefly to FIG. 18, there is shown a perspective view schematic representation of the inserter 10 in the loaded, pre-deployment configuration, according to an embodiment. In the depicted embodiment, an anchor braid 104 is loaded onto the inserter tip 16 as described above. FIG. 19 shows a side view schematic representation of the inserter 10 in the loaded, pre-deployment configuration, according to the embodiment. In FIG. 19 the outer tube 28 and the quick change connector 26 have been removed for clarity. As shown, the anchor braid 104 extends through the suture anchor retention slot 52 and has a twist 118 around the inserter tip 16. The first and second ends 112A, 112B of suture extend on opposing sides of the shaft 18 within the suture tube 30. In the depicted embodiment, the ends 112A, 112B are backed or pulled distally in the suture tube 30. FIGS. 20-21 similarly show the ends 112A, 112B within the inner volume 34 of the suture tube 30. FIGS. 22-24 also show various top and cross-sectional views schematic representations of the inserter 10 in the loaded, pre-deployment configuration, according to an embodiment. The outer tube 28 houses the suture tube 30 and the ends 112A, 112B of suture 102 so that these components may spin, twist, or otherwise rotate with the anchor braid 104 during insertion.

As shown in FIGS. 19, 21 and 23, the first and second ends 112A, 112B of suture 102 extend from the anchor braid 104 along the shaft 18 and into the suture tube 30. Once within the suture tube 30, the first and second ends 112A, 112B of suture 102 are backed toward the inserter tip 16, as shown. With the first and second ends 112A, 112B on opposing sides of the shaft 18 and within the suture tube 30, the shaft 18 presses and locks the limbs 112A, 112B against the suture tube 30, thereby tensioning the length of suture 102 and maintaining the position and configuration of the anchor braid 104. FIG. 41 also shows a suture tube 30 extending around the lengths of suture 102 and the shaft 18. The suture tube 30 compressed the lengths of suture 102 against the shaft 18. Although not shown in FIG. 41, the suture tube 30 extends the entire length of suture 102.

Referring now to FIGS. 25-26, there are shown various views schematic representations of the inserter 10 in the loaded, pre-deployment configuration, according to an alternative embodiment. As shown in FIG. 25, the shaft 18 comprises a flex region 126. In the embodiment depicted in FIG. 26, the flex region 126 extends in the tubular portion 22 of the inserter 10. Thus, the flex region 126 can extend along any portion of the length 12 (FIG. 1) of the inserter 10. The flex region 126 can be created by a series of small cuts, laser cut or etched, for example, as shown in FIG. 26. The flex region 126 increases the flexibility of the inserter 10 (as should be understood by an ordinary skill in the art in conjunction with a review of this disclosure) such that the inserter 10 can be extended through a curved guide.

Turning briefly to FIGS. 40A-40B, there are shown side view schematic representations of a cleat component 134, according to alternative embodiments of the inserter 10. In FIG. 40A, the inserter 10 comprises a slidable cleat component 134. The shaft 18 passes through the cleat component 134, but is not attached. The cleat component 134 comprises proximal end 136 and a distal end 138. In use, the length of suture 102 is wrapped around the proximal and distal ends 136, 138 to secure the length of suture 102 in place. The cleat component 134 can be moved proximally (with limits) or distally along the inserter 10 by sliding the cleat component 134 along the shaft 18. In another embodiment, shown in FIG. 40B, the cleat component 134 comprises a slot 140 to hold the length of suture 102. Thus, the length of suture 102 is wrapped around the proximal and distal ends 136, 138 of the cleat component 134 and is secured within the slot 140. In use, after the inserter 10 drills a bone hole, the user can remove the length of suture 102 from the slot 140, unwrap the length of suture 102 from the proximal and distal ends 136, 138, and remove the inserter 10.

In another embodiment, shown in FIG. 42, a sleeve 142, such a rubber sleeve, is positioned over the shaft 18, the cleat component 134, and the length of suture 102 to hold the length of suture 102 in place. As stated briefly above, the cleat component 134 (with the length of suture 102 and sleeve 142) can slide distally along the shaft 18. However, proximal movement of the cleat component 134 along the shaft 18 is limited due to the tension in the length of suture 102. Due to the limited proximal translation, a distal surface 144 of the sleeve 142 also serves a hard stop for the inserter 10. Thus, in use, the inserter 10 is drilled into a bone until the hard stop (e.g., distal surface 144 of the sleeve 142) contacts a guide and the shaft 18. When the shaft 18 is removed from the bone, the anchor braid 104 and length of suture 102 remains in the bone, while the cleat component 134 and sleeve 142 is attached to the length of suture 102. As the shaft 18 is no longer positioned through the cleat component 134, the length of suture 102 can be released from the cleat component 134 and sleeve 142.

Referring now to FIG. 27, there is shown a side view schematic representation of the inserter 10 in the loaded, pre-deployment configuration at a bone hole location 86, according to an embodiment. As shown, the inserter 10 is extended through a guide 88 at a selected bone hole location 86 such that a distal end 90 of the guide 88 is positioned at the surface 92 of the bone 94, while the quick change connector 26 extends through and past the proximal end 96 of the guide 88. In the depicted embodiment, the inserter tip 16 loaded with the anchor braid 104 in the distal end 90 of the guide 88 is positioned at the surface 92 of the bone 94. Once positioned and while the guide 88 is held stationary relative to the bone 94, the user rotates the inserter via the quick change connector 26 using a handpiece, which rotates the drilling ends 60A, 60B and their respective drilling points 54A, 54B, and pushes the inserter 10 into the bone 94 until the anchor braid 104 is fully inserted into the bone 94. Features, such as the hard stop feature 82 (FIG. 10) limit the insertion depth by not allowing the inserter 10 to go further through the guide 88.

Turning now to FIG. 28, there is shown a side view schematic representation of the inserter 10 in the loaded, pre-deployment configuration in a bone hole 98, according to an embodiment. As shown, the drilling ends 60A, 60B and their respective drilling points 54A, 54B form a hole 98 in the bone 94 as the inserter 10 advances in the guide 88. Once the anchor braid 104 is inserted into the bone hole 98, the anchor braid 104 forces open the anchor deployment passage 56 to allow the inserter 10 to be removed leaving the anchor behind in a bone hole. In another embodiment, the anchor deployment passage 56 may be forced open by an additional object such as a filament of suture, wire, or rod that opens the anchor deployment passage 56 as the inserter 10 is removed or actuated independently. In another embodiment, the anchor deployment passage 56 may be blocked during insertion by an additional member such as a filament, wire, rod, portion of the anchor, or other material to create a fully enclosed suture anchor retention slot 52. The blocking material my exit the anchor deployment passage 56 as the inserter 10 is withdrawn or by independent actuation. Ultimately, when the anchor deployment passage 56 is open, the inserter 10 can be retracted through the guide 88 such that inserter tip 16 is removed from the bone 94, with the anchor braid 104 remaining in the bone hole 98 and passing though the anchor deployment passage 56 as the inserter 10 is withdrawn. The force to keep the anchor braid 104 in the bone hole 98 may be provided by interaction between the bone 94 and the anchor braid 104 or by interaction between the anchor braid 104 and another member introduced to hold the anchor braid 104 in place before the all-suture anchor 100 is deployed.

Referring now to FIG. 29, there is shown a side view schematic representation of the inserter 10 in the unloaded, post-deployment configuration, according to an embodiment. Once the anchor braid 104 is fully inserted and the inserter 10 is removed, tension is applied to the suture 102 (ends 112A, 112B) by removal of the inserter 10, the user pulling directly on the suture 102 (ends 112A, 112B) or a combination of both means. The tension causes the anchor braid 104 to deploy into a post-deployment configuration to provide fixation.

Turning now to FIGS. 30A-30B, there are shown side view schematic representations of an embodiment of the all-suture anchor 100 in the pre-deployment and post-deployment configurations. In the depicted embodiment, the all-suture anchor 100 is a soft suture anchor, such as the Y-Knot® anchor 200. One such suture anchor is disclosed in U.S. Pat. No. 9,826,971 assigned to the assignee hereof and incorporated by reference herein in its entirety.

An embodiment of the Y-Knot® anchor (or soft anchor or "all-suture" anchor) 200 is illustrated in detail in FIGS. 30A-30B. The Y-Knot® anchor 200, as shown in FIGS. 30A-30B, contains at least two sections: at least one suture 202, which is a suture to be anchored; and an anchor body 204, which is to form a portion of the anchor 200 that can increase in width, thickness and/or diameter and shrink in length as part of deployment. See FIG. 30A, showing the anchor body 204 in the pre-deployment configuration; and FIG. 30B, showing the anchor body 204 "shortened" and "expanded" in the post-deployment configuration, which is additive to the increase due to the pleats. This soft anchor embodiment also takes advantage of Poisson's ratio, which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. Although, it is the anchor body 204 that increases in width, thickness and/or diameter at deployment, it should be understood that the suture 202 can also play a role in the deployment of the anchor 200 even though the suture 202 may remain free (in some embodiments) to slide, and non-slidable in others (at least at a particular position or point in use) in relation to the anchor body 204. The suture 202 helps to position, align and support the anchor body 204, such that if the suture 202 were to be removed from the anchor body 204 after deployment of the anchor 200, the anchor body 204 may be free to spill (i.e., release), allowing the anchor body 204 to collapse and shrink in size, allowing for easy (and potentially undesirable) removal.

In other words, the anchor body 204 has two primary functions. First, it becomes a base for the suture 202 to slide within. Second, when compressed and/or pleated during deployment, the anchor body 204 becomes more compact in one direction thereby expanding outwardly and increasing its overall width, thickness or diameter to create a retention capacity. This action of having the anchor body 204 change in shape to increase its overall width, thickness or diameter is a useful characteristic which may be used advantageously to secure the anchor 200 in a hole 98 or against a bony or soft tissue 94. It is this combination of the expanding anchor body 204 coupled with the suture 202 remaining slidable (in some embodiments; and non-slidable in others, at least at a particular position or point in use) in relation to the anchor body 204 that render embodiments of the present invention ideal for the reattachment of soft tissue to bone 94 or soft tissue to soft tissue where it is desirable to pass sliding knots to secure a repair.

The discussion below relates to alternative embodiments of a disposable handpiece, alternative embodiments of all-suture anchors that can be used in conjunction with/deployed by embodiments of the anchor inserter described herein, and an alternative embodiment of an anchor installation device/inserter and drill.

Turning to FIG. 43, a side view schematic representation of a disposable handpiece 300 according to an alternative embodiment is shown. The disposable handpiece can include, but is not limited to, a motor 301, a chuck 302, disposable battery(ies) 303 configured to supply power to the motor, and at least one switch 304 configured to be actuated (rotationally, linearly, perpendicular to the longitudinal axis of the device ("pushed")) by a user to turn on the drill bit 302, and/or set the desired speed of the drill bit 302. Alternatively, the motor can be actuated by a predetermined force (enough to start drilling a hole in a particular bone, which could change depending on type and hardness of a bone) imparted by a user via the handpiece 300 on to the inserter against bone. The handpiece 300 can also include a disposable plastic housing 305 to make the device lightweight, less expensive, and disposable. The disposable plastic housing 305 can be made from any plastic or combination of plastics. The inserter can also be made to be disposable, and be provided preattached to the handpiece 300 as a kit. The proximal end of the anchor inserter, as described herein, can be attached to the chuck 302 of the disposable handpiece 300. The disposable handpiece can be used to rotate the drilling ends 60A, 60B and their respective drilling points 54A, 54B, and push the inserter 10 into the bone 94 until the anchor braid 104 is fully inserted into the bone 94 (as described with respect to FIG. 27).

Generally, the following described and illustrated alternative all-suture anchor designs are configured to work with and be deployed by the anchor inserter described herein in the same manner as the other all-suture anchors, described above and illustrated herein. As with the other all-suture anchors, the alternative embodiments of the all-suture anchors can include a fibrous construct anchor body portion (or fibrous, braided or woven fabric-type structure such as a flexible web) and a suture or filament portion having a first end and a second end. The suture can pass through the filament in a number of ways (including woven, pass through a column, pierced through top and bottom, etc., as should be understood by a person of ordinary skill in the art in conjunction with a review of this disclosure). The fibrous construct can include a first state in which the fibrous construct is uncompressed and extends along the longitudinal axis of the filament when in an unfolded and pre-deployed condition; and a second state in which the flat fibrous construct is compressed and expanded in a direction perpendicular to longitudinal axis of the filament in a deployed condition (as discussed herein).

In accordance with one embodiment, the fibrous construct has an open elongated column/lumen extending from a first end to a second end; and the filament passes through and is positioned at least partially in the open column. In an embodiment, the filament is free to slide through the open column such that the filament can be removed from the open column from the first end of the fibrous construct and the second end of the fibrous construct. An embodiment of the fibrous construct can also be tubular in addition to having an open elongated column/lumen. The flat tape/fibrous construct may either be woven in situ directly onto the filament (e.g., a round section suture braid), or woven with an open column into which the round section suture braid may be later inserted. In particular, as seen in FIG. 44, a perspective view schematic representation of a soft all-suture anchor 400 in an unloaded (not loaded onto an installation device or inserter), pre-deployment configuration, according to an embodiment. The all-suture anchor 400 can include, but is not limited to, a flat fibrous construct 4 having a first end 4A, a second end 4B, and an open elongated column/lumen 6 having a first end 6A and the second end 6B (each of the first end 6A and the second end 6B of the open elongated column/lumen 6 can extend between or beyond the first 4A and second 4B ends of the flat fibrous construct). The open elongated column/lumen 6 can be woven along an axis that is parallel to or along a central axis of the flat fibrous construct 4, or can be woven along a path that is not parallel to the central axis. As shown in FIG. 44, the open elongated column/lumen is woven along the central axis.

Still referring to FIG. 44, a filament 2 is shown having a first end 2A and a second end 2B, and passing through and at least partially positioned in the open column 6. In an embodiment, the filament 2 is free to slide through the open column 6 such that the filament 2 can be removed from the open column 6 from the first end 2A of the fibrous construct 2 and/or the second end 2B of the fibrous construct 2. In accordance with an alternative embodiment, the filament is locked and not slidable through the open column 6.

Turning now to FIGS. 45A and 45B, there are shown side view schematic representations of an embodiment of the all-suture anchor 400 in the pre-deployment and post-deployment configurations. As described above, the all-suture anchor 400 contains at least two sections: at least one suture 2 with a first end 2A and a second end 2B; and an anchor body/fibrous construct 4 with a first end 4A and a second end 4B, and an open elongated column/lumen 6 extending from a first end 6A to a second end 6B, which is to form a portion of the anchor 400 that can increase in width, thickness and/or diameter and shrink in length as part of deployment.

As shown in FIG. 45A, the installation device (or inserter, as described herein above) in the pre-deployment configuration is provided. The all-suture anchor 400 is shown connected to the distal deployment end 804 of an installation device 800 (which can be an inserter of an embodiment described herein), which also includes a handle 802. The distal deployment end 804 and the all-suture anchor 100 are shown positioned in a bone hole 900 in cancellous bone 904 under the bone cortex 902. In order to deploy the all-suture anchor 400 (which can be connected to other tissue that needs to be brought into apposition to the bone, as should be understood by a person of ordinary skill in the art in conjunction with a review of this disclosure), the first end 2A and/or the second end 2B are pulled/tensioned in a direction away from the bone hole 400. The first end 2A and the second end 2B can be pulled/tensioned in a direction away from the bone hole 900 with or without the installation device 800 in place in the bone hole 900 (if installation device 800 is in place in the bone hole 900, it can act as a counter force to the tension force out of the hole 900 to assist with the deployment of the all-suture anchor 400).

As shown in FIG. 45B, the anchor body/fibrous construct 4 is shown "shortened" and "expanded" in the post-deployment configuration and locked in the bone hole 900, which can be additive to the increase due to pleats formed by the fibrous construct 4 (which may also be part of the fibrous construct 4). See also FIG. 45C. The all-suture anchor 400, and, in particular, the fibrous construct 4 takes advantage of Poisson's ratio (as described with respect to other anchors, above), which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. Although, it is the anchor body/fibrous construct 4 that increases in width, thickness and/or diameter at deployment, it should be understood that the suture 2 can also play a role in the deployment of the anchor 400 even though the suture 2 may remain free to slide in some embodiments, and non-slidable in others (at least at a particular position or point in use) in relation to the anchor body 4. The suture 2 helps to position, align and support the anchor body 4 (as should be understood by a person of skill in the art in conjunction with a review of this disclosure).

In other words, the anchor body/fibrous construct 4 has two primary functions. First, it becomes a base for the suture 2 to slide within (within the column/lumen 6). Second, when compressed and/or pleated during deployment, the anchor body 4 becomes more compact in one direction thereby expanding outwardly and increasing its overall width, thickness or diameter to create a retention capacity. This action of having the anchor body 4 change in shape to increase its overall width, thickness or diameter is a useful characteristic which may be used advantageously to secure the anchor 400 in a hole 900 or against a bony or soft tissue. It is this combination of the expanding anchor body 4 coupled with the suture 2 remaining slidable (in some embodiments; and non-slidable in others, at least at a particular position or point in use) in relation to the anchor body 4 that render embodiments of the present invention ideal for the reattachment of soft tissue to bone or soft tissue to soft tissue where it is desirable to pass sliding knots to secure a repair.

In one embodiment, an inventive configuration, structure, and resulting function of a soft all-suture anchor that utilizes a hybrid combination of soft implantable materials is provided. A hybrid soft all-suture anchor of an embodiment includes superior pull-out strength properties as compared to conventional soft all suture anchors. Embodiments of the present invention provide a better soft all-suture anchor for use in hard bone, due in part to a hybrid expanding component portion. These embodiments are also suitable for use in soft cancellous bone where there is a very thin or weak cortical layer. The hybrid all-suture anchor can include, but is not limited to, an expandable member/portion configured to increase in size from a first pre-deployed condition to a second deployed condition upon the application of an activator; and a filament having a first filament end and a second filament end, and positioned in contacting relation to the expandable member in the second deployed condition. The anchor can also include a flat fibrous construct having a first end and a second end, and wherein the filament passes through the fibrous construct. The flat fibrous construct includes a first state in which the flat fibrous construct is uncompressed and extends along the longitudinal axis of the filament when in an unfolded and pre-deployed condition; and a second state in which the flat fibrous construct is compressed and expanded in a direction perpendicular to longitudinal axis of the filament in a deployed condition. The structure, configuration, and functionality of the expandable member, and of the fibrous construct (when part of an embodiment), help to set and hold the anchor in the bone hole in a post-deployment condition. The expandable portion/member can be part of a hybrid all-suture anchor used with any filament portion (as described herein) only. The expandable portion/member can also be part of a hybrid all-suture anchor used with any filament portion and any fibrous construct portion (as described herein).

For example, referring to FIG. 46, a perspective view of a hybrid soft all-suture anchor 500 in a pre-deployment configuration, according to an embodiment is shown. The hybrid all-suture anchor 500 can include, but is not limited to, a flat fibrous construct 4 having a first end 4A, a second end 4B. A filament 2 is shown having a first end 2A and a second end 2B, and woven, threaded, or otherwise passing through the fibrous construct 4 at passing locations 25, 27 and 25, 28. See U.S. Pat. No. 9,826,971 for a further description of the structural aspects of the filament and fibrous construct, which is part of this example of the invention (as should be understood by a person of ordinary skill in the art in conjunction with a review of this disclosure).

In an embodiment, the filament 2 is free to slide through the fibrous construct 4 (and the expandable portion 3 when attached thereto) such that the filament 2 can be removed from the fibrous construct 4 from the first end 4A of the fibrous construct 4 and/or the second end 4B of the fibrous construct 4. In accordance with an alternative embodiment, the filament is locked and not slidable through the fibrous construct 4 and/or the expandable portion 3 (when attached to the expandable portion 3).

Turning now to FIGS. 47A and 47B, there are shown side view schematic representations of an embodiment of the all-suture anchor 500 in the pre-deployment and post-deployment configurations. As described above, the all-suture anchor 500 contains at least two sections: at least one suture 2 with a first end 2A and a second end 2B; and an anchor body/fibrous construct 4 with a first end 4A and a second end 4B, which is configured to form a portion of the anchor 500 that can increase in width, thickness and/or diameter and shrink in length as part of deployment. The all-suture anchor 500 also includes an expandable portion 3 which is configured to form a portion of the anchor 500 that can increase in size in the post-deployment configuration in response to an activator (as should be understood by a person of ordinary skill in the art in conjunction with a review of this disclosure).

As shown in FIG. 47A, the installation device (or inserter, as described herein above) in the pre-deployment configuration is provided. The all-suture anchor 500 is shown connected to the distal deployment end 804 of an installation device 800 (which can be an inserter, as described herein above), which also includes a handle 802. The distal deployment end 804 and the all-suture anchor 500 are shown positioned in a bone hole 900 in cancellous bone 904 under the bone cortex 902. In order to deploy the all-suture anchor 500 (which can be connected to other tissue that needs to be brought into apposition to the bone, as should be understood by a person of ordinary skill in the art in conjunction with a review of this disclosure), the first end 2A and/or the second end 2B are pulled/tensioned in a direction away from the bone hole 400. The first end 2A and the second end 2B can be pulled/tensioned in a direction away from the bone hole 900 with or without the installation device 800 in place in the bone hole 900 (if installation device 800 is in place in the bone hole 900, it can act as a counter force to the tension force out of the hole 900 to assist with the deployment of the all-suture anchor 500). In addition, an activator can be added to the anchor to cause the expandable portion to expand to a second size greater than the first pre-deployment size. In one embodiment, the activator is water.

As shown in FIG. 47B, the anchor body/fibrous construct 4 is shown "shortened" and "expanded" in the post-deployment configuration and locked in the bone hole 900, which can be additive to the increase due to pleats formed by the fibrous construct 4 (which may also be part of the fibrous construct 4). The all-suture anchor 500, and, in particular, the fibrous construct 4 takes advantage of Poisson's ratio (similarly, as discussed above), which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. Although, it is the anchor body/fibrous construct 4 that increases in width, thickness and/or diameter at deployment, it should be understood that the suture 2 can also play a role in the deployment of the anchor 500 even though the suture 2 may remain free to slide in some embodiments, and non-slidable in others (at least at a particular position or point in use) in relation to the anchor body 4. The suture 2 helps to position, align and support the anchor body 4 (as should be understood by a person of skill in the art in conjunction with a review of this disclosure).

In other words, the anchor body/fibrous construct 4 has two primary functions. First, it becomes a base for the suture 2 to slide within (within the column/lumen 6). Second, when compressed and/or pleated during deployment, the anchor body 4 becomes more compact in one direction thereby expanding outwardly and increasing its overall width, thickness or diameter to create a retention capacity. This action of having the anchor body 4 change in shape to increase its overall width, thickness or diameter is a useful characteristic which may be used advantageously to secure the anchor 500 in a hole 900 or against a bony or soft tissue. It is this combination of the expanding anchor body 4 coupled with the suture 2 remaining slidable (in some embodiments; and non-slidable in others, at least at a particular position or point in use) in relation to the anchor body 804 that render embodiments of the present invention ideal for the reattachment of soft tissue to bone or soft tissue to soft tissue where it is desirable to pass sliding knots to secure a repair.

Still referring to FIG. 47B, the expandable portion 3 is shown in the expanded second size, greater than the first smaller pre-deployment size, after exposure to the activator. The expandable portion expands greatly in volume when exposed to the activator, causing it to wedge in the bone hole 900 and lock the anchor 500 in place. In accordance with an embodiment, in order to tension the filament 2 to reattach soft tissue (not shown), the filament 2 can freely slide backward and forward through the fibrous construct 4 and through the expandable portion 3 (as may be necessary when connected to the expandable portion 3). In certain situations without the presence of fibrous construct 4, the free sliding filament 2 could potentially cut through the expandable portion 3 resulting in a less than optimum deployment of the all-suture anchor 500. As such, in some embodiments of the all-suture anchor 500 with or without the fibrous construct 4, a second short length of suture 2-1 could be wrapped or looped around the filament 2 (see FIG. 47C) to prevent sawing/cutting through the expandable portion 3 by the filament 2 when in contacting relation with the expandable portion 3.

Turning to FIG. 48, a side view digital photograph of an embodiment of the all-suture anchor of FIG. 46 in a post-deployment configuration after addition of an activator according to an embodiment is shown. As shown, the expandable portion 3 has increased in size to a second deployed structural condition (bone hole is not shown to illustrate the extent of expansion of expandable portion 3), and the filament 2 is positioned through and/or in otherwise contacting relation with the expandable portion 3.

Similarly with respect to the filament 2 and fibrous construct 4 described above and the embodiments shown in FIGS. 47A-C, the expandable portion 3 can be a part of any all-suture anchor described herein or otherwise including the all-suture anchor shown and described in U.S. patent application Ser. No. 16/033,616. The same structure and functionality of the expandable portion 3 described above and shown in FIGS. 47A-C can apply to these embodiments of an all-suture anchor (with and without the fibrous construct).

In accordance with an alternative embodiment of the present invention, an all-suture anchor insertion device 600 is provided as shown in FIGS. 49-51. The all-suture anchor insertion device 600 is configured to drill a bone hole in a desired anchor deployment location and deploy an all-suture anchor (which can include any all-suture anchor as discussed, referenced, described and/or illustrated herein) in the bone hole in one action with one device. In many procedures that involve soft tissue fixation in the extremities, a common issue is the surgeon losing the position of the hole they drilled in the bone for anchor deployment after removing the drill and guide. Additionally, during typical anchor insertion a drill guide must be held with one hand and the other hand is used to drill the pilot hole and insert the anchor. The all-suture anchor insertion device 600 incorporates a guide into the anchor which allows the procedure to be done single handed. The all-suture anchor insertion device 600 also reduces the time needed to install an anchor by combining the drilling and the anchor insertion steps into one. The uniqueness of the all-suture anchor insertion device 600 pertains, in part, to the use of an anchor driver rod 601 to drill a bone tunnel by oscillating it on a drill. The oscillating motion of the drill rotates the anchor driver rod 601 back and forth through. As the driver rod 601 oscillates, the tips of the fork 603-1 at the distal end of the device act as a drill bit to create a hole as a surgeon user pushes it into the bone. When the rod and anchor (positioned at the distal end of the device, not shown) have been inserted, the oscillation is stopped and the driver rod 601 is pulled out. The all-suture anchor is then set by pulling on the suture tails of the anchor, and/or adding an activator (as discussed herein).

In brief, as shown in FIGS. 49-51, the all-suture anchor insertion device 600 includes, but is not limited to, an anchor driver rod 601, a guide with a handle and a suture cleat 602, a sliding guide tip 603, a metal guide tube 604, and a single loaded all-suture anchor (not shown—preferably positioned on the distal end near the fork 603-1). The sliding guide tip 603 can be used to position an all-suture anchor before beginning to oscillate the device, and protects any surrounding tissues while the anchor is oscillating and being inserted.

A preferable functionality of the all-suture anchor insertion device 600 is to allow for anchor insertion with minimal steps from the surgeon in a method of using the same. In brief, the surgeon can connect a powered handpiece (not shown; e.g., as described above, or otherwise understood by a person of ordinary skill in the art in conjunction with a review of this disclosure) that has an equal oscillation mode to the back end of the inserter rod 601. Then holding the guide handle 602 and the powered hand piece the surgeon can position the sliding guide tip 603 at a location in bone and at an angle that they want to install the anchor. The surgeon can then turn on the oscillating mode of the hand piece, and push the inserter rod 601 into the bone (not shown). When the metal guide tube 604 becomes flush with the bone surface (and the distal end of the sliding guide tip 603 is flush with the distal end of the metal guide tube) oscillation can be stopped, the suture (not shown) is removed from the cleats, and the device is removed. The anchor can then be set by pulling on the suture tails, and/or and activator is added (as described herein and above).

Suture material, sutures, or filaments as the terms are used and described herein, can include monofilament or multi-filament suture as well as any other metallic or non-metallic filamentary or wire-like material suitable for performing the function of a suture. This material can include both bioabsorbable and non-absorbable materials, and can be round, flat, or braided.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. An anchor inserter, comprising:
   a shaft extending along a longitudinal axis having a proximal end and a distal end;
   an inserter tip attached to and extending distally from the shaft;
   a suture anchor retention slot extending through the inserter tip, the suture anchor retention slot having a pair of opposing inner walls; and
   a drilling point at a distal end of the inserter tip, and
   an anchor deployment passage extending from the suture anchor retention slot to an exterior distal surface of the inserter tip, the anchor deployment passage having:
      a pair of opposing drill faces,
      wherein the opposing drill faces are spaced closer together than the opposing inner walls of the suture anchor retention slot.

2. The anchor inserter of claim 1, wherein the inner walls are at an angle offset from the drill faces.

3. The anchor inserter of claim 1, further comprising a quick change connector attached to and extending proximally from the shaft.

4. The anchor inserter of claim 3, wherein the quick change connector comprises a distal adapter and a rod extending proximally therefrom.

5. The anchor inserter of claim 4, wherein the rod comprises at least one flat surface.

6. The anchor inserter of claim 1, further comprising:
   a tubular portion connected to the distal end of the shaft;
   an outer tube of the tubular portion having a first inner volume; and
   a suture tube of the tubular portion having a second inner volume, the suture tube extending within the first inner volume of the outer tube.

7. The anchor inserter of claim 6, wherein the shaft extends into at least a distal portion of the outer tube and at least a distal portion of the suture tube, and at least a proximal portion of the outer tube extends into a quick change connector.

8. A self-drilling anchor inserter system, comprising:
   a shaft extending along a longitudinal axis having a proximal end and a distal end, the distal end connected to a tubular portion;
   an inserter tip attached to and extending distally from the shaft;
   a suture anchor retention slot extending through the inserter tip;
   a drilling point at the distal end of the inserter tip; and
   an anchor with a length of suture positioned therethrough extending through the suture anchor retention slot, such that a first end of the length of suture extends along a first side of the shaft and a second end of the length of suture extends along a second side of the shaft,
   an anchor deployment passage extending from the suture anchor retention slot to an exterior distal surface of the inserter tip;
   wherein the inserter tip comprises a pair of prongs, each prong extending along a side of the suture anchor retention slot and anchor deployment passage, the prongs being spaced closer together in the anchor deployment passage than in the suture anchor retention slot.

9. The self-drilling anchor inserter system of claim 8, wherein the anchor is an anchor braid with the length of suture positioned through one surface of the anchor braid.

10. The self-drilling anchor inserter system of claim 8, wherein, in a loaded, pre-deployment configuration, the anchor is twisted around the at least a portion of the shaft.

11. The self-drilling anchor inserter system of claim 8, wherein the suture anchor retention slot comprises a rounded proximal edge and a sharp distal edge.

12. The self-drilling anchor inserter system of claim 8, further comprising a plurality of passing locations along the anchor, wherein the length of suture is woven through the anchor at the plurality of passing locations.

13. The self-drilling anchor inserter system of claim 8, further comprising:
   an outer tube of the tubular portion having a first inner volume; and
   a suture tube of the tubular portion having a second inner volume, the suture tube extending within the first inner volume of the outer tube.

14. The self-drilling anchor inserter system of claim 13, wherein in a loaded, pre-deployment configuration, the first end of the length of suture is between the first side of the shaft and the suture tube and the second end of the length of suture is between the second side of the shaft and the suture tube.

15. The self-drilling anchor inserter system of claim 8, wherein the prongs cannot move in opposing directions along a z-z axis, the z-z axis being perpendicular to the longitudinal axis.

16. The self-drilling anchor inserter system of claim 8, further comprising an AO compatible quick chance connector attached to and extending proximally from the tubular portion.

17. An anchor inserter, comprising:
   a shaft extending along a longitudinal axis having a proximal end and a distal end;
   an inserter tip attached to and extending distally from the shaft;

a suture anchor retention slot extending through the inserter tip;
a drilling point at the distal end of the inserter tip;
a tubular portion connected to the distal end of the shaft;
an outer tube of the tubular portion having a first inner volume; and
a suture tube of the tubular portion having a second inner volume, the suture tube extending within the first inner volume of the outer tube.

18. A self-drilling anchor inserter system, comprising:
a shaft extending along a longitudinal axis having a proximal end and a distal end, the distal end connected to a tubular portion;
an inserter tip attached to and extending distally from the shaft;
a suture anchor retention slot extending through the inserter tip;
a drilling point at the distal end of the inserter tip; and
an anchor with a length of suture positioned therethrough extending through the suture anchor retention slot, such that a first end of the length of suture extends along a first side of the shaft and a second end of the length of suture extends along a second side of the shaft;
an outer tube of the tubular portion having a first inner volume; and
a suture tube of the tubular portion having a second inner volume, the suture tube extending within the first inner volume of the outer tube.

19. A method of drilling a bone hole and inserting a suture anchor, the method comprising the steps of:
providing an inserter comprising a shaft extending along a longitudinal axis having a proximal end and a distal end, the distal end connected to a tubular portion, an inserter tip attached to and extending distally from the shaft, a suture anchor retention slot extending through the inserter tip, and a drilling point at the distal end of the inserter tip;
inserting a suture anchor with a length of suture positioned therethrough through the suture anchor retention slot;
tensioning a first end of the length of suture on a first side of the shaft and a second end of the length of suture on a second side of the shaft;
positioning a distal end of a guide tube against a bone;
extending the inserter through the guide tube such that the drilling point is at a surface of a bone at a desired bone hole location; and
drilling a bone hole into the bone with the drilling point of the inserter.

20. The method of claim 19 wherein the step of drilling a bone hole into the bone with the drilling point of the inserter comprises the step of rotating the drilling point against the surface of the bone.

21. The method of claim 19 further comprising the step of implanting the suture anchor into the bone hole.

* * * * *